(12) United States Patent
Wang et al.

(10) Patent No.: US 9,045,549 B2
(45) Date of Patent: Jun. 2, 2015

(54) TRANSCRIPTION FACTORS FOR MODIFICATION OF LIGNIN CONTENT IN PLANTS

(75) Inventors: Huanzhong Wang, Storrs, CT (US);
Fang Chen, Ardmore, OK (US);
Richard A. Dixon, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 630 days.

(21) Appl. No.: 13/288,677

(22) Filed: Nov. 3, 2011

(65) Prior Publication Data
US 2012/0117691 A1   May 10, 2012

Related U.S. Application Data

(60) Provisional application No. 61/409,871, filed on Nov. 3, 2010.

(51) Int. Cl.
| | |
|---|---|
| *C12N 15/82* | (2006.01) |
| *C12N 15/63* | (2006.01) |
| *C12N 15/09* | (2006.01) |
| *A01H 5/04* | (2006.01) |
| *C07K 14/415* | (2006.01) |

(52) U.S. Cl.
CPC .......... *C07K 14/415* (2013.01); *C12N 15/8245* (2013.01); *C12N 15/8246* (2013.01); *C12N 15/8255* (2013.01); *C12N 15/8261* (2013.01); *Y02E 50/16* (2013.01)

(58) Field of Classification Search
None
See application file for complete search history.

(56) References Cited

U.S. PATENT DOCUMENTS

| | | | | |
|---|---|---|---|---|
| 2005/0235375 | A1* | 10/2005 | Chen et al. | 800/278 |
| 2008/0229439 | A1 | 9/2008 | La Rosa et al. | |

FOREIGN PATENT DOCUMENTS

WO   WO 2005/001050 A2   1/2005

OTHER PUBLICATIONS

Pandey and Somssich 2009 Plant Physiology 150:1648-1655.*
Archana K et al., "Down-regulation of an abiotic stress related *Nicotiana benthamiana* WRKY transcription factor induces physiological abnormalities," *Indian Journal of Biotechnology*, 8(1):53-60, Jan. 2009.
Caño-Delgado Al et al., "The eli1 mutation reveals a link between cell expansion and secondary cell wall formation in *Arabidopsis thaliana*," *Development*, 127(15):3395-405, Aug. 2000.
Ellis C et al., "The *Arabidopsis* mutant cev1 links cell wall signaling to jasmonate and ethylene responses," *Plant Cell.*, 14(7):1557-66, Jul. 2002.
Eulgem T et al., "The WRKY superfamily of plant transcription factors," *Trends in Plant Science*, 5(5):199-206, May 2000.
Guillaumie S et al., "The grapevine transcription factor WRKY2 influences the lignin pathway and xylem development in tobacco," *Plant Molecular Biology*, 72(1-2):215-234, Jan. 2010.
Ko JH et al., "Ectopic expression of MYB46 identifies transcriptional regulatory genes involved in secondary wall biosynthesis in *Arabidopsis,*" *Plant J.*, 60(4):649-65, Nov. 2009.
Mzid Rim et al: "Overexpression of VvWRKY2 in tobacco enhances broad resistance to necrotrophic fungal pathogens," *Physiologia Plantarum*, 131(3):434-447, November.
Naoumkina Marina A et al., "Elicitor-induced transcription factors for metabolic reprogramming of secondary metabolism in *Medicago truncatula*," *BMC Plant Biology, Biomed Central*, 8(1), Dec. 22, 2008, London, GB.
Wang H et al., "Mutation of WRKY transcription factors initiates pith secondary wall formation and increases stem biomass in dicotyledonous plants," *PNAS (U.S.A.)*, 107(51): 22338-22343, Dec. 2010.
Wang H et al., "Overexpression of rice WRKY89 enhances ultraviolet B tolerance and disease resistance in rice plants," *Plant Molecular Biology*, 65(6):799-815, Oct. 25 2007, Kluwer Academic Publishers, Dordrecht, NL.
Wang H et al., "NAC domain function and transcriptional control of a secondary cell wall master switch," *Plant J.*, 68(6):1104-1114, Dec. 2011.
Wang HZ, Dixon RA, "On-off switches for secondary cell wall biosynthesis,".*Mol Plant*, 5(2):297-303, Mar. 2012.
Wang, H., "WRKY transcription factors control pith secondary wall formation and affect stem biomass production," Abstract; *Plant Biology 2011 ASPB Meeting / Conference; American Society of Plant Biologists*, 10, Aug. 6, 2011.
Zhao Q et al., "Syringyl lignin biosynthesis is directly regulated by a secondary cell wall master switch," *Proc Natl Acad Sci U S A*, 107(32):14496-501, Aug. 10, 2010.
Zhao Qiao et al., "An NAC transcription factor orchestrates multiple features of cell wall development in *Medicago truncatula*," *Plant Journal*, 63(1): 100-114, Jul. 2010.
Zhong R et al., "A battery of transcription factors involved in the regulation of secondary cell wall biosynthesis in *Arabidopsis,*" *Plant Cell*, (10):2763-82, Oct. 20, 2008.
GenBank Accession No. HM622066; Wang et al.
GenBank Accession No. IMGA|AC202489_11.1; <http://plantgrn.noble.org/LegumeIP/getseq.do?seq_acc=IMGA%7CAC202489_11.1>.
GenBank Accession No. ABY84655.1, dated Feb. 3, 2008.
GenBank Accession No. CBI16682.3, dated Jun. 8, 2010.

* cited by examiner

*Primary Examiner* — Brent T Page
(74) *Attorney, Agent, or Firm* — Dentons US LLP

(57) ABSTRACT

The invention provides methods for modifying lignin, cellulose, xylan, and hemicellulose content in plants, and for achieving ectopic lignification and, for instance, secondary cell wall synthesis in pith cells, by altered regulation of a WRKY transcription factor. Nucleic acid constructs for altered WRKY-TF expression are described. Transgenic plants are provided that comprise modified pith cell walls, and lignin, cellulose, and hemicellulose content. Plants described herein may be used, for example, as improved biofuel feedstock and as highly digestible forage crops.

23 Claims, 21 Drawing Sheets

US 9,045,549 B2

SEQUENCE LISTING

<160> NUMBER OF SEQ ID NOS: 43

<210> SEQ ID NO 1
<211> LENGTH: 227
<212> TYPE: PRT
<213> ORGANISM: Medicago truncatula

<400> SEQUENCE: 1

```
Met Asp Gly Glu Arg Asp Val Pro Asn Tyr Asp Leu Gln Val Ser Phe
1               5                   10                  15

Thr Asn Thr Pro Gln Ala Ile His Glu Met Gly Phe Val Gln Phe Glu
            20                  25                  30

Glu Asn Gln Val Leu Ser Phe Leu Ser Pro Ser Thr Gln Ser Gln Pro
        35                  40                  45

Ser Gln Leu Ser Gln Ser Leu Asn Ser Gly Arg Gly Thr Thr Asn Ala
    50                  55                  60

Thr Thr Gly Ala Ala Val Thr Thr Thr Val Ala Ala Gly Phe Ser
65                  70                  75                  80

His Asn Asp Leu Val Thr Thr Arg Thr Pro Trp Asn Asn Glu Gln Val
                85                  90                  95

Arg Thr Leu Asp Pro Lys Ala Val Ser Asp Glu Asn Cys Thr Gly Asn
            100                 105                 110

Thr Ser Asp Gly Asn Asn Thr Trp Trp Arg Ser Gly Gly Ala Glu Lys
        115                 120                 125

Ser Lys Val Lys Val Arg Arg Lys Leu Arg Glu Pro Arg Phe Cys Phe
    130                 135                 140

Gln Thr Arg Ser Asp Val Asp Val Leu Asp Gly Tyr Lys Trp Arg
145                 150                 155                 160

Lys Tyr Gly Gln Lys Val Val Lys Asn Ser Leu His Pro Arg Ser Tyr
                165                 170                 175

Tyr Arg Cys Thr His Asn Asn Cys Arg Val Lys Lys Arg Val Glu Arg
            180                 185                 190

Leu Ser Glu Asp Cys Arg Met Val Ile Thr Thr Tyr Glu Gly Arg His
        195                 200                 205

Asn His Ser Pro Cys Asp Asp Ser Asn Ser Ser Glu His Glu Cys Phe
    210                 215                 220

Thr Ser Phe
225
```

<210> SEQ ID NO 2
<211> LENGTH: 227
<212> TYPE: PRT
<213> ORGANISM: Medicago sativa

<400> SEQUENCE: 2

```
Met Asp Gly Glu Arg Asp Val Pro Asn Tyr Asp Leu Gln Val Ser Phe
1               5                  10                  15

Thr Asn Thr Ser Gln Ala Ile His Glu Met Gly Phe Val Gln Phe Glu
            20                  25                  30

Glu Asn Gln Val Leu Ser Phe Leu Ser Pro Ser Thr Gln Ser Gln Pro
        35                  40                  45

Ser Gln Leu Ser Gln Ser Leu Asn Ser Gly Arg Ser Thr Thr Asn Ala
    50                  55                  60

Thr Thr Gly Ala Ala Val Thr Thr Thr Val Ala Ala Gly Phe Ser
65                  70                  75                  80

His Asn Asp Leu Val Thr Thr Arg Thr Pro Trp Asn Glu Gln Val
                85                  90                  95

Arg Thr Leu Asp Pro Lys Ala Val Ser Asp Glu Asn Cys Thr Gly Asn
            100                 105                 110

Thr Ser Asp Gly Asn Asn Thr Trp Trp Arg Ser Gly Gly Ala Glu Lys
        115                 120                 125

Ser Lys Ala Lys Val Arg Arg Lys Leu Arg Glu Pro Arg Phe Cys Phe
    130                 135                 140

Gln Thr Arg Ser Asp Val Asp Val Leu Asp Asp Gly Tyr Lys Trp Arg
145                 150                 155                 160

Lys Tyr Gly Gln Lys Val Val Lys Asn Ser Leu His Pro Arg Ser Tyr
                165                 170                 175

Tyr Arg Cys Thr His Asn Asn Cys Arg Val Lys Lys Arg Val Glu Arg
            180                 185                 190

Leu Ser Glu Asp Cys Arg Met Val Ile Thr Thr Tyr Glu Gly Arg His
        195                 200                 205

Asn His Ser Pro Cys Asp Asp Ser Asn Ser Glu His Glu Cys Phe
    210                 215                 220

Thr Ser Phe
225
```

<210> SEQ ID NO 3
<211> LENGTH: 218
<212> TYPE: PRT
<213> ORGANISM: Arabidopsis thaliana

<400> SEQUENCE: 3

```
Met Glu Gly Gly Gly Arg Arg Val Phe Ser Asn Tyr Asp Leu Gln Gln
1               5                  10                  15

Val Thr Ser Ser Ser Thr Thr Ile Gln Glu Asn Met Asn Phe Leu Val
            20                  25                  30

Pro Phe Glu Glu Thr Asn Val Leu Thr Phe Phe Ser Ser Ser Ser Ser
        35                  40                  45

Ser Ser Leu Ser Ser Pro Ser Phe Pro Ile His Asn Ser Ser Ser Thr
    50                  55                  60

Thr Thr Thr His Ala Pro Leu Gly Phe Ser Asn Asn Leu Gln Gly Gly
65                  70                  75                  80

Gly Pro Leu Gly Ser Lys Val Val Asn Asp Asp Gln Glu Asn Phe Gly
                85                  90                  95

Gly Gly Thr Asn Asn Asp Ala His Ser Asn Ser Trp Trp Arg Ser Asn
```

```
            100             105             110
Ser Gly Ser Gly Asp Met Lys Asn Lys Val Lys Ile Arg Arg Lys Leu
            115             120             125

Arg Glu Pro Arg Phe Cys Phe Gln Thr Lys Ser Asp Val Asp Val Leu
            130             135             140

Asp Asp Gly Tyr Lys Trp Arg Lys Tyr Gly Gln Lys Val Val Lys Asn
145             150             155             160

Ser Leu His Pro Arg Ser Tyr Tyr Arg Cys Thr His Asn Asn Cys Arg
            165             170             175

Val Lys Lys Arg Val Glu Arg Leu Ser Glu Asp Cys Arg Met Val Ile
            180             185             190

Thr Thr Tyr Glu Gly Arg His Asn His Ile Pro Ser Asp Asp Ser Thr
            195             200             205

Ser Pro Asp His Asp Cys Leu Ser Ser Phe
            210             215
```

<210> SEQ ID NO 4
<211> LENGTH: 205
<212> TYPE: PRT
<213> ORGANISM: Populus balsamifera subsp. trichocarpa

<400> SEQUENCE: 4

```
Met Asp His Gly Glu Arg Asp Val Pro Asn Tyr Glu Leu His Val Ser
1               5               10              15

Phe Ser Thr Pro Gln Ala Ile His Glu Met Gly Phe Val Gln Phe Glu
            20              25              30

Glu Asn Gln Val Leu Ser Phe Leu Ala Pro Ser Gln Ser Ser Gln Ile
            35              40              45

Ser Gln Pro Leu Asn Ala Asn Thr Thr Thr Asn Asn Thr His Met
50              55              60

Gly Phe Ser His Asn Asp Gln Gln Val Gly Ala Leu Asp Pro Lys Ala
65              70              75              80

Ser Ser Asp Glu Asn Cys Thr Gly Asn Ala Asn Asn Asp Gly Asn Asn
            85              90              95

Ser Trp Trp Arg Ser Ser Ser Ala Asp Lys Asn Lys Leu Lys Val Arg
            100             105             110

Arg Lys Leu Arg Glu Pro Arg Phe Cys Phe Gln Thr Arg Ser Glu Val
            115             120             125

Asp Val Leu Asp Asp Gly Tyr Lys Trp Arg Lys Tyr Gly Gln Lys Val
            130             135             140

Val Lys Asn Ser Leu His Pro Arg Ser Tyr Tyr Arg Cys Thr His Asn
145             150             155             160

Asn Cys Arg Val Lys Lys Arg Val Glu Arg Leu Ser Glu Asp Cys Arg
            165             170             175

Met Val Ile Thr Thr Tyr Glu Gly Arg His Asn His Ser Pro Cys Asp
            180             185             190

Asp Ser Asn Ser Ser Glu His Glu Cys Phe Ser Ser Phe
            195             200             205
```

<210> SEQ ID NO 5
<211> LENGTH: 228
<212> TYPE: PRT
<213> ORGANISM: Vitis vinifera

<400> SEQUENCE: 5

Met Asp His His His His Gln Gly Glu Arg Ser Gly Val Pro Asn Tyr

```
1               5                   10                  15
Glu Leu Gln Val Ser Tyr Ser Thr Thr Pro Gln Gly Ile His Glu Met
                20                  25                  30

Gly Phe Val Gln Phe Glu Glu Asn Gln Val Leu Ser Phe Leu Ala Pro
                35                  40                  45

Ser Gln Ser Ala Gln Met Ser Gln Pro Leu Asn Thr Ala Ser Thr Ser
                50                  55                  60

Thr Pro Thr Pro Thr Pro Thr Asn Thr Thr Asn Thr Thr Met Gly
 65                  70                  75                  80

Phe Thr His Asn Asp Leu Leu Thr Arg Pro Ser Trp Asn Asn Glu Gln
                85                  90                  95

Val Gly Thr Leu Asp Pro Lys Ala Val Asn Glu Glu Asn Cys Thr Gly
               100                 105                 110

Asn Ala Asn Asp Gly Ser Asn Ser Trp Trp Arg Ser Ser Ser Ser Glu
               115                 120                 125

Lys Thr Lys Val Lys Ala Arg Arg Lys Leu Arg Glu Pro Arg Phe Cys
   130                 135                 140

Phe Gln Thr Arg Ser Glu Val Asp Val Leu Asp Asp Gly Tyr Lys Trp
145                 150                 155                 160

Arg Lys Tyr Gly Gln Lys Val Val Lys Asn Ser Leu His Pro Arg Ser
               165                 170                 175

Tyr Tyr Arg Cys Thr His Thr Asn Cys Arg Val Lys Lys Arg Val Glu
   180                 185                 190

Arg Leu Ser Glu Asp Cys Arg Met Val Ile Thr Thr Tyr Glu Gly Arg
   195                 200                 205

His Asn His Ser Pro Cys Asp Asp Ser Asn Ser Ser Glu His Glu Cys
   210                 215                 220

Phe Thr Ser Phe
225

<210> SEQ ID NO 6
<211> LENGTH: 225
<212> TYPE: PRT
<213> ORGANISM: Glycine max

<400> SEQUENCE: 6

Met Glu Ala Glu Arg Gly Gly Ala Pro Asn Tyr Glu Leu Gln Val Ser
 1               5                  10                  15

Phe Thr Asn Thr Pro Gln Ala Leu His Glu Met Gly Phe Val Gln Tyr
                20                  25                  30

Glu Glu Asn Gln Val Leu Gly Phe Leu Ser Pro Ser Gln Ser Gln
                35                  40                  45

Ser Ser His Leu Ser Gln Ser Leu Asn Ser Asp Thr Gly Val Val Ala
                50                  55                  60

Val Thr Ala Thr Thr Pro Thr Ala Thr Ile Gly Phe Met Ser His Ser
 65                  70                  75                  80

Gly Leu Val Thr Lys Thr Trp Asn Asn Asp Gln Val Gly Thr Leu Asp
                85                  90                  95

Pro Lys Pro Val Glu Asp Glu Asn Cys Thr Gly Asn Gly Ser Asp Gln
               100                 105                 110

Gly Asn Asn Asn Thr Trp Trp Arg Ser Ala Ala Thr Glu Lys Asn Lys
   115                 120                 125

Val Lys Ile Arg Arg Lys Leu Arg Glu Pro Arg Phe Cys Phe Gln Thr
   130                 135                 140
```

```
Arg Ser Asp Val Asp Val Leu Asp Asp Gly Tyr Lys Trp Arg Lys Tyr
145                 150                 155                 160

Gly Gln Lys Val Val Lys Asn Ser Leu His Pro Arg Ser Tyr Tyr Arg
                165                 170                 175

Cys Thr His Asn Asn Cys Arg Val Lys Lys Arg Val Glu Arg Leu Ser
                180                 185                 190

Glu Asp Cys Arg Met Val Ile Thr Thr Tyr Glu Gly Arg His Asn His
            195                 200                 205

Ser Pro Cys Asp Asp Ser Asn Ser Glu Asn Glu Cys Phe Thr Ser
    210                 215                 220

Phe
225

<210> SEQ ID NO 7
<211> LENGTH: 234
<212> TYPE: PRT
<213> ORGANISM: Sorghum bicolor

<400> SEQUENCE: 7

Met Glu Gly Gly Gln Leu Ser Ala Cys Leu Pro Gly Phe Leu Val Pro
1               5                   10                  15

Asp His Tyr Ala Phe Pro Leu Pro Leu Pro Leu Gln Leu Pro Ser Ser
                20                  25                  30

Gln Asn Lys Leu Phe Gln Met Pro Phe Val Val Asp Gln Glu Ala Glu
            35                  40                  45

Thr Glu Asn His Gly Gly Gly Met Leu Ser Ser Asp His Cys Gly
    50                  55                  60

Leu Tyr Pro Leu Pro Ala Leu Pro Phe Gly Ser Cys Ser Gly Ala Ala
65                  70                  75                  80

Gly Ala Ala Thr Ala Cys Gly Gly Lys Pro Thr Ala Gly Phe Met Pro
                85                  90                  95

Ser Ala Ile Val Ala Glu Glu Val Cys Thr Ser Val Thr Thr Lys Leu
                100                 105                 110

Gly Cys Asn Asp Ser Asn Gly Thr Trp Trp Lys Gly Ser Ala Ala Thr
            115                 120                 125

Thr Ile Ala Glu Arg Gly Lys Met Lys Val Arg Arg Lys Met Arg Glu
130                 135                 140

Pro Arg Phe Cys Phe Gln Thr Arg Ser Asp Val Asp Val Leu Asp Asp
145                 150                 155                 160

Gly Tyr Lys Trp Arg Lys Tyr Gly Gln Lys Val Val Lys Asn Ser Leu
                165                 170                 175

His Pro Arg Ser Tyr Phe Arg Cys Thr His Ser Asn Cys Arg Val Lys
            180                 185                 190

Lys Arg Val Glu Arg Leu Ser Thr Asp Cys Arg Met Val Met Thr Thr
            195                 200                 205

Tyr Glu Gly Arg His Thr His Ser Pro Cys Ser Asp Asp Ala Ser Ser
    210                 215                 220

Ala Asp His Thr Asp Cys Phe Thr Ser Phe
225                 230

<210> SEQ ID NO 8
<211> LENGTH: 212
<212> TYPE: PRT
<213> ORGANISM: Oryza sativa

<400> SEQUENCE: 8
```

```
Met Pro Leu Pro Pro Leu Gln Leu Pro Cys His Pro Lys Leu Leu
1               5                   10                  15

Gln Met Pro Phe Asp Gln Glu Asp Gln Pro Gly Ile His Gly Val Met
            20                  25                  30

Leu Ser Ser Asp His Cys Gly Leu Tyr Pro Leu Pro Ala Leu Pro Leu
        35                  40                  45

Ser Asn Ser Ala Ala Ala Ala Ala Thr Val Ala Leu Gly Lys His
50                  55                  60

Ser Ala Ala Ala Gly Ser Met Pro Asn Ile Gly Ala Glu Glu Val
65              70                  75                  80

Ala Thr Thr Val Thr Lys Ala Gly Asn Glu Ser Thr Thr Cys Asn Gly
                85                  90                  95

Ser Thr Thr Trp Trp Arg Gly Ser Thr Met Ala Ala Gly Glu Lys
            100                 105                 110

Gly Lys Met Lys Ile Arg Arg Lys Met Arg Glu Pro Arg Phe Cys Phe
            115                 120                 125

Gln Thr Arg Ser Glu Val Asp Val Leu Asp Asp Gly Tyr Lys Trp Arg
        130                 135                 140

Lys Tyr Gly Gln Lys Val Val Lys Asn Ser Leu His Pro Arg Ser Tyr
145                 150                 155                 160

Phe Arg Cys Thr His Ser Asn Cys Arg Val Lys Lys Arg Val Glu Arg
                165                 170                 175

Leu Ser Thr Asp Cys Arg Met Val Ile Thr Thr Tyr Glu Gly Arg His
            180                 185                 190

Thr His Ser Pro Cys Asp Asp Asn Ser Ser Gly Glu His Thr Asn Cys
        195                 200                 205

Phe Ser Ser Phe
    210

<210> SEQ ID NO 9
<211> LENGTH: 229
<212> TYPE: PRT
<213> ORGANISM: Triticum aestivum

<400> SEQUENCE: 9

Met Glu Gly Gly Ser Gln Leu Gly Ala Cys Leu Pro Ser Leu Tyr Ala
1               5                   10                  15

Leu Asp Pro Tyr Ala Ser Pro Pro Leu Leu Ala Pro Leu Pro Asn Gln
            20                  25                  30

His Lys Leu His Gln Leu Pro Leu Val Leu Gln Glu Gln Pro Gly Asn
        35                  40                  45

His Gly Val Met Phe Ser Ser Asp His Gly Gly Leu Tyr Pro Leu
50                  55                  60

Leu Pro Gly Ile Pro Phe Cys His Ser Ala Ala Cys Glu Lys Ser
65              70                  75                  80

Thr Gly Phe Ala Pro Leu Gly Gly Thr Gly Glu Ala Gly Thr Ser Ala
                85                  90                  95

Ala Arg Ala Gly Asn Glu Phe Ala Ser Ala Thr Thr Thr Thr Ala
            100                 105                 110

Ser Cys His Gly Pro Ser Ser Trp Trp Lys Gly Ala Glu Lys Gly Lys
        115                 120                 125

Met Lys Val Arg Arg Lys Met Arg Glu Pro Arg Phe Cys Phe Gln Thr
        130                 135                 140

Arg Ser Glu Val Asp Val Leu Asp Asp Gly Tyr Lys Trp Arg Lys Tyr
145                 150                 155                 160
```

```
Gly Gln Lys Val Val Lys Asn Ser Leu His Pro Arg Ser Tyr Tyr Arg
            165                 170                 175
Cys Thr His Ser Asn Cys Arg Val Lys Arg Val Glu Arg Leu Ser
            180                 185                 190
Glu Asp Cys Arg Met Val Ile Thr Thr Tyr Glu Gly Arg His Thr His
            195                 200                 205
Thr Pro Cys Ser Asp Asp Ala Gly Gly Asp His Thr Gly Ser Cys
        210                 215                 220
Ala Phe Thr Ser Phe
225

<210> SEQ ID NO 10
<211> LENGTH: 284
<212> TYPE: PRT
<213> ORGANISM: Zea mays

<400> SEQUENCE: 10

Met Pro Pro Asn Thr Thr Leu Thr His Pro Ile Asp Gln Leu Ile Thr
1               5                   10                  15
Thr Thr Thr His Thr Pro His Gly Arg Ser Ile Leu Leu Tyr Ala Cys
            20                  25                  30
Met Glu Gly Ser Ser Ser Gln Leu Leu Glu Thr Cys Leu Pro Ala Ser
        35                  40                  45
Leu Tyr Ala Val Thr Pro Pro Cys Ala His Pro His Pro Leu Leu
    50                  55                  60
Ala Pro Leu Pro Asn Gln Gln His Met Leu Leu Gln Met Pro Phe Val
65                  70                  75                  80
Lys Glu Gln Ala Ala Asn Asn His Gly Leu Met Leu Ser Ser Asp His
                85                  90                  95
His His His Ser Gly Leu Leu Tyr Pro Leu Leu Leu Pro Gly Ile Pro
            100                 105                 110
Phe Cys Pro Ser Val Ala Ala Ala Cys Glu Lys Thr Thr Thr Thr Gly
        115                 120                 125
Ser Gly Ala Leu Asp Ala Gly Glu Ala Gly Thr Ser Ser Ala Ala Ala
    130                 135                 140
Lys Ala Thr Gly Glu Ile Ala Ser Thr Ala Ala Thr Ala Cys Asn Ser
145                 150                 155                 160
Pro Ser Ser Cys Asn Trp Trp Lys Gly Pro Ala Ala Ala Ala Gly
                165                 170                 175
Glu Lys Gly Gly Arg Met Lys Val Arg Arg Lys Met Arg Glu Pro Arg
            180                 185                 190
Phe Cys Phe Gln Thr Arg Ser Asp Val Asp Val Leu Asp Asp Gly Tyr
        195                 200                 205
Lys Trp Arg Lys Tyr Gly Gln Lys Val Val Lys Asn Ser Leu His Pro
    210                 215                 220
Arg Ser Tyr Tyr Arg Cys Thr His Ser Asn Cys Arg Val Lys Lys Arg
225                 230                 235                 240
Val Glu Arg Leu Ser Glu Asp Cys Arg Met Val Met Thr Thr Tyr Glu
                245                 250                 255
Gly Arg His Thr His Ser Pro Cys Ser Asp Asp Ala Asp Ala Gly Gly
            260                 265                 270
Gly Asp His Thr Gly Ser Cys Ala Phe Thr Ser Leu
        275                 280
```

<210> SEQ ID NO 11
<211> LENGTH: 248
<212> TYPE: PRT
<213> ORGANISM: Sorghum bicolor

<400> SEQUENCE: 11

Met Glu Gly Ser Ser Gln Leu Leu Glu Thr Cys Leu Pro Ala Ser Ser
1               5                   10                  15

Leu Tyr Ala Leu Ser Pro His His Pro Leu Ala Pro Leu Pro Asn
            20                  25                  30

Gln His Lys Leu Leu Gln Met Pro Leu Val Gln Glu Gln Ala Ala Ala
        35                  40                  45

Asn Asn His Gly Val Met Leu Tyr Ser Asp His His His Gly Gly
    50                  55                  60

Gly Leu Leu Tyr Pro Leu Leu Pro Gly Ile Pro Phe Cys Pro Phe
65                  70                  75                  80

Ser Ala Ala Ala Asp Ala Ala Thr Cys Asp Lys Thr Thr Thr Gly
                85                  90                  95

Gly Phe Ala Ala Leu Asp Ala Gly Glu Ala Gly Thr Ser Val Ala Lys
            100                 105                 110

Ala Ala Gly Glu Ile Ala Ser Thr Thr Thr Cys Asn Gly Pro Ser
        115                 120                 125

Ser Cys Asn Trp Trp Lys Gly Pro Ala Ala Gly Glu Lys Gly Gly
    130                 135                 140

Arg Met Lys Val Arg Arg Lys Met Arg Glu Pro Arg Phe Cys Phe Gln
145                 150                 155                 160

Thr Arg Ser Asp Val Asp Val Leu Asp Asp Gly Tyr Lys Trp Arg Lys
                165                 170                 175

Tyr Gly Gln Lys Val Val Lys Asn Ser Leu His Pro Arg Ser Tyr Tyr
            180                 185                 190

Arg Cys Thr His Ser Asn Cys Arg Val Lys Lys Arg Val Glu Arg Leu
        195                 200                 205

Ser Glu Asp Cys Arg Met Val Ile Thr Thr Tyr Glu Gly Arg His Thr
    210                 215                 220

His Ser Pro Cys Ser Asp Asp Ala Asp Ala Ala Ala Gly Asp His Thr
225                 230                 235                 240

Gly Ser Cys Ala Phe Thr Ser Leu
                245

<210> SEQ ID NO 12
<211> LENGTH: 142
<212> TYPE: PRT
<213> ORGANISM: Populus balsamifera subsp. trichocarpa

<400> SEQUENCE: 12

Met Gly Phe Ser His Asn Asp Glu Gln Val Gly Thr Met Asp Pro Lys
1               5                   10                  15

Pro Ser Ser Asp Glu Asn Cys Thr Gly Asn Ala Asn Asn Asp Gly Asn
            20                  25                  30

Asn Ser Trp Trp Arg Ser Ser Ser Glu Lys Asn Arg Leu Lys Val
        35                  40                  45

Arg Arg Lys Leu Arg Glu Pro Arg Phe Cys Phe Gln Thr Arg Ser Asp
    50                  55                  60

Val Asp Val Leu Asp Asp Gly Tyr Lys Trp Arg Lys Tyr Gly Gln Lys
65                  70                  75                  80

Val Val Lys Asn Ser Leu His Pro Arg Ser Tyr Tyr Arg Cys Thr His

```
                         85                  90                  95
Asn Asn Cys Arg Val Lys Lys Arg Val Glu Arg Leu Ser Glu Asp Cys
                    100                 105                 110

Arg Met Val Ile Thr Thr Tyr Glu Gly Arg His Asn His Ser Pro Cys
                115                 120                 125

Glu Asp Ser Asn Ser Ser Glu His Glu Cys Phe Thr Ser Phe
            130                 135                 140

<210> SEQ ID NO 13
<211> LENGTH: 250
<212> TYPE: PRT
<213> ORGANISM: Oryza sativa

<400> SEQUENCE: 13

Met Tyr Ala Cys Met Glu Gly Ser Gln Leu Glu Thr Ala Cys Leu Pro
1               5                   10                  15

Ala Ala Leu Tyr Ala Pro Leu Cys Pro Tyr Thr Pro Ser Pro Pro
            20                  25                  30

Ser Phe Leu Ala Pro Leu Pro Ser Leu Gln His Lys Leu Pro Gln Leu
            35                  40                  45

Pro Gln Leu Val His Asp His Ala Ala Ala Thr Gly Thr Asn His Gly
        50                  55                  60

Val Met Phe Ser Ser Asp His Gly Cys Leu Tyr Pro Leu Leu Pro Gly
65                  70                  75                  80

Ile Pro Phe Cys Leu Asp Ser Gly Cys Gly Ala Ala Ala Cys Asp Asp
                85                  90                  95

Asp Lys Pro Ala Gly Phe Ala His Leu Gly Ser Ala Glu Ala Asp Thr
                100                 105                 110

Ser Ala Ala Ala Arg Val Asp Ser Glu Ile Ala Ala Ala Ala Thr
            115                 120                 125

Ala Thr Thr Cys His Gly Pro Asn Ser Trp Trp Lys Gly Thr Glu Lys
            130                 135                 140

Gly Lys Met Lys Val Arg Arg Lys Met Arg Glu Pro Arg Phe Cys Phe
145                 150                 155                 160

Gln Thr Arg Ser Asp Val Asp Val Leu Asp Asp Gly Tyr Lys Trp Arg
                165                 170                 175

Lys Tyr Gly Gln Lys Val Val Lys Asn Ser Leu His Pro Arg Ser Tyr
                180                 185                 190

Tyr Arg Cys Thr His Asn Asn Cys Arg Val Lys Lys Arg Val Glu Arg
            195                 200                 205

Leu Ser Glu Asp Cys Arg Met Val Ile Thr Thr Tyr Glu Gly Arg His
        210                 215                 220

Thr His Thr Pro Cys Ser Asp Asp Ala Thr Thr Gly Ala Ala Gly Asp
225                 230                 235                 240

His Thr Ala Ser Cys Ala Phe Thr Ser Phe
                245                 250

<210> SEQ ID NO 14
<211> LENGTH: 684
<212> TYPE: DNA
<213> ORGANISM: Medicago truncatula

<400> SEQUENCE: 14
atggatggag aaagagatgt tcccaattat gatctccaag tttcattcac aaataccct      60 caagctattc atgaaatggg ttttgttcaa tttgaagaaa tcaagttcct tagcttcttg    120
```

| | |
|---|---:|
| tcaccctcta cacaatccca accttctcaa ctttctcaat ctctaaattc cggccgtggc | 180 |
| accaccaacg ccactaccgg tgcagccgtc acaactacca ccgtggctgc tgggtttagc | 240 |
| cataatgatc ttgtcactac tagaactcct tggaacaatg aacaggtgag aactctagat | 300 |
| cccaaagctg tgagtgatga aattgcact ggaaatacta gtgatggcaa caacacatgg | 360 |
| tggaggagtg gaggagcaga aagagcaag gtgaaagtga ggaggaaact tagagagcca | 420 |
| aggttttgtt tccagacaag aagtgatgta gatgtgcttg atgatggtta caaatggagg | 480 |
| aagtatggtc aaaaagttgt caagaatagt cttcatccaa gaagttatta tcgttgcaca | 540 |
| cataacaatt gtcgggtgaa aaaaagagtt gaacgactct cagaagattg tcgtatggta | 600 |
| ataaccactt atgaaggcag acacaatcac tctccttgtg acgactctaa ttcttctgaa | 660 |
| cacgaatgtt ttacgtcttt ttga | 684 |

<210> SEQ ID NO 15
<211> LENGTH: 684
<212> TYPE: DNA
<213> ORGANISM: Medicago sativa

<400> SEQUENCE: 15

| | |
|---|---:|
| atggatggag aaagagatgt tcccaattat gatctccaag tttcattcac aaataccctct | 60 |
| caagctatcc atgaaatggg ttttgttcaa tttgaagaaa atcaagttct tagcttcttg | 120 |
| tcaccctcta cacaatccca accttctcaa ctttctcaat ctctaaattc cggccgtagc | 180 |
| accaccaacg ccactaccgg tgcagccgtc acaactacta ctgtggctgc cggatttagc | 240 |
| cataatgatc ttgtcactac tagaactcct tggaacaacg aacaggtgag aactctagat | 300 |
| cccaaagctg tgagtgatga aattgcact ggaaatacta gtgatggcaa caacacatgg | 360 |
| tggaggagtg gaggagcaga aagagcaag gcgaaagtga ggaggaaact tagagagcca | 420 |
| aggttttgtt tccagacaag aagtgatgta gatgtgcttg atgatggtta caaatggagg | 480 |
| aagtatggtc agaaagttgt caagaatagc cttcatccaa gaagttatta tcgctgcaca | 540 |
| cataacaatt gtcgggtaaa aaaaagagtt gaacgactct cagaagattg tcgtatggtg | 600 |
| ataaccactt atgaaggcag acataatcac tctccttgtg acgactctaa ttcttctgaa | 660 |
| cacgaatgtt ttacctcttt ttga | 684 |

<210> SEQ ID NO 16
<211> LENGTH: 657
<212> TYPE: DNA
<213> ORGANISM: Arabidopsis thaliana

<400> SEQUENCE: 16

| | |
|---|---:|
| atggaaggag gagggagaag agtattcagt aattacgatc tacaacaagt gacatcgtcg | 60 |
| tcgacgacga ttcaagagaa tatgaacttc ctcgttcctt ttgaagaaac caatgtctta | 120 |
| acctttttct cttcttcttc ttcctcttct ctttcttctc cttctttccc cattcacaac | 180 |
| tcttcctcca ctactactac tcatgcacct ctagggtttt ctaataatct tcagggtgga | 240 |
| ggacccttgg gatcaaaggt ggttaatgat gatcaggaga attttggagg tggaactaac | 300 |
| aatgatgctc attctaattc ttggtggaga tcaaatagtg gaagtggaga tatgaagaac | 360 |
| aaagtgaaga taaggaggaa actaagagag ccaagattct gtttccaaac caaaagcgat | 420 |
| gttgatgttc ttgacgatgg ctacaaatgg cgtaaatatg gtcagaaagt cgtcaagaac | 480 |
| agccttcacc ccaggagtta ttacagatgc acacacaaca actgtagggt gaaaagagaa | 540 |
| gtggagcgac tatcggaaga ttgtagaatg gtgattacta cttacgaagg tcgtcacaac | 600 |

```
cacattccct ctgatgactc cacttctcct gaccatgatt gtctctcttc cttttaa      657
```

<210> SEQ ID NO 17
<211> LENGTH: 618
<212> TYPE: DNA
<213> ORGANISM: Populus trichocarpa

<400> SEQUENCE: 17

```
atggatcatg gagaaagaga tgttccaaat tacgagctac atgtctcttt ctcaacacca   60
caagcaatcc atgagatggg ttttgttcaa tttgaagaaa accaggtctt gagcttcctg  120
gccccttcac aatcttctca gatatctcag cctctaaatg ctaatactac acaaccaac   180
aatactcaca tggggtttag tcataatgac cagcaggtgg gagcattgga tccaaaggct  240
tctagtgatg agaactgcac tggtaatgct aacaacgatg caacaattc atggtggagg   300
agctcatccg cagacaagaa caagttgaaa gtgaggagaa agcttagaga accaagattt  360
tgttttcaaa caaggagtga agtggatgtt cttgatgatg ttataaatg gaggaaatat   420
ggccagaaag ttgtcaaaaa cagccttcat ccaagaagct actatcgttg tactcacaac  480
aactgtcgag tcaagaagag ggttgaaaga ttatcagagg attgtcgaat ggtgataaca  540
acttatgaag gtagacacaa tcactctcca tgtgatgatt ccaattcatc agaacatgaa  600
tgttttcct ctttctaa                                                 618
```

<210> SEQ ID NO 18
<211> LENGTH: 687
<212> TYPE: DNA
<213> ORGANISM: Vitis vinifera

<400> SEQUENCE: 18

```
atggatcatc atcatcatca aggagaaaga tctggggttc aaattatga gcttcaggtg    60
tcttattcta ctactcctca aggcatccat gaaatggggt ttgtgcagtt tgaggagaac  120
caggtgctga gtttcttggc accatcacag tctgctcaga tgtctcagcc tctcaacact  180
gctagcacat ccacacccac acccacaccc accaacacca ctactaatac aaccatgggc  240
tttactcaca atgatcttct caccagacct tcttggaata tgagcaggt ggggacattg   300
gatccgaagg ctgtgaatga agagaattgc actggtaatg ccaacgatgg aagcaattca  360
tggtggagga gctcatcctc agaaaagacc aaagtgaagg cgaggagaaa gcttagagag  420
ccaaggttct gttttcaaac tagaagcgag gtggatgtgc tcgacgatgg ttacaaatgg  480
agaaaatatg gccagaaagt cgtcaagaat agccttcatc caagaagtta ttatcgttgt  540
actcatacaa actgtcgagt gaagaagagg gtggagcggt tatcagaaga ttgtcggatg  600
gtgataacaa catatgaagg tagacacaac cactctcctt gtgacgactc caattcatct  660
gaacacgaat gtttcacttc attctga                                      687
```

<210> SEQ ID NO 19
<211> LENGTH: 678
<212> TYPE: DNA
<213> ORGANISM: Glycine max

<400> SEQUENCE: 19

```
atggaagcag agagaggtgg tgcacccaat tatgagcttc aagtttcgtt caccaacacc   60
ccacaagcct tacgaaat gggttttgtt caatatgaag aaaaccaggt ccttggcttc    120
ttgtcaccct cttcacaatc tcaatcttct cacctctctc aatccttaaa tagtgatact  180
```

```
ggcgttgttg ctgtcactgc cacgacccccc accgcaacca tcggattcat gagtcatagc      240
ggacttgtca cgaaaacttg gaataacgac caggtaggaa ctctggatcc aaagcctgtc      300
gaagatgaaa attgcactgg aaatggtagt gatcaaggca caacaacac ttggtggagg        360 agcgcagcta cagagaagaa caaggtgaaa ataaggagga agcttagaga accaaggttt      420
tgttttcaaa caagaagtga tgtagatgtg cttgatgatg gttacaaatg gaggaaatat      480
ggccagaaaa ttgtcaagaa tagccttcat ccaagaagtt attaccgctg cacgcacaac      540
aactgtaggg tgaagaagag ggttgaacga ctctcagagg attgtcgtat ggtgataacc      600
acctatgaag gtagacacaa tcactcccct tgcgacgact caaattcatc agagaatgaa      660
tgctttacct ctttctag                                                    678

<210> SEQ ID NO 20
<211> LENGTH: 615
<212> TYPE: DNA
<213> ORGANISM: Sorghum bicolor

<400> SEQUENCE: 20
agcagccaaa acaagctttt ccagatgccg tttgtagttg accaggaagc agagaccgaa       60
aaccatggcg gcggcgggat gctctcctcc gaccattgtg gactataccc gctgccggca      120
ctgcccttcg gcagctgctc cggtgccgcc ggcgccgcaa cagcgtgcgg tgggaagcct      180
acggccggtt tcatgcccag tgctattgtc gctgaggagg tctgcacctc ggtgactact      240
aaattaggtt gcaacgacag taatggcaca tggtggaagg gttcggcagc tacaacgata      300
gcggagagag ggaagatgaa ggtgaggagg aagatgaggg aaccgaggtt ttgcttccag      360
accagaagcg acgtggatgt actggatgat ggctacaagt ggaggaagta tgggcagaag      420
gttgtcaaga acagcctcca tccaaggagc tatttccggt gcactcacag caactgccgc      480
gtgaagaaac gggtggagcg gctgtcgacg gactgccgca tggtgatgac cacgtacgag      540
ggccgccaca cgcactctcc ctgcagcgac gacgcttcct ccgccgacca caccgattgc      600
ttcacctcct tctga                                                      615

<210> SEQ ID NO 21
<211> LENGTH: 639
<212> TYPE: DNA
<213> ORGANISM: Oryza sativa

<400> SEQUENCE: 21
atgcctcttc ctcctccact tcaactaccg tgccatccga agctactcca gatgccattc       60
gaccaagaag atcagcccgg aatccatggc gtgatgctct cttctgacca ctgcgggctg      120
taccctctgc cggcgcttcc gttaagcaac tccgccgccg ccgccgccgc aaccgtcgca      180
ttggggaagc acagtgcagc cgccggttcc atgcccaata ttggcggcgc tgaggaggtg      240
gccaccactg taaccaaagc tggcaatgag agtactactt gcaatggctc cactacatgg      300
tggaggggct cgacgatggc ggcgatgggg gagaagggga agatgaagat caggaggaag      360
atgagggagc cgaggttctg cttccagacc agaagcgaag tggatgtgct ggatgacggg      420
tacaagtgga ggaagtacgg acagaaggtt gtcaagaaca gtctccatcc caggagctac      480
ttcaggtgca cgcacagcaa ctgccgcgtg aagaagcggg tggagcggct gtcgacggac      540
tgccgcatgg tgatcaccac ctacgagggc cgccacacgc actcccctg cgacgacaac       600 tcctccggcg agcacaccaa ctgcttcagc tccttctga                             639
```

<210> SEQ ID NO 22
<211> LENGTH: 690
<212> TYPE: DNA
<213> ORGANISM: Triticum aestivum

<400> SEQUENCE: 22

| | | |
|---|---|---|
| atggaagggg gtagccagct gggggcgtgc cttcccagcc tctacgcgct cgatccgtac | 60 |
| gcatcccctc ccctcctcgc tccattgccg aaccagcaca agcttcacca gctgccgctg | 120 |
| gtgctccaag agcagccagg gaaccacggc gtgatgttct cctcggacca tggcggaggc | 180 |
| ctgtacccgc tgcttccggg gatccccttc tgccactccg ccgccgcctg cgagaagtcc | 240 |
| accgggttcg cgcccttggg cggcaccggc gaggcgggca tcggcggc cagagcgggc | 300 |
| aacgagtttg ctagtgctac tactaccacc acagccagct gccatggtcc gagctcatgg | 360 |
| tggaaggggg cggagaaggg aaagatgaag gtgaggagga agatgaggga gccgcggttc | 420 |
| tgcttccaga ccaggagcga agtggacgtg ctggacgacg atacaagtg gaggaagtac | 480 |
| ggccagaagg ttgtcaagaa cagccttcat cccaggagct actaccggtg cacccacagc | 540 |
| aactgccgcg tgaagaagcg tgtggagcgg ctgtcggagg actgccgcat ggtgatcacc | 600 |
| acctacgaag ccgccacac ccacaccccc tgcagcgacg acgacgccgg cggcgaccac | 660 |
| acgggcagct gcgccttcac ttccttctga | 690 |

<210> SEQ ID NO 23
<211> LENGTH: 855
<212> TYPE: DNA
<213> ORGANISM: Zea mays

<400> SEQUENCE: 23

| | | |
|---|---|---|
| atgccccca ataccacttt gacccacccc atcgatcaat tgatcaccac cacaacccac | 60 |
| accccgcacg gtcgatctat cttgttatat gcgtgcatgg aggggagcag cagccagctg | 120 |
| ctggagacct gccttcctgc tagcctctac gcggttactc ctcctccatg cgcccatcct | 180 |
| catcccttc ttgccccgct gccgaaccag cagcacatgc ttctgcagat gccgtttgtc | 240 |
| aaggagcagg ctgcgaataa tcatggcctg atgctctctt cggaccacca ccaccacagc | 300 |
| ggcctcctgt acccgctgct tcttcccggc atcccttctt gcccctccgt cgccgccgcc | 360 |
| tgcgagaaga ctaccaccac cggctccggg gcgctcgatg ccggcgaggc gggcaccagc | 420 |
| tcggcggcgg cgaaagccac cggcgagatc gctagtaccg ccgccaccgc atgcaacagc | 480 |
| ccaagttcct gcaattggtg aagggcccg gcggcggcag cagcggggga gaaaggagga | 540 |
| cggatgaagg tgaggaggaa gatgagggaa ccgaggttct gcttccagac aaggagcgac | 600 |
| gtggatgtgc tggacgacgg ctacaagtgg agaaagtacg ccagaaggt tgtcaagaac | 660 |
| agcctccatc caaggagcta ctaccggtgc acccacagca actgccgcgt gaagaagcga | 720 |
| gtggagaggc tatcggagga ctgccgcatg gtgatgacca cctatgaggg tcgccacacg | 780 |
| cactcccct gcagcgacga cgccgacgcc ggcggcggcg atcacactgg cagctgcgct | 840 |
| ttcacgtcgc tctag | 855 |

<210> SEQ ID NO 24
<211> LENGTH: 747
<212> TYPE: DNA
<213> ORGANISM: Sorghum bicolor

<400> SEQUENCE: 24

| | | |
|---|---|---|
| atggagggga gcagccagct gttggagacc tgccttcctg ctagtagcct ctacgcgctc | 60 |

| | |
|---|---|
| agtccgcatc atcctcttct tgccccgctg ccgaaccagc acaagcttct gcagatgccg | 120 |
| ttggtccagg agcaggctgc tgcgaataat catggcgtga tgctctattc ggaccaccac | 180 |
| caccacggcg gcggcctcct gtacccgctg cttcttcccg gcatcccgtt ctgccccttc | 240 |
| tccgccgccg ccgacgccgc cacctgcgat aagaccacca ccaccggcgg cttcgcggcg | 300 |
| ctcgatgccg gcgaggcggg cacctcagtg gcgaaagccg ccggcgagat cgctagtacc | 360 |
| accaccacat gcaacggccc aagttcctgc aattggtgga agggcccggc ggcggcgggg | 420 |
| gagaaaggcg gacggatgaa ggtgaggagg aagatgaggg aacccaggtt ctgcttccag | 480 |
| accaggagcg acgtggatgt gctggacgac ggctacaagt ggaggaagta cggccagaag | 540 |
| gttgtcaaga acagcctcca tccaaggagc tactaccggt gcacccacag caactgccgc | 600 |
| gtgaagaagc gagtggagag gctgtcggag gactgccgca tggtgatcac cacctacgag | 660 |
| ggccgccaca cgcactcccc ctgcagcgac gacgccgacg ccgccgccgg cgaccacact | 720 |
| ggcagctgcg ctttcacgtc gctctag | 747 |

<210> SEQ ID NO 25
<211> LENGTH: 429
<212> TYPE: DNA
<213> ORGANISM: Populus balsamifera subsp. trichocarpa

<400> SEQUENCE: 25

| | |
|---|---|
| atggggttta gtcataatga tgagcaggtg gggacaatgg atccaaagcc ttccagtgac | 60 |
| gagaactgca ctggtaatgc taacaacgat ggcaacaatt catggtggag gagctcatcc | 120 |
| tcagagaaaa acaggttgaa agtgaggaga aagcttagag aaccaaggtt ttgtttccag | 180 |
| acaaggagcg atgtggatgt tcttgatgat ggttataagt ggagaaaata tggccaaaaa | 240 |
| gttgtcaaaa acagccttca tccaagaagc tactatcgtt gtactcacaa caactgtcga | 300 |
| gtgaagaaga gggttgaaag attatcagag gattgtcgaa tggtgataac aacctatgaa | 360 |
| ggcagacaca atcactctcc atgcgaggac tcaaattcat cagaacatga gtgctttacc | 420 |
| tctttctaa | 429 |

<210> SEQ ID NO 26
<211> LENGTH: 753
<212> TYPE: DNA
<213> ORGANISM: Oryza sativa

<400> SEQUENCE: 26

| | |
|---|---|
| atgtatgcgt gcatggaagg gagccagttg gagacggctt gcctccctgc cgcgctctac | 60 |
| gcgccgctct gcccgtacac gccgccttcc cctccttcct ttcttgcgcc attgccgagc | 120 |
| ctgcagcaca agcttcccca gctgccgcag ctggtccacg accacgccgc cgccaccggg | 180 |
| acgaaccatg gcgtgatgtt ctcgtcggac catggctgcc tgtacccgct gctcccgggg | 240 |
| atcccgttct gcctcgactc cggctgcggc gccgccgcct cgacgacgac aagcccgcc | 300 |
| ggtttcgcgc acttgggctc cgccgaggcg gacacatcgg cggcggcggc gagagtggat | 360 |
| agcgagattg ctgcagctgc caccgcaacc acttgccatg gcctaattc atggtggaag | 420 |
| gggacggaga aggggaagat gaaggtgagg aggaagatga gggagccgag gttctgcttc | 480 |
| cagaccagga gcgatgtgga tgtgctggac gacggctaca gtggaggaa gtatggccag | 540 |
| aaggttgtca agaacagcct ccacccaagg agctactaca ggtgcaccca caacaactgc | 600 |
| cgcgtgaaga agcgggtgga gcggctgtcg gaggattgcc gcatggtgat caccacctac | 660 |
| gagggccgcc acacccacac ccctgcagc gacgacgcca ccaccggcgc cgccggcgac | 720 |

```
cacaccgcca gctgcgcctt cacctccttc tga                                753
```

<210> SEQ ID NO 27
<211> LENGTH: 7
<212> TYPE: PRT
<213> ORGANISM: Artificial
<220> FEATURE:
<223> OTHER INFORMATION: consensus sequence

<400> SEQUENCE: 27

Trp Arg Lys Tyr Gly Gln Lys
1               5

<210> SEQ ID NO 28
<211> LENGTH: 668
<212> TYPE: DNA
<213> ORGANISM: Medicago truncatula
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t

<400> SEQUENCE: 28

```
cgataaagaa tagttttcaa gaaaaacatt ccctttagaa ttccattgga gagaataaaa     60
ctcttagttg accaaactat acacacaaac cctcacatgt catagaattt gtatgtgcta    120
ttagaagatc aagctaagct agcaagcata aagtaacaa aaagaaaaga aaaaaaaatc     180
aaaagctagc taagatattc caaatccaat ttaggatttt tatttcataa aaaaaaggga    240
tatggatgga gaaagagatg ttcccaatta tgatctccaa gtttcattca caaatacccc    300
tcaagctatt catgaaatgg gttttgttca atttgaagaa aatcaagttc ttagtttctt    360
gtcaccctct acacaatccc aaccttctca actttctcaa tctctaaatt ccggccgtgg    420
caccaccaac gccactaccg gtgcagccgt cacaactacc accgtggctg ccgggtttag    480
ccataatgat cttgtcacta ctagaactcc ttggaacaat gaacaggtga gaactctaga    540
tcccaaagct gtgagtgatg agaattgcac tggaaatact agtgatggca acaacacatg    600
gtggaggagt ggaggagcan aaaagagcaa ggtgaaagtg angaggaaac ttagagagcc    660
aaggtttt                                                            668
```

<210> SEQ ID NO 29
<211> LENGTH: 684
<212> TYPE: DNA
<213> ORGANISM: Medicago truncatula

<400> SEQUENCE: 29

```
atggatggag aaagagatgt tcccaattat gatctccaag tttcattcac aaatacccct     60
caagctattc atgaaatggg ttttgttcaa tttgaagaaa atcaagttct tagcttcttg    120
tcaccctcta cacaatccca accttctcaa ctttctcaat ctctaaattc cggccgtggc    180
accaccaacg ccactaccgg tgcagccgtc acaactacca ccgtggctgc tgggtttagc    240
cataatgatc ttgtcactac tagaactcct tggaacaatg aacaggtgag aactctagat    300
cccaaagctg tgagtgatga gaattgcact ggaaatacta gtgatggcaa caacacatgg    360
tggaggagtg gaggagcaga aagagcaag gtgaaagtga ggaggaaact tagagagcca    420
aggttttgtt ccagacaag aagtgatgta gatgtgcttg atgatggtta caaatggagg    480
```

```
aagtatggtc aaaaagttgt caagaatagt cttcatccaa gaagttatta tcgttgcaca      540
cataacaatt gtcgggtgaa aaaaagagtt gaacgactct cagaagattg tcgtatggta      600
ataaccactt atgaaggcag acacaatcac tctccttgtg acgactctaa ttcttctgaa      660
cacgaatgtt ttacgtcttt ttga                                             684

<210> SEQ ID NO 30
<211> LENGTH: 4225
<212> TYPE: DNA
<213> ORGANISM: Medicago truncatula

<400> SEQUENCE: 30
atggatggag aaagagatgt tcccaattat gatctccaag tttcattcac aaataccoct       60 caagctattc atgaaatggg ttttgttcaa tttgaagaaa atcaagttct tagcttcttg      120
tcaccctcta cacaatccca accttctcaa ctttctcaat ctctaaattc cggccgtggc      180
accaccaacg ccactaccgg tgcagccgtc acaactacca ccgtggctgc tgggtttagc      240
cataatgatc ttgtcactac tagaactcct tggaacaatg aacaggtggt ttaatttatt      300
tcttttatta ttatgaaaaa aatgaaatat ctttctttgc tgcaatttt ttttttctat      360 atgaaatatc cgatcaaatt aacatcaat tgaagtttat attataatct aaaacttcat      420
aattaatttg tgagtttttt ttctttcctg tatgtctaat tatttagtta ttagtaattg      480
atttactaat tctatgaatg ataaaaaaag aaaatatat gaatgataca attgaagcta      540
aaactatgat attcaagttt atgattaatt tgtgagtttt tttctttaat tgtaattatt      600
tagttagttg tgtgatgtta tgtccttttc aatgttaggg tattgttttc atatctattc      660
attaagatga taatgatgat gaatatatta atgatgtgga tgatacaatg aatgaatcaa      720
acttttgtga attcttgatc aggtgagaac tctagatccc aaagctgtga gtgatgagaa      780
ttgcactgga aatactagtg atggcaacaa cacatggtag ctccaaaagt taattgccaa      840
tttcaatgtt tttttttctt ctctttctta aagtgcatg cacgtaatag acttcatata      900
tatttcactc aaacaaatca tgttcacttt ttctttcttt actaatttga agccattttg      960
ggatcatatt tattttggtt ttttatttga agactcgtat aatatattaa ttaataatgt     1020
cttaagctaa ttagaaaaaa agaatcatgt tgatttgtat gatgataggt ggaggagtgg     1080
aggagcagag aagagcaagg tgaaagtgag gaggaaactt agagagccaa ggttttgttt     1140
ccagacaaga agtgatgtag atgtgcttga tgatggttac aaatggagga agtatggtca     1200
aaaagttgtc aagaatagtc ttcatccaag gtaattaatc cttcattcat attattcttg     1260
cttaattaat ctcttcatta aaaatatatt tctatatttc aaatatgtta tgattatcac     1320
gtataatata taggttaata ttaaccacgg ttgaacggaa gttgttaaat ttcgattaaa     1380
attgtttgaa agaatctgaa ttgaacctca ctaaaacgat cgttagtcag actttaaaat     1440
tataccaagc ttcatttctc ttcaaaagtg gagagttaag aaaaaattaa atatagtaga     1500
ttgtactaga ttatatatat atatatatat atatatccat tagtgagaat tttactccta     1560
tttttggcat ttttctctta ctaaaaaaaa caattaattt gtttaaagtt ggtaaaaatc     1620
atatcacaaa acaaaaaagt agttcagtat tcagacacct ccgaattgta acgttgaaaa     1680
accaaatcac tgtttgaatt tataatggac aaccaaaaaa aagaaacac ccatctcttt     1740 gaaagatgaa ggagaagaga agagtagtat gtgtgattat ttggtgtagt atttgaaaat     1800
ggaaaatgtt atttctctag aaaaatagca tcaaattttc aagacgctgg tgacaaattt     1860
```

```
taattgaatt ttctattttt gagccaaacc taagtttcag gtgaaaatgt taaatccata    1920
ttataatgaa gtacatggct acatcaaagg cattataccc ggagaaatga aggtagaatg    1980
tcttttttgg gaaaaataag ggtgtcggta gtcaacaaaa ctaaataaat attcctcaca    2040
actagagaga gatagagaga gagaatctct tcagctaaaa ctgaagaaag gaatgatcaa    2100
gatgtttact ttcgagagag agagagagag agaatctctt cagctatagt gaagattgat    2160
ggtacagact gagcattggg cttattttca gacaaaatat tgattggaga aaaataaaga    2220
tattattggt tagaatatat atgttatatg tatatctcta gtggatataa ttagtatagt    2280
tttgacaata gagcacacta tagggtcccc tctttccttt cctttgtcct atgtgtgtac    2340
ataaatgttc ccaaaacacc caacttcttt cacttaatcc tagcggttta attaatgaaa    2400
tttgtgtgca tgcatgatgt gcactaatca tcatttagga aaatatttct tatacactcc    2460
aaatatgctt atatatatct tgagagatat atatgatttg ataggagaca tgctaaataa    2520
aacaaatgtt tagtatagta tagtaagatg aaaaccaaag ttacttagac ttaagggaag    2580
ggaactaata attaagggaa agaaaaacat tgtcaaccat tatttacgaa aaaaaaagat    2640
catcacataa catgtgtgtt gatattgtta cgttcattga agaaagttta atagtttact    2700
ttggaagtac ttaacgaacc aatacaaagt ggttgaagtg ctatatgctt tacaattatt    2760
aaaccaaaga aattgttcgt aaatttgctt cagttgtaga ccaccattgc aagattgtac    2820
ttaaagatat gtacttagaa gtggaattag gagtttactc aaatgatcat tacatgaaca    2880
tatatatagg agttcagaga ctagcaagta acacacgaga aaacttttta tgaagaagag    2940
attgatgacc aaacttacaa tatattgaga ttaaattaat aagccaagtt ccctcagaaa    3000
gaaaaaaaaa aactaatcat ttatttatag atcattgtac catgtagtaa ataccctgtt    3060
gaattattat tgaggagtgc cagcaatata aacaacatta ttcaaaaaat atactataca    3120
tttattcatt tatatatcat tataccatgt aaatacctgt taaataatta atgaggactg    3180
tcatcgttta attattaaat gacatgttat attttttatat taattttattt aaaagttaaa    3240
ttaaattttg aaatgacttt tgcctacgaa gttgctcata tttaaaaatt gaacatttt     3300
tacatggatt tcaatcaaat tatgcaggtc tcgaataaat ttgatgagac tatgaatcat    3360
ctcttttata tatctaatat tttattcatt cataggtgat ataagacata atcactcaca    3420
aatttaacca ctcacacttg aaacttaaca attctcccat ttgaatcaaa ttatgtagac    3480
cccatataaa tttaatgaga ctatatggat catctctttt atgtaaccaa tattttactc    3540
attcataggt gatataagac ttaatcactc acaaatttaa tgactcacac ttgaaactta    3600
tcaatctctc ccataagtgt gagttctcag cccggagaca agacccaaca caagatccac    3660
tcttactctc ccaccaagtg gaaccagggt tttgatacca cttgttggag agttaggggg    3720
cacgggagaa acaactaaca caaatgctca atgatctcaa gagagtgaga tgttacatct    3780
ccacttaaaa ctttaaaaca tttgatatat gaatcaaata tcttatatat ccaatattta    3840
ctcattcata gacgatgtga tgatatttaa tcactcacac ttgaaaccaa tatatgtgca    3900
ttgagatttc atgcatgatg catcatgcat gtctttaaat atgctttatt tcagctatt    3960
atttgttag gaatatttcc gttatttatt tattttggt tacataattc cgttatttat    4020
tagtactata ctaattaatt atttacatgt tattatatgc agaagttatt atcgttgcac    4080
acataacaat tgtcgggtga aaaaagagt tgaacgactc tcagaagatt gtcgtatggt    4140
aataaccact tatgaaggca gacacaatca ctctccttgt gacgactcta attcttctga    4200
acacgaatgt tttacgtctt tttga                                          4225
```

<210> SEQ ID NO 31
<211> LENGTH: 30
<212> TYPE: DNA
<213> ORGANISM: Artificial sequence
<220> FEATURE:
<223> OTHER INFORMATION: Synthetic primer

<400> SEQUENCE: 31
tccttgttgg attggtagcc aactttgttg                                      30

<210> SEQ ID NO 32
<211> LENGTH: 24
<212> TYPE: DNA
<213> ORGANISM: Artificial sequence
<220> FEATURE:
<223> OTHER INFORMATION: Synthetic primer

<400> SEQUENCE: 32
agttggctac caatccaaca agga                                            24

<210> SEQ ID NO 33
<211> LENGTH: 23
<212> TYPE: DNA
<213> ORGANISM: Artificial sequence
<220> FEATURE:
<223> OTHER INFORMATION: Synthetic primer

<400> SEQUENCE: 33
atggatggag aaagagatgt tcc                                             23

<210> SEQ ID NO 34
<211> LENGTH: 24
<212> TYPE: DNA
<213> ORGANISM: Artificial sequence
<220> FEATURE:
<223> OTHER INFORMATION: Synthetic primer

<400> SEQUENCE: 34
tcaaaaagac gtaaaacatt cgtg                                            24

<210> SEQ ID NO 35
<211> LENGTH: 27
<212> TYPE: DNA
<213> ORGANISM: Artificial sequence
<220> FEATURE:
<223> OTHER INFORMATION: Synthetic primer

<400> SEQUENCE: 35
tgtaatcatt gttgcatgga attcatc                                         27

<210> SEQ ID NO 36
<211> LENGTH: 34
<212> TYPE: DNA
<213> ORGANISM: Artificial sequence
<220> FEATURE:
<223> OTHER INFORMATION: Synthetic primer

<400> SEQUENCE: 36
agcggatcct gtaacgacta gacgtaaact taac                                 34

<210> SEQ ID NO 37
<211> LENGTH: 24
<212> TYPE: DNA
<213> ORGANISM: Artificial sequence
<220> FEATURE:

```
<223> OTHER INFORMATION: Synthetic primer

<400> SEQUENCE: 37
caccatggaa ggaggaggga gaag                                              24

<210> SEQ ID NO 38
<211> LENGTH: 22
<212> TYPE: DNA
<213> ORGANISM: Artificial sequence
<220> FEATURE:
<223> OTHER INFORMATION: Synthetic primer

<400> SEQUENCE: 38
aaaggaagag agacaatcat gg                                                22

<210> SEQ ID NO 39
<211> LENGTH: 27
<212> TYPE: DNA
<213> ORGANISM: Artificial sequence
<220> FEATURE:
<223> OTHER INFORMATION: Synthetic primer

<400> SEQUENCE: 39
caccatggat ggagaaagag atgttcc                                           27

<210> SEQ ID NO 40
<211> LENGTH: 24
<212> TYPE: DNA
<213> ORGANISM: Artificial sequence
<220> FEATURE:
<223> OTHER INFORMATION: Synthetic primer

<400> SEQUENCE: 40
ttattggaac gacattgttg gatc                                              24

<210> SEQ ID NO 41
<211> LENGTH: 49
<212> TYPE: DNA
<213> ORGANISM: Artificial sequence
<220> FEATURE:
<223> OTHER INFORMATION: Synthetic primer

<400> SEQUENCE: 41
aaagagacca ttagtatatt tgacccaaaa aaaataaaa aaaaaagag                    49

<210> SEQ ID NO 42
<211> LENGTH: 37
<212> TYPE: DNA
<213> ORGANISM: Artificial sequence
<220> FEATURE:
<223> OTHER INFORMATION: Synthetic primer

<400> SEQUENCE: 42
tggaagatgc atgttattga ctaaatatga tctacca                                37

<210> SEQ ID NO 43
<211> LENGTH: 38
<212> TYPE: DNA
<213> ORGANISM: Artificial sequence
<220> FEATURE:
<223> OTHER INFORMATION: Synthetic primer

<400> SEQUENCE: 43
tggcttaaat catattgaca agacccatta aaaagagg                               38
```

TRANSCRIPTION FACTORS FOR MODIFICATION OF LIGNIN CONTENT IN PLANTS

CROSS-REFERENCE TO RELATED APPLICATIONS

This application claims the benefit of priority of U.S. Provisional Application Ser. No. 61/409,871, filed on Nov. 3, 2010, the disclosure of which is incorporated herein by reference in its entirety.

This invention was made with Government support under grant DE-PS02-06ER64304 awarded by the U.S. Department of Energy; grant 703285 awarded by the National Science Foundation (NSF), and grant DBI-0421683 awarded by the NSF Plant Genome Program. The Government has certain rights in the invention.

BACKGROUND OF THE INVENTION

1. Field of the Invention

The present invention relates generally to the field of agriculture and plant genetics. More particularly, it concerns genetically modified plants displaying modified cell wall composition, resulting in altered levels of lignin, cellulose, and/or hemicellulose.

2. Description of Related Art

A variety of fuels may also be produced from sugars and starches as well as from lignocellulosic based biomass which constitute the most abundant biomass on earth. However, the types of biofuels that can be efficiently produced from plant mass depend upon the content of component material such as lignin. Likewise, biomass content dictates the nutritional value of plant mass as animal feed.

The principal source of fermentable sugar in lignocellulosic biomass is cellulose. In typical lignocellulosic biomass used for ethanol production, cellulose accounts for between 35 to 50% of the mass. Cellulose is a long chain polysaccharide carbohydrate, composed of repeating cellobiose ($\beta$-1,4 glucose disaccharide) units. Hemicellulose also contributes to the fermentable sugar content of lignocellulosic biomass. It comprises about 20 to 35% of lignocellulosic biomass mass, and is a mixture of a variety of sugars including arabinose, galactose, glucose, mannose, and xylose, and derivatives of such sugars. The third major component of lignocellulosic biomass, lignin, is not a sugar based fermentable polymer. Lignin is a complex polymer of hydroxylated and methoxylated phenylpropane units, linked via oxidative coupling and comprises about 12 to 20% of lignocellulosic biomass.

SUMMARY OF THE INVENTION

In a first aspect, a nucleic acid molecule is provided, comprising a nucleic acid sequence selected from the group consisting of: (a) a nucleic acid sequence that hybridizes to the complement of one or more of SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; or a fragment thereof, under conditions of 1×SSC and 65° C.; (b) a nucleic acid sequence comprising at least 85% sequence identity to one or more of SEQ ID NO: 14; SEQ ID NO: 15; SEQ ID NO: 16; SEQ ID NO: 17; SEQ ID NO: 18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; and (c) the complement of (a) or (b); wherein the nucleic acid sequence is operably linked to a heterologous promoter sequence and wherein expression of the nucleic acid sequence in a plant comprising in its genome a sequence complementary to all or a portion of the nucleic acid sequence modulates the lignin, cellulose, hemicellulose, and/or xylan content of said plant. One embodiment of the invention provides such a nucleic acid molecule, wherein the DNA molecule comprises a nucleic acid sequence exhibiting at least 85%, 90%, 95%, 96%, 97%, 98% or 99% sequence identity to at least one of the nucleic acid sequences: SEQ ID NO: 14; SEQ ID NO: 15; SEQ ID NO: 16; SEQ ID NO: 17; SEQ ID NO: 18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; or a complement thereof. Such a nucleic acid molecule, wherein the heterologous promoter sequence is a developmentally-regulated, inducible, tissue-specific, constitutive, cell-specific, seed specific, or germination-specific promoter, is another embodiment of the invention.

Yet another embodiment comprises such a nucleic acid molecule, wherein expression of the nucleic acid molecule in a plant cell reduces the lignin content of pith cells of said plant. In a further embodiment, the nucleic acid sequence comprises the complement of a nucleic acid sequence according to (a) or (b). In yet another embodiment, expression of the nucleic acid molecule increases the lignin, cellulose, hemicellulose and/or xylan content of pith cells of a plant in which such expression occurs.

Another aspect of the invention provides a transgenic plant cell comprising the nucleic acid molecule sequence selected from the group consisting of: (a) a nucleic acid sequence that hybridizes to the complement of one or more of SEQ ID NO: 14; SEQ ID NO: 15; SEQ ID NO: 16; SEQ ID NO: 17; SEQ ID NO: 18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; or a fragment thereof, under conditions of 1×SSC and 65° C.; (b) a nucleic acid sequence comprising at least 85% sequence identity to one or more of SEQ ID NO: 14; SEQ ID NO: 15; SEQ ID NO: 16; SEQ ID NO: 17; SEQ ID NO: 18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; and (c) the complement of (a) or (b); wherein the nucleic acid sequence is operably linked to a heterologous promoter sequence and wherein expression of the nucleic acid sequence in a plant comprising in its genome a sequence complementary to all or a portion of the nucleic acid sequence modulates the lignin, cellulose, hemicellulose, and/or xylan content of said plant. A further embodiment comprises a transgenic plant or plant part comprising the nucleic acid molecule, including a transgenic plant cell comprising the nucleic acid molecule and a transgenic plant or plant part comprising the nucleic acid molecule. In particular embodiments of the invention, pith cells of the transgenic plant comprise a secondary cell wall. Another embodiment of the invention provides biofuel feedstock comprising the nucleic acid molecule.

Yet another aspect of the invention provides a method of increasing the level of lignin, cellulose, hemicellulose, or a xylan in a crop plant comprising down-regulating a WRKY transcription factor in the plant. In particular embodiments of this method, the crop plant comprises a reduced level of lignin relative to the wild type lignin level, prior to down-regulating a WRKY transcription factor in the plant. A plant produced by such a method, wherein the digestibility of forage or biomass produced from the plant is increased relative to digestibility of forage or biomass produced from an otherwise isogenic plant that displays a wild type level of lignin in the absence of a down regulated WRKY transcription factor represents another embodiment of the invention. Further, in certain embodiments, the plant is a dicotyledonous plant. In other embodiments, the plant is a monocotyledonous plant. In particular embodiments, the plant is selected from the group consisting of: switchgrass (*Panicum virgatum*), giant reed (*Arundo donax*), reed canarygrass (*Phalaris arundinacea*), Miscanthus x giganteus, Miscanthus sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover and other legumes, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, poplar, willow, and agave.

Another aspect of the invention is a method of decreasing the lignin content in a plant comprising expressing an WRKY transcription factor in the plant. In certain embodiments thereof, the digestibility of feed harvested or prepared from the crop is increased. Another embodiment provides a method of increasing the lignin content of pith cells of a plant comprising expressing a nucleic acid molecule according to the above in the plant. Further, the invention provides a method for producing a commercial product comprising: obtaining a plant of or a part thereof comprising the nucleic acid molecule comprising a nucleic acid sequence selected from the group consisting of: (a) a nucleic acid sequence that hybridizes to the complement of one or more of SEQ ID NO: 14; SEQ ID NO: 15; SEQ ID NO: 16; SEQ ID NO: 17; SEQ ID NO: 18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; or a fragment thereof, under conditions of 1×SSC and 65° C.; (b) a nucleic acid sequence comprising at least 85% sequence identity to one or more of SEQ ID NO: 14; SEQ ID NO: 15; SEQ ID NO: 16; SEQ ID NO: 17; SEQ ID NO: 18; SEQ ID NO:19; SEQ ID NO:20; SEQ ID NO:21; SEQ ID NO:22; SEQ ID NO:23, SEQ ID NO:24; SEQ ID NO:25, or SEQ ID NO:26; and (c) the complement of (a) or (b); and producing a commercial product therefrom. In certain embodiments, the commercial product is paper, paper pulp, ethanol, biodiesel, silage, animal feed or fermentable or gasifiable biofuel feedstock.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

BRIEF DESCRIPTION OF THE SEQUENCES

SEQ ID NO:1-13 WRKY Transcription factor encoded polypeptide sequences.
SEQ ID NO:14-26 WRKY Transcription factor DNA coding sequences.
SEQ ID NO:27 Consensus sequence.
SEQ ID NOs:28-40 Primer sequences.

DESCRIPTION OF ILLUSTRATIVE EMBODIMENTS

Stems of dicotyledonous plants consist of an outer epidermis, cortex, a ring of secondarily thickened vascular bundles and interfascicular cells, and inner pith parenchyma cells with thin primary walls. In monocotyledonous plants, these specific "rings" of tissue are replaced by an arrangement where the pith and cortex are essentially continuous, and the vascular elements are more irregularly dispersed throughout this ground tissue. Mutants of *Medicago truncatula* and *Arabidopsis thaliana* with secondary cell wall thickening in pith cells associated with ectopic deposition of lignin, xylan and cellulose are described herein. The mutations are caused by disruption of stem-expressed WRKY transcription factor genes encoding repressors of the NAC and C3H zinc finger transcription factors that activate secondary wall synthesis. The studies provided herein surprisingly demonstrate that an WRKY transcription factor ("TF") gene, such as the *M. truncatula* MtSTP plays a primary regulatory role in controlling secondary cell wall development in pith tissues. The present disclosure further demonstrates that lignification as well as biomass density may be modulated in plants with altered WRKY expression, for instance in both monocots (e.g. switchgrass and maize) and dicots (e.g. *Medicago* sp.). The discovery of negative regulators of secondary wall formation in pith tissues allows for increasing the mass of fermentable cell wall components in lignocellulosic bioenergy crops, since much of the biomass on the earth's surface is found in plant secondary cell walls.

Figure 2:
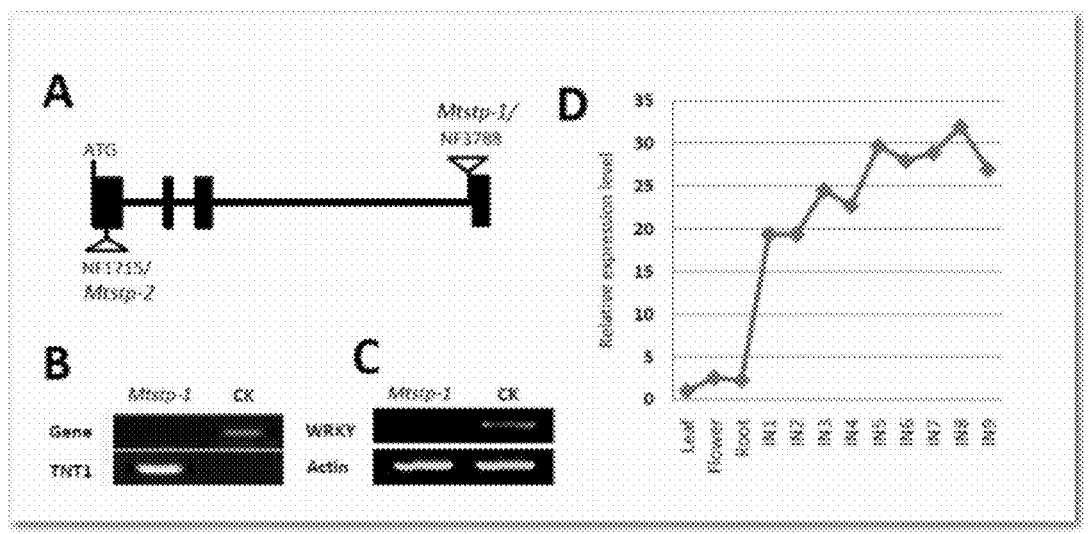
FIG. 2. Molecular cloning of MtSTP and alignment with homologous proteins. (A) MtSTP gene structure and Tnt1 insertion sites. (B) PCR identification of homozygotes of the Tnt1 insertion line; the wild-type plant has only a gene-specific band whereas the insertion line has only a T-DNA-specific band. (C) RT-PCR analyses of MtSTP transcript levels using primers covering the full length cDNA. ACTIN was used as control. (D) Real time PCR showing the expression of MtSTP in different organs (IN, internode), normalized against the expression of MtACTIN. (E) Alignment with homologous proteins. Black shading indicates identical amino acids. The conserved WRKY domain and C2H2 zinc finger motif are marked by a line and triangles, respectively. The following SEQ ID NOs correspond to the sequences shown in the alignment: *M. Truncatula* (SEQ ID NO:1); *Populus* (SEQ ID NO:4); *Glycine Max* (SEQ ID NO:5); *Vitis Vinifera* (SEQ ID NO:6); *Arabidopsis* (SEQ ID NO:3).
Figure 2:
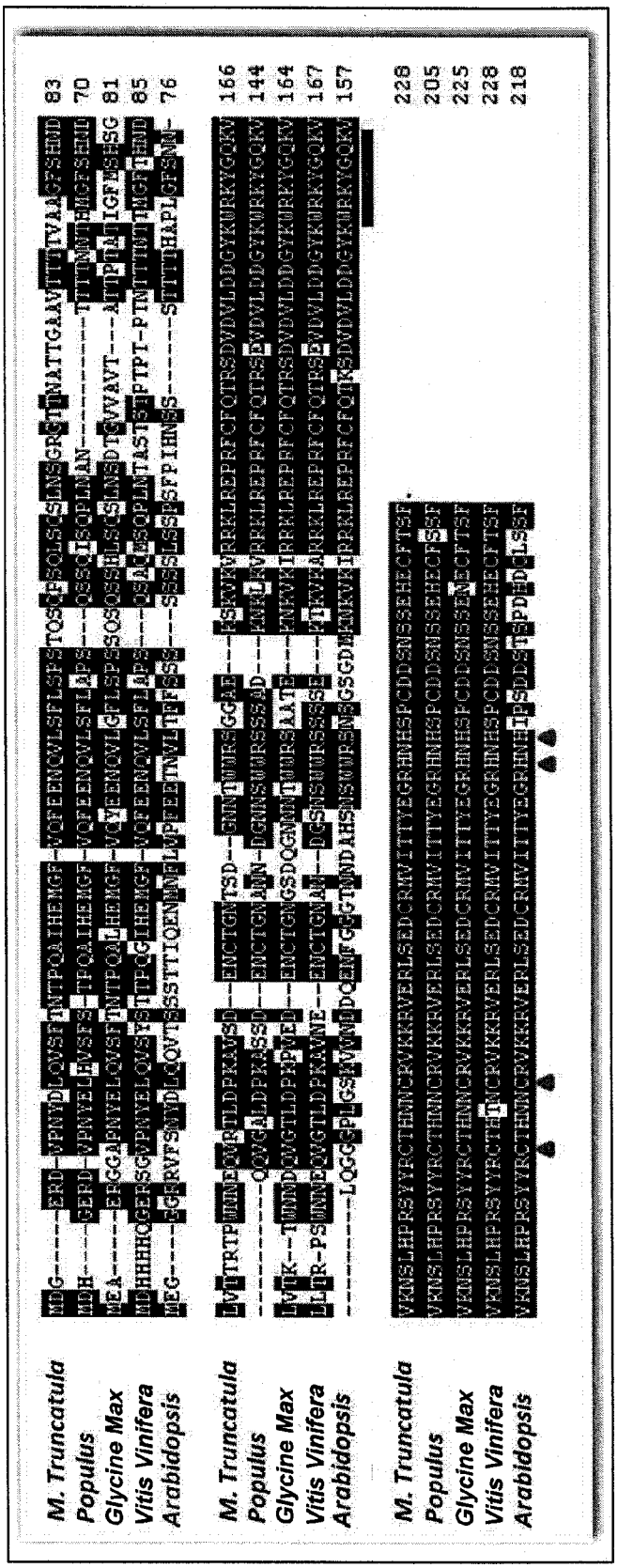
Figure 7:
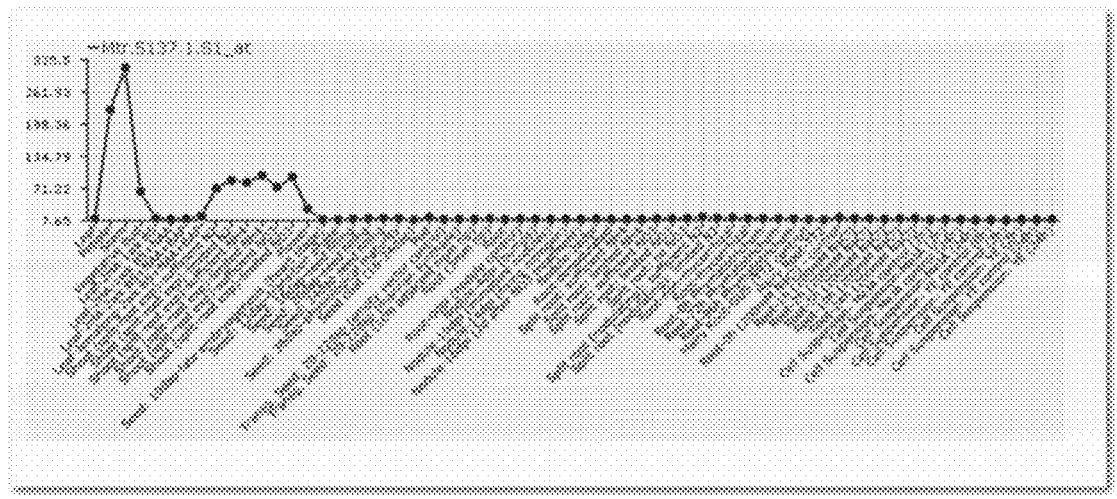
FIG. 7. Tissue-specific expression of the MtSTP gene, as determined by mining microarray data from the *Medicago* Gene Expression Atlas (Benedito et al., 2008).

MtSTP encodes a WRKY family TF that is preferentially expressed in stem internodes, where its expression level increases with maturity (FIG. 2D) but is not influenced by hormones or biotic or abiotic-stress (FIG. 7). Several related WRKY proteins (e.g. SEQ ID NOs: 1-13) were identified from *Populus trichocarpa*, *Vitis vinifera*, *Glycine max* and *Arabidopsis thaliana* (AtWRKY-12), among other plants. Each contains a conserved WRKYGQK (SEQ ID NO:27) motif and a C2H2 Zinc Finger sequence at the C-termini (FIG. 2E).

Potential applications of embodiments of the invention include, among others: (1) down-regulation of the WRKY gene in an otherwise wild type lignin content genetic background, to give increased lignin, cellulose and hemicelluloses, i.e more overall biomass and sturdier plants; (2) down-regulation of WRKY in a low lignin background, for increased biomass with better digestibility; (3) up-regulation of the WRKY TF to reduce lignin content in the plant.

In addition to increasing lignin in pith cells, knock-out of the MtSTP gene or a homolog thereof, a negative regulator of secondary cell wall development in the pith, also can result in large increases in hemicellulose and cellulose levels. Remarkably, the mutants have thick secondary cell walls in the central pith and increased biomass, whereas wild-type plants have thin primary walls. Therefore, manipulating this gene allows for an increase in the amount of lignocellulose in plants without significant apparent impact on plant growth and development.

I. Production of Ethanol from Lignocellulosic Biomass

The overall process for the production of ethanol from biomass typically involves two steps: saccharification and fermentation. First, saccharification produces fermentable sugars from the cellulose and hemicellulose in the lignocellulosic biomass. Second, those sugars are then fermented to produce ethanol. Additional methods and protocols for the production of ethanol from biomass are known in the art and reviewed in, for example, Wyman (1999); Gong et al., (1999); Sun and Cheng, (2002); and Olsson and Hahn-Hagerdal (1996).

A. Pretreatment

Raw biomass is typically pretreated to increase porosity, hydrolyze hemicellulose, remove lignin and reduce cellulose crystallinity, all in order to improve recovery of fermentable sugars from the cellulose polymer. As a preliminary step in pretreatment, the lignocellulosic material may be chipped or ground. The size of the biomass particles after chipping or grinding is typically between 0.2 and 30 mm. After chipping a number of other pretreatment options may be used to further prepare the biomass for saccharification and fermentation, including steam explosion, ammonia fiber explosion, acid hydrolysis.

1. Steam Explosion

Steam explosion is a very common method for pretreatment of lignocellulosic biomass and increases the amount of cellulose available for enzymatic hydrolysis (U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process causes hemicellulose degradation and lignin transformation. Addition of $H_2SO_4$, $SO_2$, or $CO_2$ to the steam explosion reaction can improve subsequent cellulose hydrolysis, decrease production of inhibitory compounds and lead to the more complete removal of hemicellulose (Morjanoff and Gray, 1987).

2. Ammonia Fiber Explosion (AFEX)

In AFEX pretreatment, the biomass is treated with approximately 1-2 kg ammonia per kg dry biomass for approximately 30 minutes at pressures of 1.5 to 2 MPa. (U.S. Pat. No. 4,600,590; U.S. Pat. No. 5,037,663; Mes-Hartree, et al., 1988). Like steam explosion, the pressure is then rapidly reduced to atmospheric levels, boiling the ammonia and exploding the lignocellulosic material. AFEX pretreatment appears to be especially effective for biomass with a relatively low lignin content, but not for biomass with high lignin content such as newspaper or aspen chips (Sun and Cheng, 2002).

3. Acid Hydrolysis

Concentrated or dilute acids may also be used for pretreatment of lignocellulosic biomass. $H_2SO_4$ and HCl have been used at high, >70%, concentrations. In addition to pretreatment, concentrated acid may also be used for hydrolysis of cellulose (U.S. Pat. No. 5,972,118). Dilute acids can be used at either high (>160° C.) or low (<160° C.) temperatures, although high temperature may be beneficial for cellulose hydrolysis (Sun and Cheng, 2002). $H_2SO_4$ and HCl at concentrations of 0.3 to 2% (w/w) and treatment times ranging from minutes to 2 hours or longer can be used for dilute acid pretreatment.

Other pretreatments include alkaline hydrolysis, oxidative delignification, organosolv process, or biological pretreatment; see Sun and Cheng (2002).

B. Saccharification

After pretreatment, the cellulose in the lignocellulosic biomass may be hydrolyzed with cellulase enzymes. Cellulase catalyzes the breakdown of cellulose to release glucose which can then be fermented into ethanol.

Bacteria and fungi produce cellulases suitable for use in ethanol production (Duff and Murray, 1995). For example, *Cellulomonas fimi* and *Thermomonospora fusca* have been extensively studied for cellulase production. Among fungi, members of the *Trichoderma* genus, and in particular *Trichoderma reesi*, have been the most extensively studied. Numerous cellulases are available from commercial sources as well. Cellulases are usually actually a mixture of several different specific activities. First, endoglucanases create free chain ends of the cellulose fiber. Exoglucanases remove cellobiose units from the free chain ends and beta-glucosidase hydrolyzes cellobiose to produce free glucose.

Reaction conditions for enzymatic hydrolysis are typically around pH 4.8 at a temperature between 45 and 50° C. with incubations of between 10 and 120 hours. Cellulase loading can vary from around 5 to 35 filter paper units (FPU) of activity per gram of substrate Surfactants like Tween 20, 80, polyoxyethylene glycol or Tween 81 may also be used during enzyme hydrolysis to improve cellulose conversion. Additionally, combinations or mixtures of available cellulases and other enzymes may also lead to increased saccharification.

Aside from enzymatic hydrolysis, cellulose may also be hydrolyzed with weak acids or hydrochloric acid (Lee et al., 1999).

C. Fermentation

Once fermentable sugars have been produced from the lignocellulosic biomass, those sugars may be used to produce ethanol via fermentation. Fermentation processes for producing ethanol from lignocellulosic biomass are extensively reviewed in Olsson and Hahn-Hagerdal (1996). Briefly, for maximum efficiencies, both pentose sugars from the hemicellulose fraction of the lignocellulosic material (e.g., xylose) and hexose sugars from the cellulose fraction (e.g., glucose) should be utilized. *Saccharomyces cerevisiae* are widely used for fermentation of hexose sugars. Pentose sugars, released from the hemicellulose portion of the biomass, may be fermented using genetically engineered bacteria, including *Escherichia coli* (U.S. Pat. No. 5,000,000) or *Zymomonas mobilis* (Zhang et al., 1995). Fermentation with yeast strains is typically optimal around temperatures of 30 to 37° C.

D. Simultaneous Saccharification and Fermentation (SSF)

Cellulase activity is inhibited by its end products, cellobiose and glucose. Consequently, as saccharification proceeds, the build up of those end products increasingly inhibits continued hydrolysis of the cellulose substrate. Thus, the fermentation of sugars as they are produced in the saccharification process leads to improved efficiencies for cellulose utilization (e.g., U.S. Pat. No. 3,990,944). This process is known as simultaneous saccharification and fermentation (SSF), and is an alternative to the above described separate saccharification and fermentation steps. In addition to increased cellulose utilization, SSF also eliminates the need for a separate vessel and processing step. The optimal temperature for SSF is around 38° C., which is a compromise between the optimal temperatures of cellulose hydrolysis and sugar fermentation. SSF reactions can proceed up to 5 to 7 days.

E. Distillation

The final step for production of ethanol is distillation. The fermentation or SSF product is distilled using conventional methods producing ethanol, for instance 95% ethanol.

II. Plant Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Components that may be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. 2004/0049802, the entire disclosure of which is specifically incorporated herein by reference). In one embodiment of the invention, the native promoter of a lignin biosynthesis coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. Sequences that are derived from genes that are highly expressed in plants may be desirable.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that lignin biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a lignin biosynthesis coding sequence is used. Alternatively, a heterologous 3' end may enhance the expression of sense or antisense lignin biosynthesis coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product.

Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable" markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. Antisense and RNAi Constructs

Antisense and RNAi treatments represent one way of altering lignin biosynthesis activity in accordance with the invention (e.g., by down regulation of NST transcription factor). In particular, constructs comprising a lignin biosynthesis coding sequence, including fragments thereof, in antisense orientation, or combinations of sense and antisense orientation, may be used to decrease or effectively eliminate the expression of a lignin biosynthesis gene in a plant and obtain an improvement in lignin profile as is described herein. Accordingly, this may be used to "knock-out" the function of a lignin biosynthesis coding sequence or homologous sequences thereof.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of a lignin biosynthesis gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that one embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art (e.g., Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

IV. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species, including biofuel crop species, may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is an efficient method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishida et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Similarly, *Agrobacterium* mediated transformation has also proven to be effective in switchgrass. Somleva et al., (2002) describe the creation of approximately 600 transgenic switchgrass plants carrying a bar gene and a uidA gene (beta-glucuronidase) under control of a maize ubiquitin promoter and rice actin promoter respectively. Both genes were expressed in the primary transformants and could be inherited and expressed in subsequent generations. Addition of 50 to 200 μM acetosyringone to the inoculation medium increased the frequency of transgenic switchgrass plants recovered.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and often, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

Richards et al., (2001) describe the creation of transgenic switchgrass plants using particle bombardment. Callus was bombarded with a plasmid carrying a sgfp (green fluorescent protein) gene and a bar (bialaphos and Basta tolerance) gene under control of a rice actin promoter and maize ubiquitin promoter respectively. Plants regenerated from bombarded callus were Basta tolerant and expressed GFP. These primary transformants were then crossed with non-transgenic control plants, and Basta tolerance was observed in progeny plants, demonstrating inheritance of the bar gene.

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTOAGAR, GELRITE, and GELGRO are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

V. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces* viridochromogenes. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318).

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be beneficial, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins m-2 s-1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and 14C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:
 (a) plant seeds of the first (starting line) and second (donor plant line that comprises a transgene of the invention) parent plants;
 (b) grow the seeds of the first and second parent plants into plants that bear flowers;
 (c) pollinate a flower from the first parent plant with pollen from the second parent plant; and
 (d) harvest seeds produced on the parent plant bearing the fertilized flower.

Backcrossing is herein defined as the process including the steps of:
 (a) crossing a plant of a first genotype containing a desired gene, DNA sequence or element to a plant of a second genotype lacking the desired gene, DNA sequence or element;
 (b) selecting one or more progeny plant containing the desired gene, DNA sequence or element;
 (c) crossing the progeny plant to a plant of the second genotype; and
 (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. Definitions

Biofuel crop species: A plant that may be used to provide biomass for production of lignocellulosic-derived ethanol. Examples of such plants include switchgrass (*Panicum virgatum*), giant reed (*Arundo donax*), reed canarygrass (*Phalaris arundinacea*), *Miscanthus x giganteus, Miscanthus* sp., sericea lespedeza (*Lespedeza cuneata*), corn, sugarcane, sorghum, millet, ryegrass (*Lolium multiflorum, Lolium* sp.), timothy, *Kochia* (*Kochia scoparia*), forage soybeans, alfalfa, clover and other legumes, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, poplar, willow, and agave, among others, as well as other crops such as wheat, rice, and grapes.

Expression: The combination of intracellular processes, including transcription and translation undergone by a coding DNA molecule such as a structural gene to produce a polypeptide.

Forage crops: Crops including grasses and legumes used as fodder or silage for livestock production.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

R0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Transformation constructs will often comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VIII. Examples

The following examples are included to demonstrate illustrative embodiments of the invention. It should be appreciated by those of skill in the art that the techniques disclosed in the examples which follow represent techniques discovered by the inventor to function well in the practice of the invention, and thus can be considered to constitute one embodiment of modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Characterization of *M. truncatula* MtSTP Mutants

Figure 1:
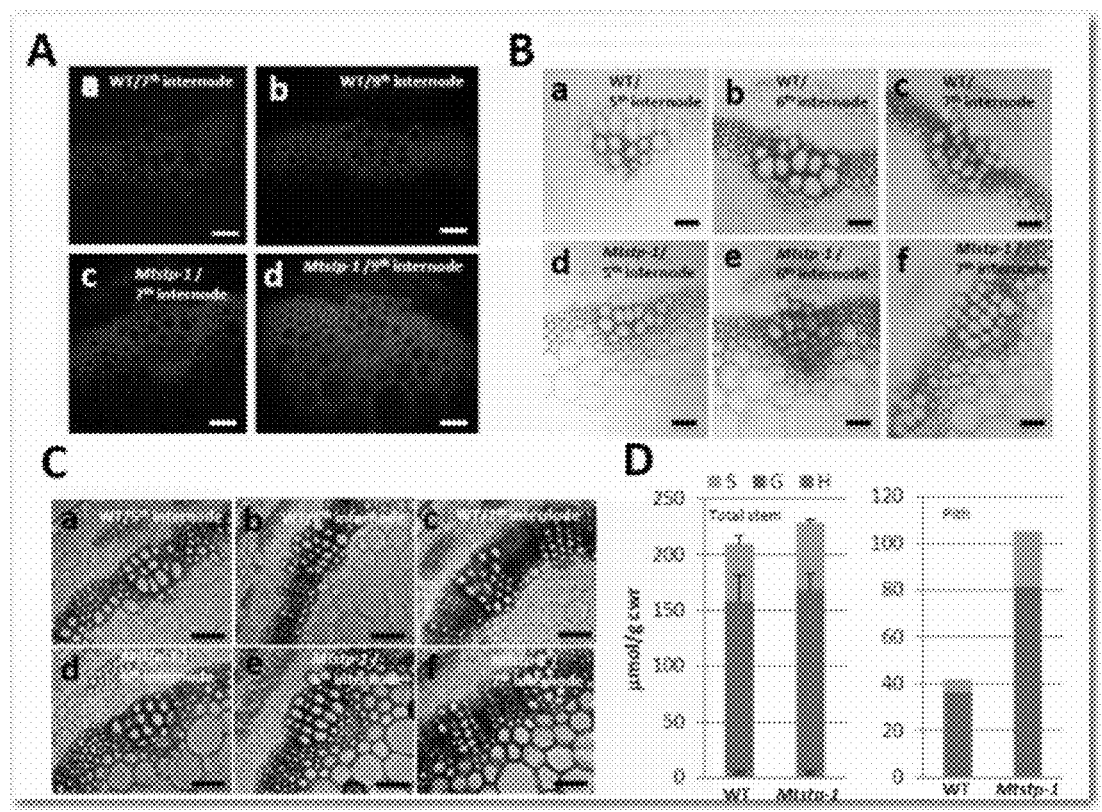
FIG. 1. Phenotypic analysis of the Mtstp-1 mutant as revealed by histo- and immune-chemical staining of stem cross sections. (A), UV autofluorescence of cross sections of $7^{th}$ (a, c) and $9^{th}$ (b, d) stem internodes. (a,b) wild type; blue color is lignin autofluorescence in vascular bundles and interfascicular fibers. (c,d), Mtstp-1; lignification first extends to pith cells near the bundle (c) and then to the central part in older internodes (d). (B) Phloroglucinol staining of the $5^{th}$ (a), $6^{th}$ (b) and $7^{th}$ (c) internodes of stems from wild-type plants, and the $5^{th}$ (d), $6^{th}$ (e) and $7^{th}$ (f) internodes of the Mtstp-1 mutant. (C) Mäule staining of the $5^{th}$ (a), $6^{th}$ (b) and $7^{th}$ (c) internodes of stems from wild type plants, and the $5^{th}$ (d), $6^{th}$ (e) and $7^{th}$ (f) internodes of the Mtstp-1 mutants. (D) Lignin content and composition determined by thioacidolysis. (left) total stem, (right) isolated pith. (E) Light microscopy of the pith cell walls in wild type (a) and mutant (b). (c) and (d) are higher magnifications of the marked areas of (a) and (b). (F) and (G) Detection of xylan and cellulose by immunohistochemistry using monoclonal antibodies against distinct xylan epitopes (F) and a carbohydrate-binding module that binds crystalline cellulose (G) in stem sections of wild type (upper panels) and Mtstp-1 mutant (lower panels). Antibody and CBM names are indicated on the upper panels. Bars are 20 μm in (A), (B), (C) and (E), and in 10 μm (F) and (G).
Figure 1:
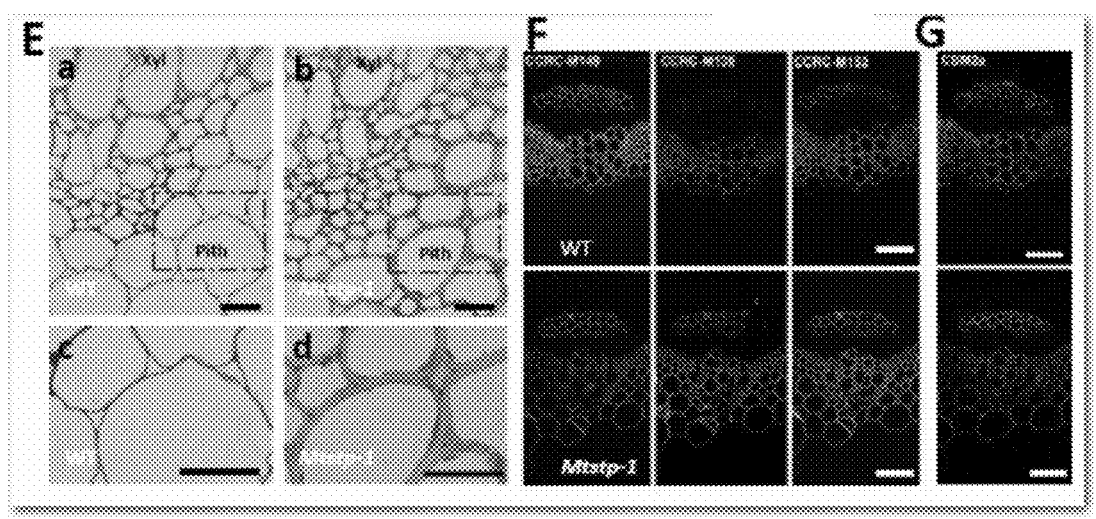
Figure 5:
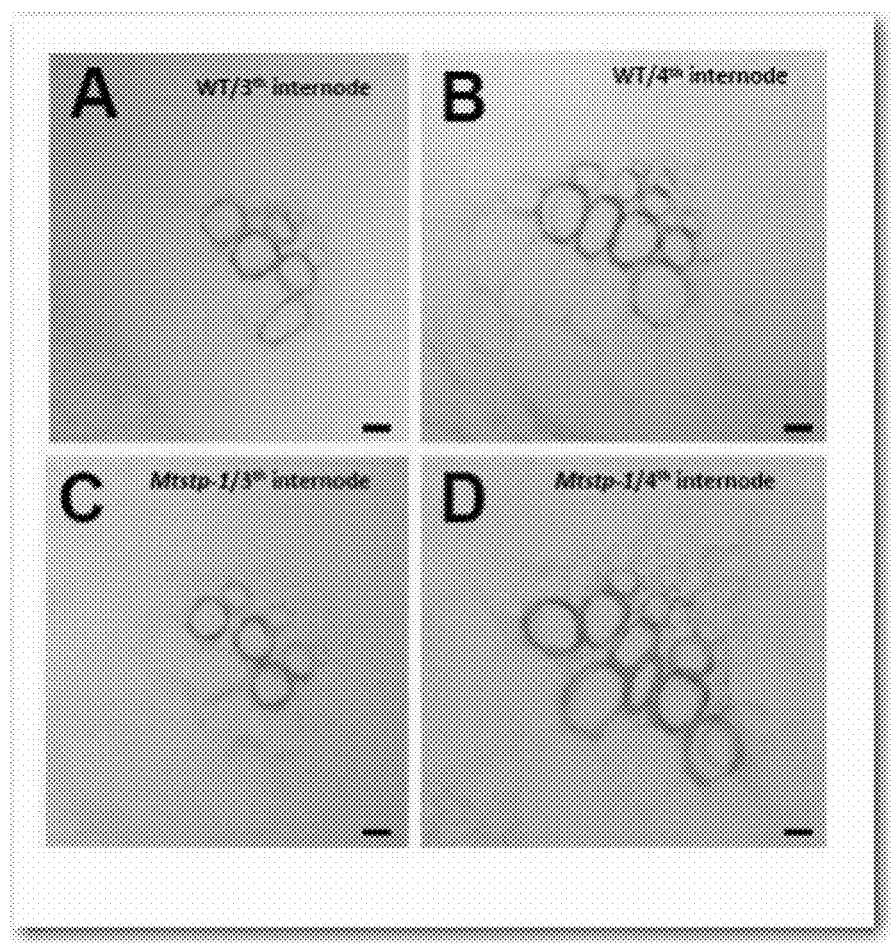
FIG. 5. Phloroglucinol staining of cross sections of young stem internodes of wild type *M. truncatula* (A,B) and the Mtstp-1 mutant (C,D). A and C show internode 3, B and D internode 4. Note that ectopic lignification of pith cells has not yet started at this stage of development in the Mtstp-1 mutant. Bars in (A-D) are 20 μm.

Screening for ectopic lignification mutants in *Arabidopsis* has identified two mutants with lignified pith cells (Cano-Delgado et al., 2000; Zhong et al., 2000), but neither mutation defines a negative transcriptional regulator of lignin synthesis (Ellis et al., 2002). To identify genes controlling secondary cell wall formation, a *Medicago truncatula* Tnt1 retrotransposon insertion population (Tadege et al., 2005; Tadege et al. 2008) was screened by UV microscopy of stem sections (Zhao et al. 2010; Tadege et al., 2008). Mutant line NF3788 showed ectopic lignin autofluorescence in pith cells, with the strongest phenotype in mature internodes (FIG. 1A). Phloroglucinol and Mäule staining (FIG. 1B, C; FIG. 5) (19) confirmed progressive ectopic lignification into the pith with increasing stem maturity in the mutant. Furthermore, the red color of the Mäule staining suggested a high syringyl (S) lignin content in the pith cell walls, which was confirmed quantitatively by thioacidolysis (Lapierre et al., 1985).

Although total lignin was only slightly increased in the mutant, lignin levels were double in isolated pith material, with a four-fold higher level of S lignin units than in pith from wild type plants (FIG. 1D). The walls of the lignified pith cells in the mutant were thicker than in the wild type (FIG. 1E), and contained xylan and more cellulose as determined by immunohistochemistry using three distinct xylan-directed antibodies (Pattahil et al., 2010) and the cellulose-directed carbohydrate binding module CBM2a (Blake et al., 2006; FIG. 1F), confirming that the pith cell walls in the mutant had undergone true secondary thickening as opposed to only lignification. The mutant was named Mtstp-1 (Secondary wall Thickening in Pith).

Example 2

Microarray Analysis of *M. truncatula* WRKY Mutants

To identify the gene responsible for the STP phenotype, microarray analysis was performed using RNA isolated from the 4$^{th}$ to 8$^{th}$ internodes of control and mutant plants in a segregating population.

Total RNA samples from fifth to eighth internodes of *M. truncatula* were subjected to Affymetrix microarray analysis. Segregating progeny without the STP phenotype were used as controls. For *Arabidopsis*, total RNA from stems of Atstp-1 and Atstp-2 homozygous plants and Columbia wild type plants was used. RNA was isolated with Tri-reagent according to the manufacturer's protocol (Invitrogen, Chicago, Ill.), and cleaned and concentrated using the RNeasy® MinElute Cleanup Kit (Qiagen, Carol Stream, Ill.). Ten micrograms of purified RNA from three biological replicates was used for microarray analysis. Probe labeling, hybridization and scanning were conducted according to the manufacturer's instructions (Affymetrix, Santa Clara, Calif.). Data normalization was conducted using robust multi-chip average (RMA) (Irizarry et al., 2003). The presence/absence call for each probe set was obtained from dCHIP (Li et al., 2001). Genes with significantly different expression between the wild type control and mutants were selected using Associative Analysis as described (Dozmorov & Centola, 2003). Type I family-wise error rate was reduced by using a Bonferroni corrected P-value threshold of 0.05/N, where N represents the number of genes present on the chip. The false discovery rate was monitored and controlled by Q-value (false discovery rate) calculated using Extraction of Differential Gene Expression (EDGE; Leek et al., 2006; Storey et al., 2007).

Fifty seven probe sets were down-regulated in the mutant line by at least 2-fold (Table 1), and candidate genes were selected based on their level of down-regulation and stem preferential expression in the *Medicago* Gene Expression Atlas (Benedito et al., 2008). One candidate, Mtr.5137.1.S1_at, contained a Tnt1 insertion which co-segregated with the ectopic lignification phenotype. Using the Mtr.5137.1.S1_at probe sequence (SEQ ID NO:28) to search against public *M. truncatula* sequence databases at www-.medicago.org, the coding sequence of MtSTP, IMGA|AC202489_11.1 (SEQ ID NO:29), was identified, as well as the corresponding genomic sequence (SEQ ID NO:: 30; GenBank Accession HM622066). The Tnt1 insertion was located at the far 3' end of the last intron, as confirmed by RT-PCR (FIG. 2A, B). There was no expression of MtSTP in the mutant (FIG. 2C).

TABLE 1

Genes with expression level changed more than 2-fold in Mtstp-1 mutant plants compared to wild type controls ("CK").

| Annotation | Probesets | Mutant/CK |
| --- | --- | --- |
| legume specific high in nod nodule-specific cysteine-rich peptide 59aa | Mtr.12854.1.S1_at | 0.01 |
| cysteine proteinase/Peptidase | Mtr.38411.1.S1_at | 0.07 |
| cysteine proteinase | Mtr.8672.1.S1_at | 0.09 |
| invertase/pectin methylesterase inhibitor family protein flower and seeds | Mtr.11656.1.S1_at | 0.19 |
| glycoside hydrolase family 28 protein polygalacturonase (pectinase) family protein | Mtr.10905.1.S1_at | 0.23 |
| ZPR1, a small leucine zipper-containing protein that interacts with REV HD- ZIPIII and is involved in the establishment of leaf polarity | Mtr.37079.1.S1_at | 0.24 |
| glycoside hydrolase family 28 protein, polygalacturonase (pectinase) family protein | Mtr.4037.1.S1_at | 0.24 |
| glycoside hydrolase family 28 protein, polygalacturonase (pectinase) family protein high in stem | Mtr.43323.1.S1_at | 0.25 |
|  | Mtr.5137.1.S1_at | 0.27 |
| Polygalacturonase-like protein | Mtr.43324.1.S1_s_at | 0.27 |
| unknown protein, domain Nitrate-induced NOI | Mtr.33006.1.S1_a_at | 0.29 |
| unknown function DUF668 | Mtr.16223.1.S1_at | 0.30 |
| AATP1 (AAA-ATPASE 1); ATP binding/ATPase high in petiole stem | Mtr.34925.1.S1_at | 0.32 |
| legume specific hypothetic protein | Mtr.21016.1.S1_at | 0.33 |
| high in seed, ATFER1 (FERRETIN 1); ferric iron binding | Mtr.19818.1.S1_at | 0.35 |
| auxin-responsive protein-related | Mtr.22024.1.S1_at | 0.35 |
| Gibberellin 20-oxidase-like protein, gibberellin 2-oxidase activity which acts specifically on C-20 gibberellins stem flower | Mtr.32389.1.S1_at | 0.35 |
| leucine-rich repeat transmembrane protein kinase, putative everywhere low in petiole and stem | Mtr.47343.1.S1_s_at | 0.36 |
| pathogenesis-related protein Allergen V5/Tpx-1 related; Ves allergen | Mtr.16234.1.S1_at | 0.36 |
| unknown | Mtr.29608.1.S1_at | 0.37 |
| unknown protein At2g28780 | Mtr.4834.1.S1_at | 0.37 |
| unknown protein At2g28780 | Mtr.32441.1.S1_at | 0.37 |
| phototropic-responsive NPH3 family protein at3g19850 | Mtr.44412.1.S1_at | 0.38 |
| IAA9 (indoleacetic acid-induced protein 9); | Mtr.48811.1.S1_at | 0.38 |
| Benzoyl coenzyme A: benzyl alcohol benzoyl transferase | Mtr.35296.1.S1_at | 0.39 |
| ATEXPB3 (*ARABIDOPSIS THALIANA* EXPANSIN B3 | Mtr.32301.1.S1_at | 0.39 |

TABLE 1-continued

Genes with expression level changed more than 2-fold in Mtstp-1 mutant plants compared to wild type controls ("CK").

| Annotation | Probesets | Mutant/CK |
|---|---|---|
| Steroid 5alpha-reductase-like protein | Mtr.11495.1.S1_at | 0.40 |
| unknown | Mtr.47198.1.S1_s_at | 0.40 |
| legume specific | Mtr.32535.1.S1_at | 0.41 |
| Carbamoyl-phosphate synthase | Mtr.14704.1.S1_at | 0.41 |
| Leptin receptor long form | Mtr.2580.1.S1_at | 0.42 |
| Unknown | Mtr.51587.1.S1_at | 0.42 |
| Unknown | Mtr.50087.1.S1_at | 0.43 |
| Amine oxidase | Mtr.45133.1.S1_at | 0.43 |
| Aspartic proteinase 1 | Mtr.43525.1.S1_at | 0.43 |
| Eukaryotic transcription factor, DNA-binding; bZIP transcription factor | Mtr.20751.1.S1_at | 0.43 |
| Nitrite transporter | Mtr.37657.1.S1_at | 0.43 |
| Unknown | Mtr.26884.1.S1_at | 0.44 |
| Amine oxidase | Mtr.13014.1.S1_at | 0.44 |
| phototropic-responsive NPH3 family protein at5g47800 | Mtr.17669.1.S1_s_at | 0.44 |
| Unknown | Mtr.28009.1.S1_at | 0.45 |
| RING finger-like high in seed | Mtr.11210.1.S1_at | 0.45 |
| Unknown | Mtr.28009.1.S1_at | 0.45 |
| Amine oxidase | Mtr.38596.1.S1_at | 0.45 |
| phototropic-responsive NPH3 family protein at5g47800 | Mtr.27184.1.S1_at | 0.45 |
| phototropic-responsive NPH3 family protein at5g47800 | Mtr.34780.1.S1_at | 0.46 |
| phototropic-responsive NPH3 family protein at5g47800 | Mtr.17669.1.S1_at | 0.46 |
| FRD3 (FERRIC REDUCTASE DEFECTIVE 3); | Mtr.8402.1.S1_at | 0.47 |
| root specific, FRD3 (FERRIC REDUCTASE DEFECTIVE 3); | Mtr.41827.1.S1_s_at | 0.47 |
| root and nod, exonuclease -related contains At1g56310 | Mtr.24370.1.S1_at | 0.47 |
| root stem seed/unknown | Mtr.29378.1.S1_at | 0.48 |
| Mitogen-activated protein kinase | Mtr.40687.1.S1_at | 0.48 |
| Unknown | Mtr.39610.1.S1_at | 0.48 |
| Multi antimicrobial extrusion protein root | Mtr.15345.1.S1_at | 0.49 |
| Acetylornithine aminotransferase, root seed | Mtr.40048.1.S1_at | 0.49 |
| *ARABIDOPSIS THALIANA* EXPANSIN A6, petiole stem flower | Msa.2767.1.S1_at | 0.49 |
| Vacuolar acid invertase PsI-1 petiole stem flower | Mtr.6527.1.S1_at | 0.50 |
| DNA-binding WRKY root nodule | Mtr.21533.1.S1_at | 2.00 |
| Serine/threonine kinase-like protein root | Mtr.39440.1.S1_at | 2.02 |
| extracellular dermal glycoprotein root seed | Mtr.8559.1.S1_at | 2.02 |
| kinesin-related protein nod seed | Mtr.5286.1.S1_at | 2.03 |
| alpha galactosidase seed | Mtr.7099.1.S1_at | 2.04 |
| Disease resistance protein; Short-chain dehydrogenase/reductase SDR everywhere low | Mtr.48736.1.S1_at | 2.06 |
| alpha galactosidase seed | Mtr.10236.1.S1_at | 2.06 |
| Glutathione S-transferase GST 11 root | Mtr.41149.1.S1_at | 2.09 |
| stem and root CLE12 (CLAVATA3/ESR-RELATED 12); | Mtr.20062.1.S1_at | 2.10 |
| unknown protein | Mtr.39943.1.S1_at | 2.11 |
| unknown protein | Mtr.23313.1.S1_at | 2.20 |
| high in root | Msa.664.1.S1_at | 2.20 |
| ADR6 protein high in root | Mtr.37573.1.S1_at | 2.20 |
| ABC transporter related; ABC transporter | Mtr.51808.1.S1_at | 2.32 |
| Esterase/lipase/thioesterase *ARABIDOPSIS THALIANA* CARBOXYESTERASE | Mtr.19303.1.S1_at | 2.34 |
| Acyltransferase 1 HCT like | Mtr.20618.1.S1_s_at | 2.37 |
| Recoverin; Calcium-binding EF-hand high in root and seed | Mtr.17718.1.S1_at | 2.38 |
| MtN3-like protein high in flower | Mtr.38292.1.S1_at | 2.38 |
| Unknown | Mtr.39765.1.S1_at | 2.41 |
| PHO1-like high in vegetative bud | Mtr.801.1.S1_s_at | 2.43 |
| hypothetical protein | Mtr.16773.1.S1_x_at | 2.46 |
| BZIP transcription factor, high in root | Mtr.40450.1.S1_at | 2.54 |
| type 2 and phytocystatins high in pod and seed | Mtr.52258.1.S1_at | 2.55 |
| cytochrome P450, family 71 | Mtr.2309.1.S1_at | 2.56 |
| DNA-binding family protein | Mtr.9513.1.S1_at | 2.59 |
| Unknown | Mtr.31695.1.S1_at | 2.68 |
| unnamed protein product | Mtr.49452.1.S1_at | 2.84 |
| Peptidase aspartic; Peptidase S8 and S53, subtilisin | Mtr.15958.1.S1_s_at | 2.91 |
| FAD-binding domain-containing protein, not specific tissue expressed | Mtr.49451.1.S1_at | 3.06 |
| ATPase 2 | Mtr.8398.1.S1_at | 3.34 |
| root high, BZIP transcription factor | Mtr.44023.1.S1_at | 3.35 |
| high in vegetative bud, ERD1/XPR1/SYG1 family | Mtr.26080.1.S1_at | 3.69 |

TABLE 1-continued

Genes with expression level changed more than 2-fold in Mtstp-1 mutant plants compared to wild type controls ("CK").

| Annotation | Probesets | Mutant/CK |
|---|---|---|
| AATP1 (AAA-ATPASE 1); ATP binding/ATPase at5g40010 | Mtr.5209.1.S1_at | 3.78 |
| root, nod, seed | Mtr.32196.1.S1_at | 4.10 |
| Germin-like protein | Mtr.42985.1.S1_at | 4.17 |
| Myosin II heavy chain like protein | Mtr.2055.1.S1_at | 4.68 |
| Peptidase aspartic, active site; Peptidase A1, pepsin | Mtr.49094.1.S1_at | 7.44 |

Figure 6:
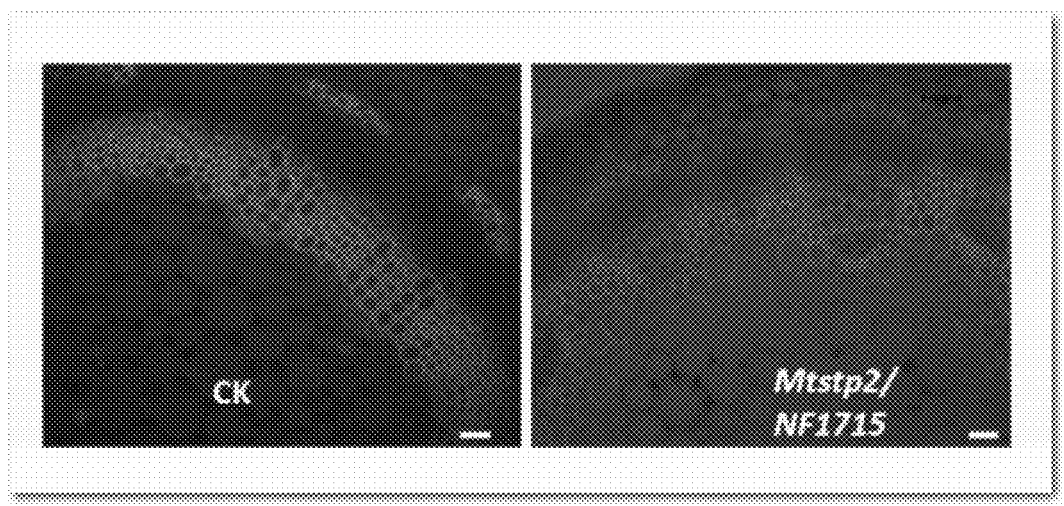
FIG. 6. Mtstp-2 also shows ectopic lignin autofluorescence. CK, wild type control. Bars are 20 μm.

To confirm that the STP phenotype was caused by the Tnt1 disruption in MtSTP, we used MtSTP gene-specific primers for reverse genetic screening of DNA pools from the Tnt1 mutant population, and another insertion line, NF1715/Mtstp-2, was recovered with a similar phenotype to that of Mtstp-1 (FIG. 6).

Example 3

Isolation and Characterization of *Arabidopsis thaliana* AtSTP Mutants

Figure 8:
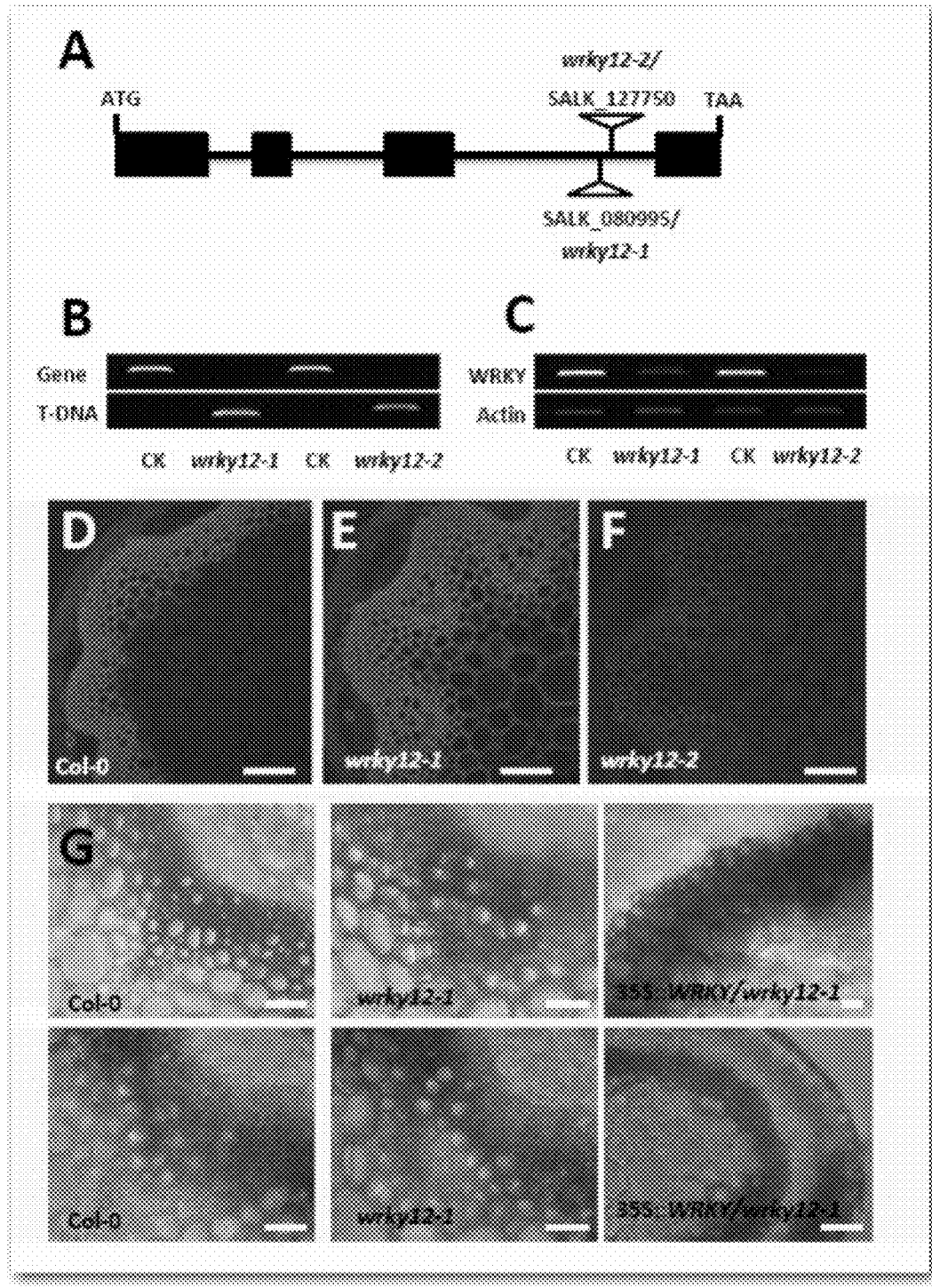
FIG. 8. Identification and phenotypic characterization of *Arabidopsis* wrky12 mutants. (A) AtWRKY12 gene structure and T-DNA insertion sites of two independent lines. (B) PCR identification of homozygotes of the T-DNA insertion lines; the wild type plant has only a gene-specific band whereas the insertion line has only a T-DNA-specific band. (C) RT-PCR analyses. AtWRKY expression was examined using primers covering the full length cDNA. ACTIN was used as control. (D-F) UV autofluorescence of equivalent stem cross sections from wild type (D), wrky12-1 (E) and wrky12-2 (F). (G) Phloroglucinol (upper panel) and Maule staining (lower panel) of *Arabidopsis* inflorescence stem cross sections. Sections were from wild type (Col-0), the wrky12-1 mutant, and wrky12-1 complemented with the wild type WRKY12 gene. Bars are 20 μm.
Figure 9:
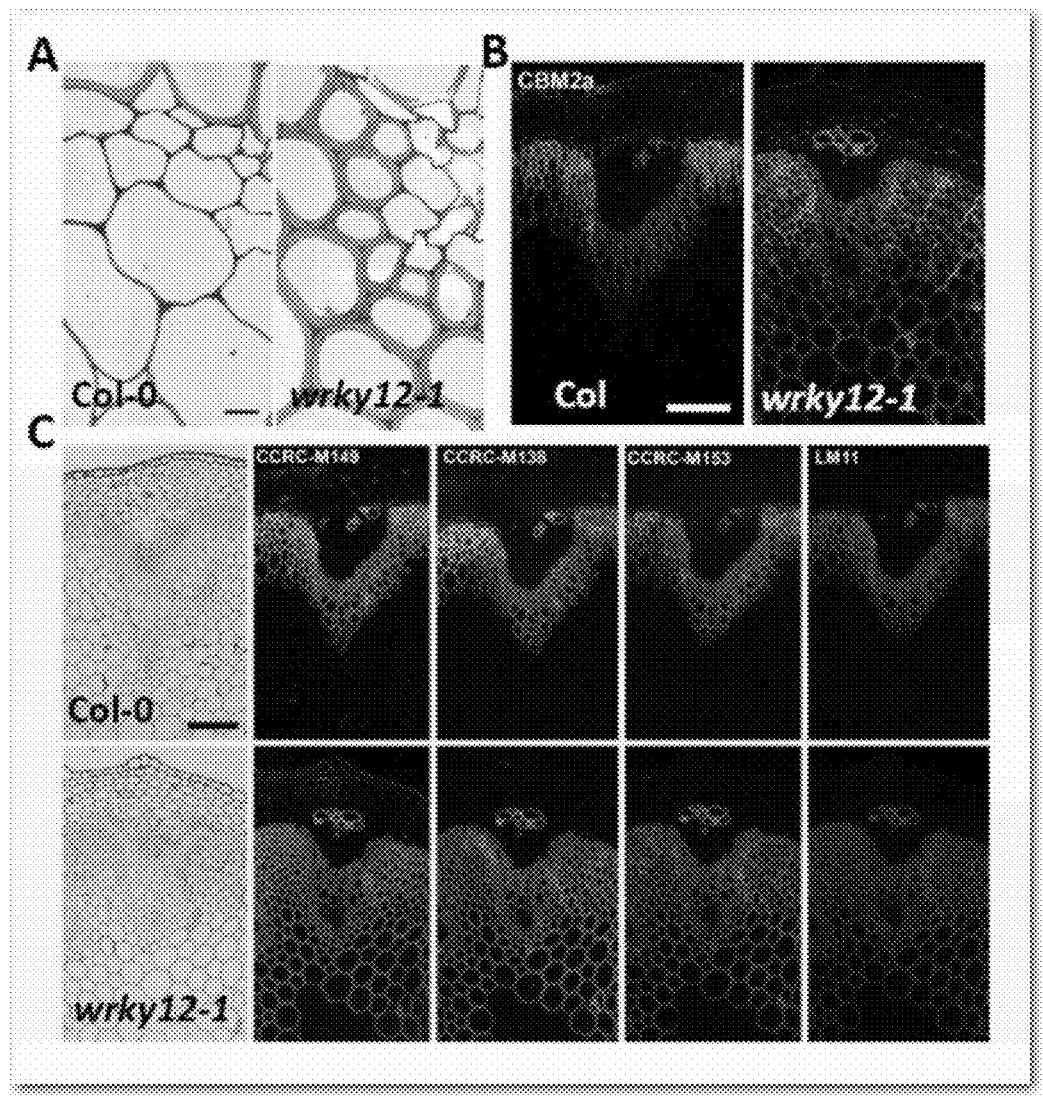
FIG. 9. Secondary wall thickening is increased in pith cells of *Arabidopsis* wrky12-1 plants. (A) Transmission electron microscopy (TEM) showing secondary wall thickening in the pith cells of wrky12-1 compared to wild type (Col-0). (B) Detection of cellulose by labeling with the cellulose-directed carbohydrate binding module, CBM2a. (C) Detection of xylan by immunolabeling using four different specific monoclonal antibodies in stem sections of wild type (upper panel) and wrky12-1 mutant (lower panel); the names of the antibodies are given on the upper panel. Bars are 10 μm.
Figure 10:
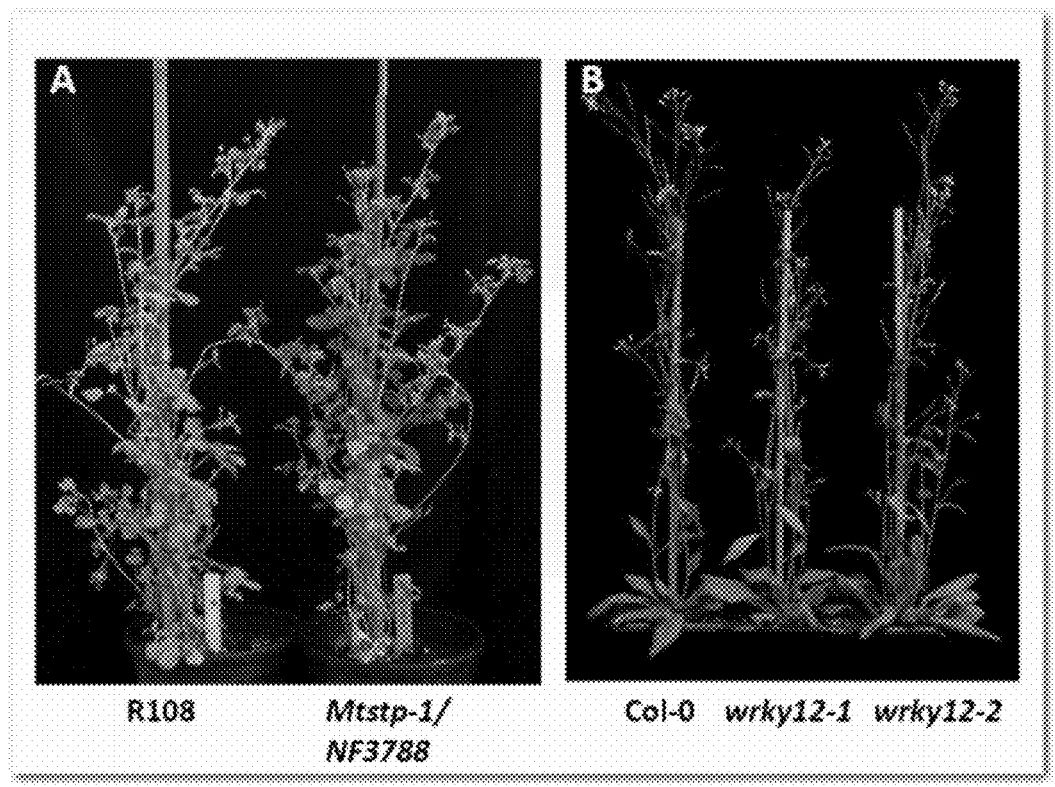
FIG. 10. Growth of *Medicago* stp and *Arabidopsis* wrky mutants. Loss of function of the WRKY gene controlling pith cell identity has no major impact on overall growth. Bar is 10 μm.

Two lines predicted to have T-DNA insertions in the AtWRKY-12 gene were obtained from the *Arabidopsis* Biological Resource Center (Alonso et al., 2003) and PCR and sequencing confirmed that both lines harbored an insertion in the last intron of the gene (FIG. 8A-B). Homozygous plants of both Atwrky12-1 and Atwrky12-2 showed down-regulated expression of the AtWRKY12 gene (FIG. S4C) and similar lignin phenotypes to those of the Mtstp mutants (FIG. 8D-8G). The walls of some pith cells underwent secondary thickening as shown by transmission electron microscopy (TEM) (FIG. 9A), and contained deposits of xylan and crystalline cellulose that appeared indistinguishable from those in the secondary walls of adjacent xylem cells (FIG. 9A-B). AtWRKY-12 and MtSTP are thus true homologs that function in controlling pith cell identity in *Medicago* and *Arabidopsis*, respectively. Mutations in these genes have little impact on growth, with the heights of the Mtstp-1/NF3788 and Atwrky12-1 and Atwrky12-2 mutants being similar to that of wild type plants (FIG. 10A-B).

Figure 3:
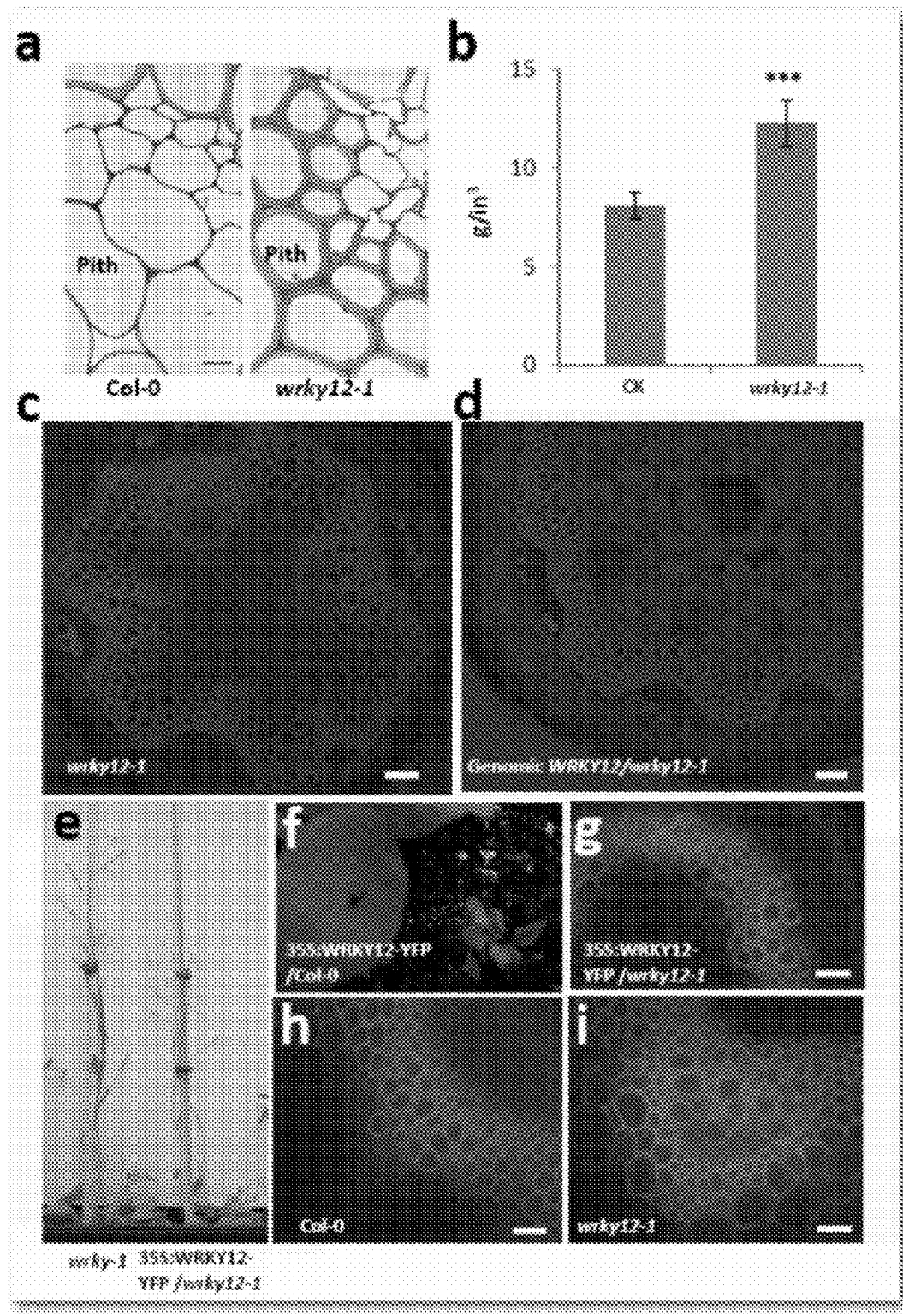
FIG. 3. Phenotypes and complementation of the *Arabidopsis* wrky-12 mutant. (A), transmission electron microscopy (TEM) showing pith cell wall thickness of wild-type *Arabidopsis* and the wrky12-1 mutant. (B), comparison of the biomass density in stems of wrky12-1 mutant and control (CK) (*** means highly significant as determined by t-test, p<0.0001). (C), UV autofluorescence of stem cross sections of wrky12-1; and (D), wrky12-1 transformed with the genomic complementation construct. (E), wrky12-1 mutant plant (left) and transformants of 35S:AtWRKY12-YFP in the mutant background (right). (F), extremely small plant phenotype of a 35S:AtWRKY12-YFP overexpressor. (G), UV autofluorescence of stem section showing complementation of the STP phenotype. (H) and (I), UV autofluorescence of stem sections of wild-type Col-0 and wrky12-1. Bars in C, D, G, H, and I are 20 μm.

Stems of the *Arabidopsis* wrky-12 mutant, and corresponding wild-type *Arabidopsis* were harvested, and their diameters (at three points along the stem) and lengths determined to obtain stem volume. The stems were then dried for 12 days in an oven to constant weight. Based on these measurements, the biomass density in the mutant stems was approximately 50% greater than that of the control stems (FIG. 3B), a remarkable increase. The wild type WRKY-12 genomic sequence including a 1.88 kb promoter sequence and 458 bp 3'-untranslated sequence was introduced into homozygous Atwrky-1 mutant plants. Out of 72 BASTA resistant T1 transformants, 62 exhibited a restored wild type phenotype (FIG. 3 A-B). In addition, a 35S:WRKY12-YFP fusion was transformed into the Atwrky12-1 background. Seven out of 36 transformants showed retarded growth, some being extremely small and unable to set seed (FIG. 3 C-D). However, the lignin UV autofluorescence pattern of stem sections was more normal, although the stems were thinner than wild type (FIG. 3 E-G). Thus, AtWRKY12 is responsible for the STP phenotype. Homozygous Atwrky12-1 plants were also transformed with a 35S:MtSTP construct, and 16 out of 37 transgenic T1 plants were restored to the wild-type phenotype, indicating conserved functions for the homologous *Medicago* and *Arabidopsis* STP genes.

Figure 11:
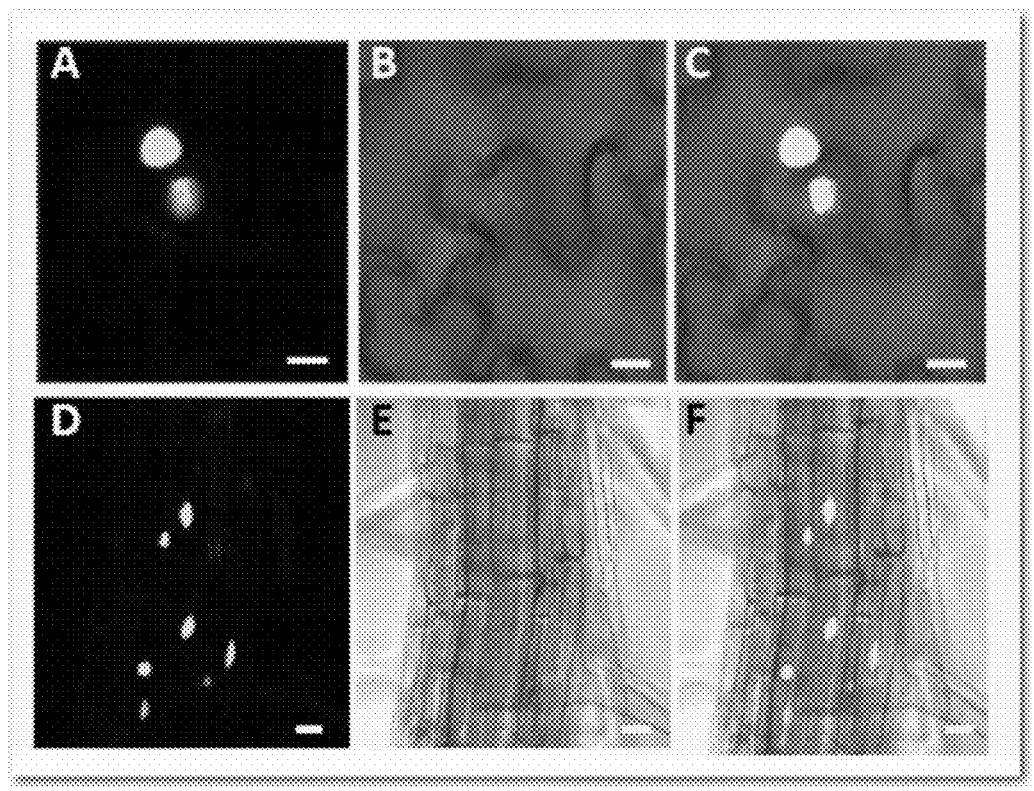
FIG. 11. Subcellular localization of WRKY-YFP fusion. The nuclear localization of WRKY protein was revealed by transient expression following leaf infiltration in *N. benthamiana* (A-C), and by table transformation in *Arabidopsis* (D-F). (A) YFP signal detected by confocal microscopy of the infiltrated *N. benthamiana* leaf. (B) Light microscopy of the infiltrated *N. benthamiana* leaf. (C) Overlapping image of (A) and (B). (D) YFP signal detected by confocal microscopy of transgenic *Arabidopsis* root. (E) Light microscopy of transgenic root. (F) Overlap of (D) and (E). Bar is 10 μm.
Figure 12:
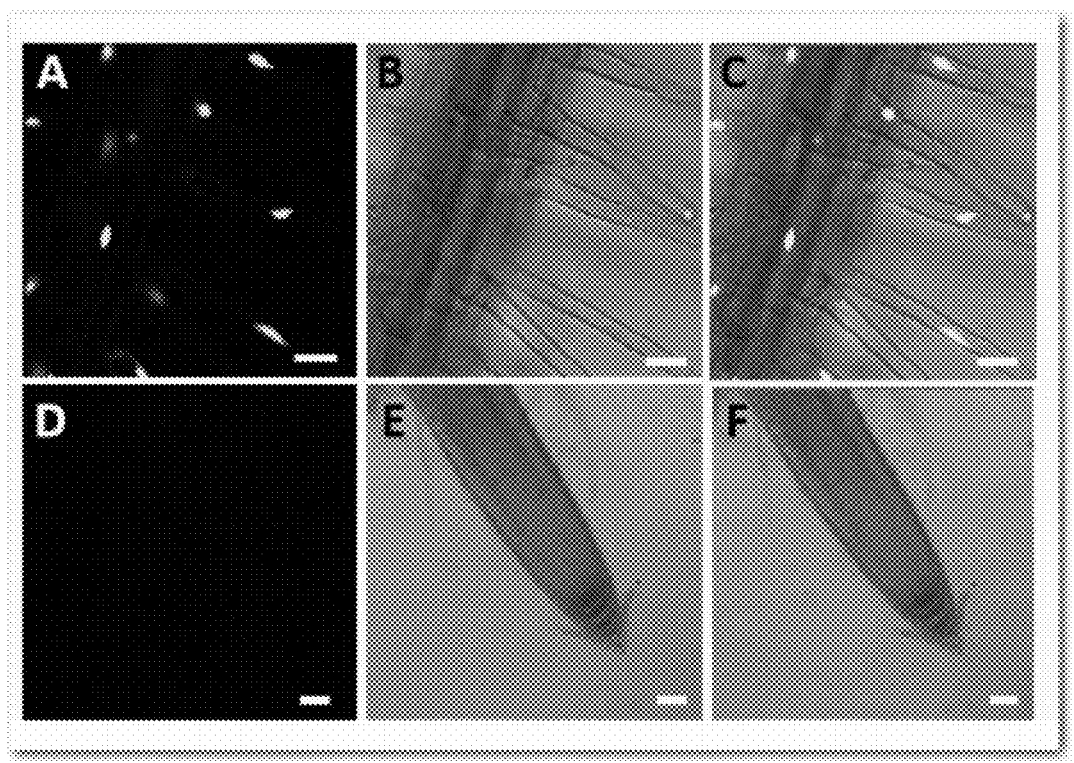
FIG. 12. WRKY-YFP protein is stable in the mature root region. WRKY-YFP signal was observed in the root hairs of mature roots (A-C) but not in the root meristem and elongation zone (D-F). (A) YFP signal detected by confocal microscopy of the mature root. (B) Light microscopy of the mature root. (C) Overlapping image of (A) and (B). (D) YFP channel showing no signal in the root tip and elongation zone. (E) Light microscopy of the root tip and elongation zone. (F) Overlap of (D) and (E). Bar is 10 μm.

Infiltration of *Nicotiana benthamiana* leaves or stable transformation of wild type *Arabidopsis* plants with *Agrobacterium* harboring the 35S:AtWRKY12-YFP fusion resulted in localization of YFP signal exclusively in the nucleus (FIG. 11). Although the construct was driven by the constitutive 35S promoter, the YFP signal in stably transformed *Arabidopsis* was localized to nuclei of root epidermis and hairs on mature roots. There was no signal in the root meristem or elongation zone (FIG. 12), suggesting that the stability of the protein is developmentally controlled.

Example 4

Analysis of Regulatory Effects in *A. thaliana* WRKY Mutants

Figure 13:
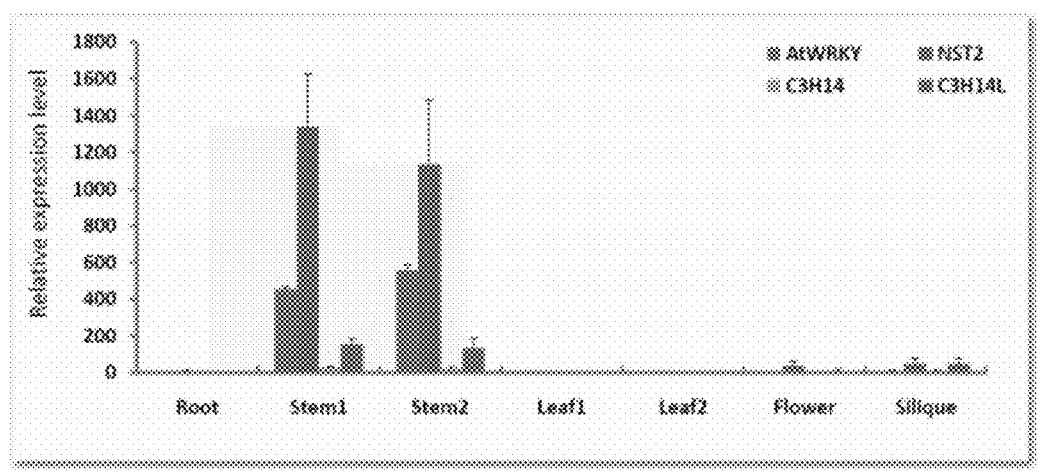
FIG. 13. Tissue-specific expression pattern of *Arabidopsis* WRKY12 transcripts and the downstream transcription genes NST2, C3H14 and C3H14L, as determined by qRT-PCR. Data show the means and standard deviations of 3 replicates.

Microarray analysis conducted as described in Example 2 indicated that 52 and 44 genes are up-regulated, and 95 and 286 down-regulated, more than 2-fold in the Atwrky12-1-1 and Atwrky12-2 mutants, respectively (Table 2). Among the up-regulated genes, a considerable number are related to secondary cell wall synthesis, including two C3H zinc finger TFs and the NAC domain TF NST2, which, like AtWRKY12, are most highly expressed in stem tissue (FIG. 13). AtNST2 regulates secondary wall thickening in anther endothecium and AtC3H14 (At1β66810) has been reported to be a transcriptional activator of secondary wall synthesis in an in vitro assay (Ko et al., 2009).

Figure 4:
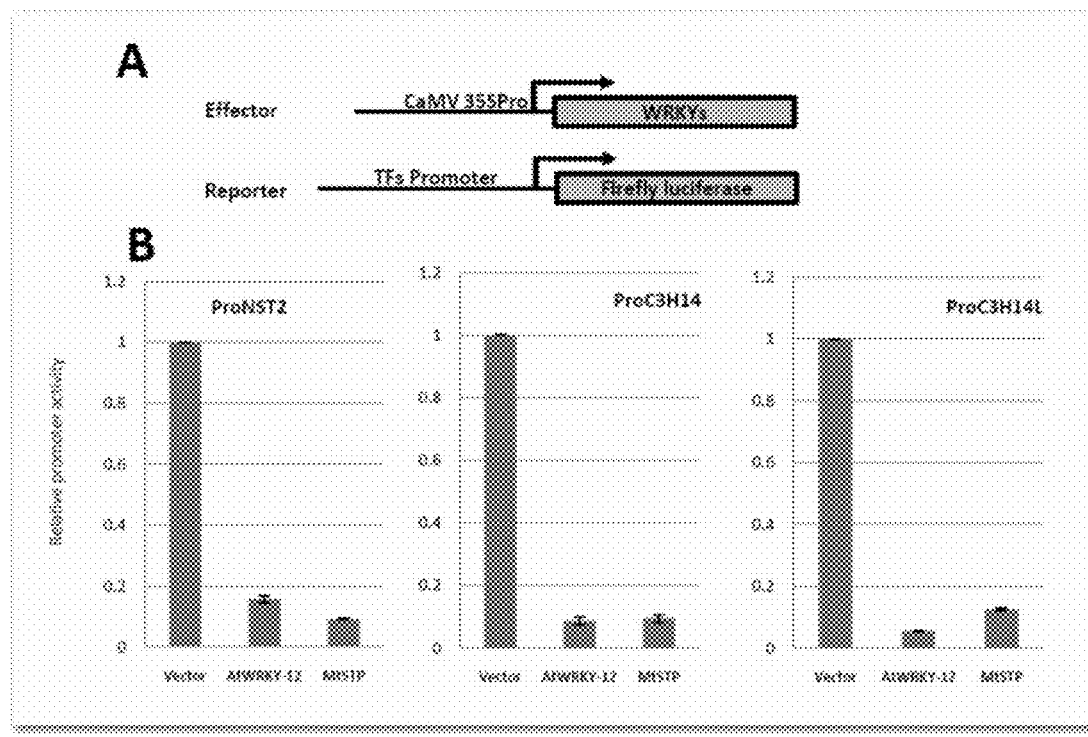
FIG. 4. STP protein represses the expression of downstream TFs. (A) Diagram showing the constructs used in transient expression assays. (B) Promoter activity of NST2, C3H14 and C3H14L is repressed by overexpression of AtSTP (AtWRKY12) or MtSTP genes; analyses were repeated at least 3 times with similar results using fresh isolated *Arabidopsis* leaf protoplasts. (C) Repression of NST2, C3H14 and C3H14L transcript levels in AtWRKY12 overexpression lines. (D) EMSA results showing direct binding of AtWRKY12 to the NST2 promoter fragment.
Figure 4:
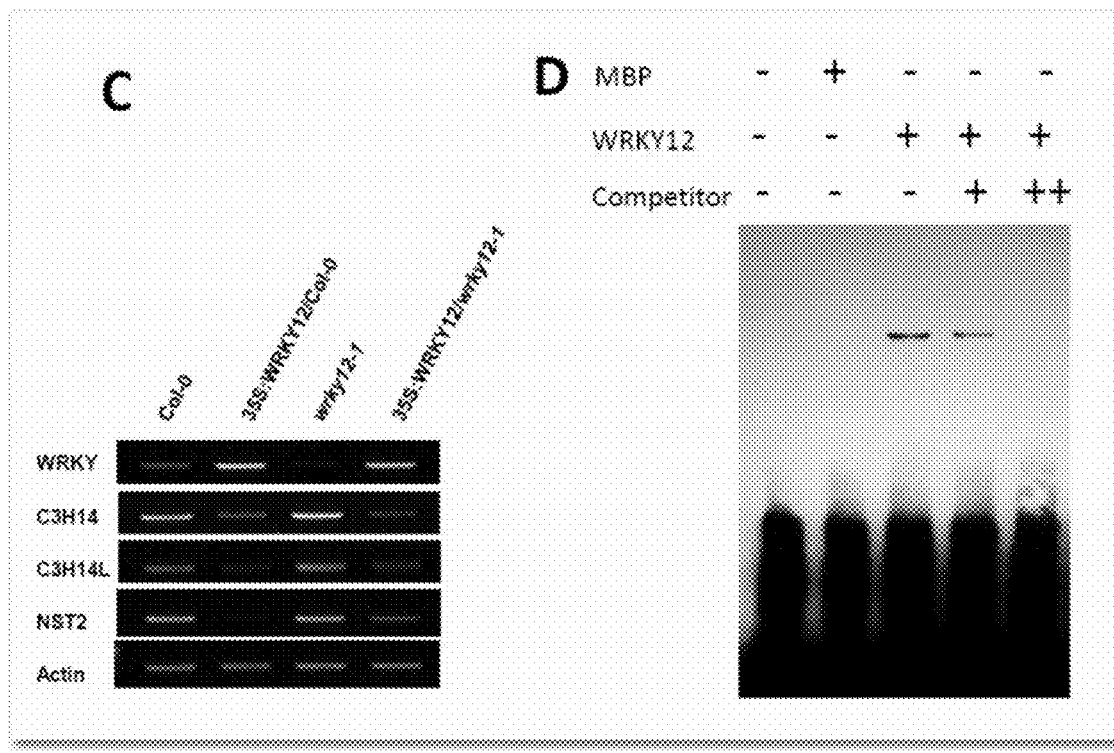
Figure 14:
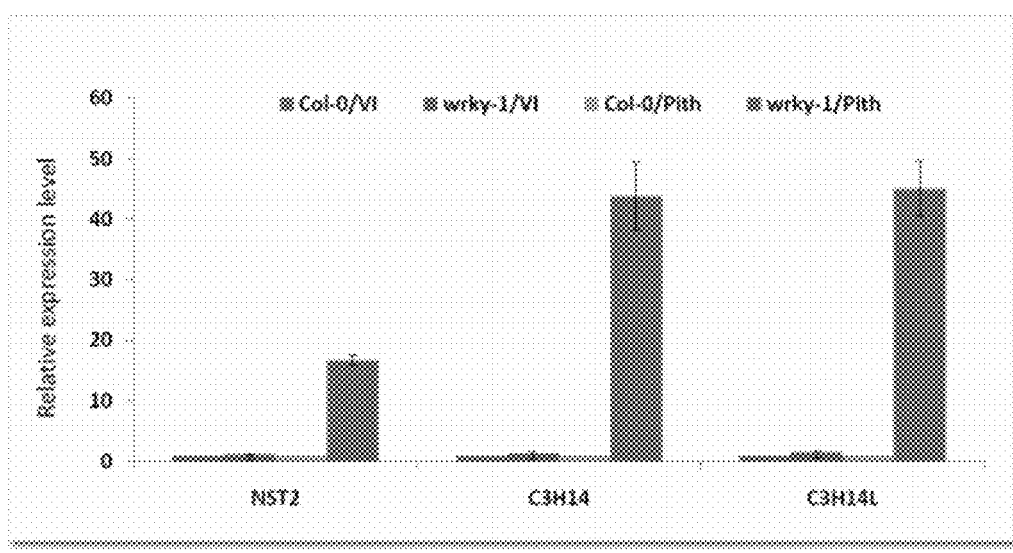
FIG. 14. qRT-PCR analysis showing expression of NST2, C3H14 and C3H14-like genes in vascular bundle and interfascicular cells (VI) and pith of wild type and wrky12-1 *Arabidopsis* plants, showing the preferential expression of these genes in the pith of wrky12-1 plants. Data show the mean and standard deviations of 3 replicates.
Figure 15:
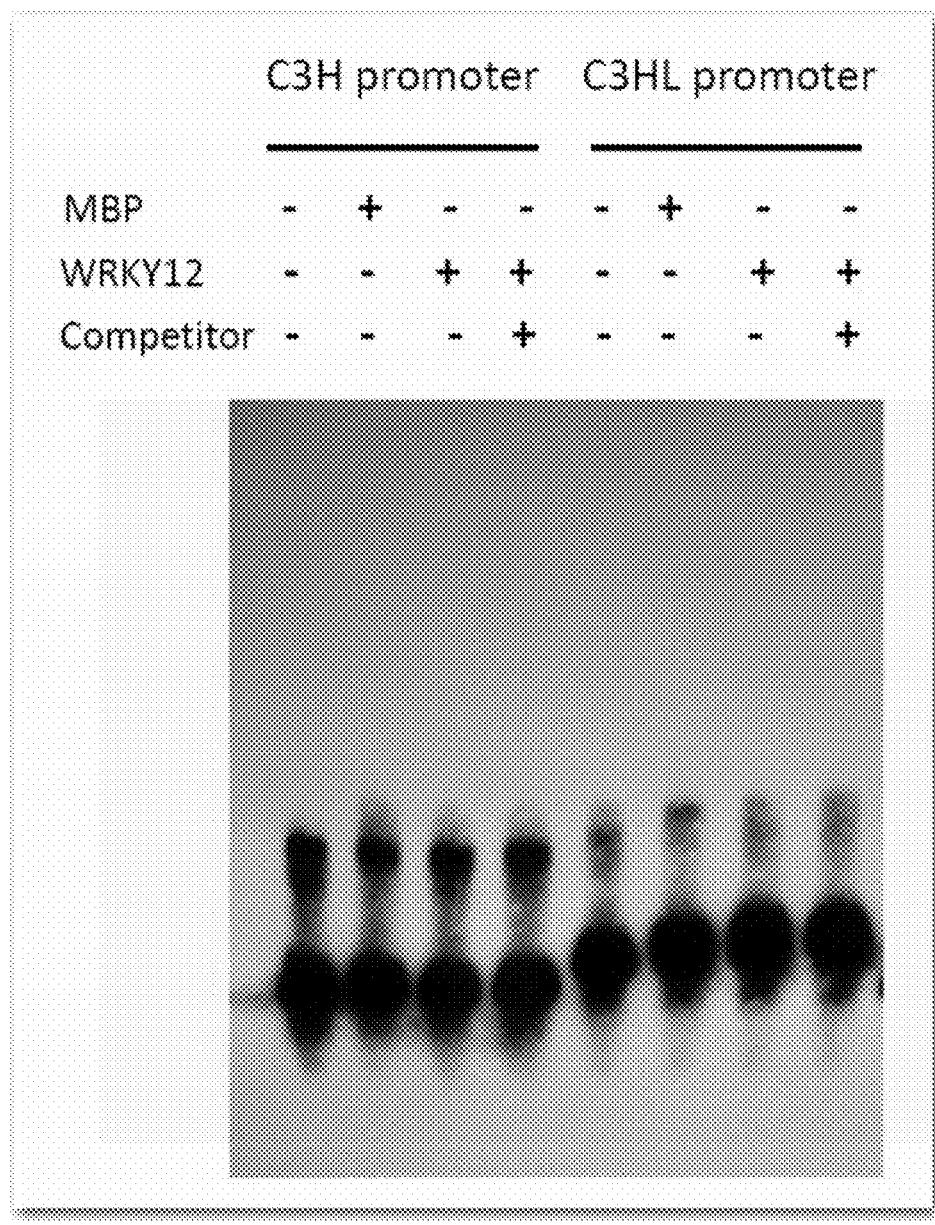
FIG. 15. EMSA for C3H promoters. No binding of WRKY12 protein to these two promoters was detected. See Example 11 for experimental details.

To test if expression of NST2 and the two C3H zinc finger TFs is up-regulated in pith cells following loss of WRKY-12 function, we isolated vascular and pith tissues from wild-type and Atwrky12-1 mutant plants. Quantitative RT-PCR analysis showed that the three TFs are highly expressed in cells with secondarily thickened walls, are barely up-regulated in vascular tissues of the Atwrky12-1 mutant, but are significantly up-regulated in pith cells of the mutant (FIG. 14). Thus, AtWRKY-12 controls cell identity in pith cells by acting as a negative regulator of NST2 and C3H zinc finger TFs. To directly demonstrate that STP proteins can repress the expression of these two classes of TFs, 35S:STP effector constructs, and reporter constructs in which the promoter sequences of NST2 or the two C3H TFs were placed in front of the firefly luciferase gene (FIG. 4A), were co-transformed into *Arabidopsis* leaf protoplasts. Co-expression of AtWRKY-12 or MtSTP down-regulated expression of all three reporters by about 10-fold compared to empty vector controls (FIG. 4B). To test if such repression also takes place in planta, we over-expressed AtWRKY-12 in the Col-0 and Atwrky12-1 backgrounds. This led to down-regulation of NST2 and the two C3H zinc finger TF genes in both backgrounds (FIG. 4C).

TABLE 2

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
| --- | --- | --- | --- |
| Expressed protein; supported by cDNA: gi_14190492_gb_AF380646.1_AF380646 | At4g32280 | 2.81 | 5.51 |
| prx10 peroxidase-like protein prx10 peroxidase, *Spinacia oleracea*, EMBL: SOY16776 | At5g15180 | 3.62 | 4.97 |
| auxin-induced protein (IAA20) identical to GB: 2618729 | At2g46990 | 1.25 | 3.56 |
| S-adenosyl-L-methionine:salicylic acid Carboxyl methyltransferase-like protein; supported by full-length cDNA: Ceres: 37493. | At5g55250 | 1.67 | 3.33 |
| putative protein; supported by cDNA: gi_10880502_gb_AF195894.1_AF195894 | At4g26320 | 3.27 | 3.11 |
| C-x8-C-x5-C-x3-H type Zinc finger protein, putative contains Pfam profile: PF00642: Zinc finger C-x8-C-x5-C-x3-H type (and similar) | At1g66810 | 2.93 | 3.06 |
| rac-like GTP binding protein Arac11; supported by cDNA: gi_14030642_gb_AF375412.1_AF375412 | At3g51300 | 2.52 | 2.72 |
| nodulin-like protein; supported by full-length cDNA: Ceres: 16393. | At2g37460 | 1.97 | 2.68 |
| putative zinc finger protein similar to CCCH zinc finger protein C3H-3GB: AAD24209 from [*Xenopus laevis*] | At1g68200 | 2.53 | 2.66 |
| putative protein proteinase inhibitor - *Oryza sativa*, PIR: T02667 | At3g63360 | 2.06 | 2.61 |
| Hypothetical protein similar to hypothetical protein GB: AAF24588 GI: 6692123 from [*Arabidopsis thaliana*] | At1g31320 | 1.38 | 2.59 |
| hypothetical protein predicted by genscan+; supported by full-length cDNA: Ceres: 871. | At1g69050 | 1.67 | 2.59 |
| homeobox-leucine zipper protein-like; supported by cDNA: gi_15450446_gb_AY052324.1_ | At5g47370 | 1.49 | 2.55 |
| putative expansin | At4g01630 | 1.57 | 2.54 |
| small GTP-binding protein (RAB11F), putative similar to small GTP-binding protein (RAB11F) GI: 1370151 from (*Lotus japonicus*) | At1g18200 | 2.16 | 2.47 |
| unknown protein similar to hypothetical protein GB: AAF25971 GI: 6714275 from [*Arabidopsis thaliana*]; supported by full-length cDNA: Ceres: 257053. | At1g32740 | 2.00 | 2.46 |
| unknown protein; supported by full-length cDNA: Ceres: 28529. | At2g37750 | 1.82 | 2.42 |
| hypothetical protein | At4g01640 | 1.74 | 2.38 |
| superoxide dismutase (EC 1.15.1.1) (Fe)(fragment); supported by full-length cDNA: Ceres: 32935. | At4g25100 | 4.45 | 2.37 |
| Putative protein RNA-directed DNA polymerase, *Arabidopsis thaliana* retrotransposon Ta11-1, PIR2: S65812 | At4g26360 | 2.03 | 2.36 |
| putative protein similar to unknown protein (gb|AAC80617.1) | At5g16490 | 1.99 | 2.33 |
| Expressed protein; supported by full-length cDNA: Ceres: 93707. | At1g47485 | 2.19 | 2.32 |
| putative protein contains similarity to lectin-like protein kinase | At5g65530 | 1.95 | 2.32 |
| hypothetical protein predicted by genscan | At2g31930 | 1.90 | 2.30 |
| hypothetical protein contains similarity to Avr9 elicitor response protein GI: 4138265 from [*Nicotiana tabacum*] | At1g53290 | 1.99 | 2.28 |
| NAM-like protein no apical meristem (NAM) - *Petunia hybrida*, EMBL: PHDNANAM; supported by full-length cDNA: Ceres: 103969. | At3g61910 | 2.09 | 2.28 |
| MADS box transcription factor-like protein | At5g65080 | 2.03 | 2.27 |
| Expressed protein; supported by full-length cDNA: Ceres: 115850. | At3g12955 | 1.67 | 2.27 |
| putative ras-related GTP-binding protein contains Pfam profile: PF00071 ras family; supported by full-length cDNA: Ceres: 118351. | At1g73640 | 1.92 | 2.25 |
| putative protein putative proteins *Arabidopsis thaliana* | At4g09990 | 2.85 | 2.24 |
| unknown protein similar to multiple exostoses type II protein EXT2.I (U72263); similar to ESTs dbj|D39982, gb|L37635, and dbj|C28418 | At1g27440 | 2.24 | 2.23 |
| peroxidase (emb|CAA66960.1) | At5g42180 | 2.33 | 2.18 |
| putative RING zinc finger protein contains Pfam profile: PF00097 Zinc finger, C3HC4 type (RING finger) | At3g10910 | 1.65 | 2.17 |
| Unknown protein Highly Similar to branched-chain amino acid aminotransferase; Location of EST gb|T21730 and gb|R90237; supported by cDNA: gi_15450873_gb_AY054517.1_ | At1g10060 | 1.47 | 2.16 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| putative protein hypothetical protein T17J13.170-*Arabidopsis thaliana*, PIR: T48013 | At3g61090 | 1.27 | 2.13 |
| lysine decarboxylase - like protein lysine decarboxylase, *Eikenella corrodens*, EMBL: U89166 | At5g11950 | 1.73 | 2.12 |
| response regulator 7, putative similar to response regulator 7 GI: 3953603 from [*Arabidopsis thaliana*]; supported by cDNA: gi_11870064_gb_AF305720.1_AF305720 | At1g74890 | 2.21 | 2.11 |
| unknown protein similar to hypothetical protein GB: CAB39623 | At1g09610 | 1.67 | 2.11 |
| similar to hookless1 (HLS1) | At2g23060 | 1.12 | 2.11 |
| hypothetical protein predicted by genemark.hmm; supported by full-length cDNA: Ceres: 3200. | At1g21050 | 1.16 | 2.10 |
| caffeoyl-CoA O-methyltransferase -like protein caffeoyl-CoA O-methyltransferase, *Pinus taeda*, AF036095; supported by full-length cDNA: Ceres: 33227. | At4g26220 | 2.18 | 2.09 |
| Hypothetical protein identical to hypothetical protein GB: AAD46041 GI: 5668815 from (*Arabidopsis thaliana*) | At1g47410 | 1.67 | 2.08 |
| hypothetical protein predicted by genemark.hmm | At1g19960 | 1.52 | 2.08 |
| putative protein contains similarity to unknown protein (pir|T08924); supported by full-length cDNA: Ceres: 141890. | At5g55970 | 1.57 | 2.06 |
| nodulin-like protein nodulin gene MtN21- *Medicago truncatula*, PID: e1172471 | At4g08300 | 1.57 | 2.06 |
| putative protein (fragment) | At4g18640 | 2.16 | 2.06 |
| putative protein strong similarity to unknown protein (emb|CAB66408.1) | At5g24310 | 2.13 | 2.06 |
| putative protein | At3g45730 | 1.43 | 2.05 |
| putative protein contains similarity to unknown protein (gb|AAF63638.1); supported by cDNA: gi_15983463_gb_AF424606.1_AF424606 | At5g46340 | 2.44 | 2.05 |
| Expressed protein; supported by cDNA: gi_15451225_gb_AY054693.1_ | At5g23860 | 1.77 | 2.04 |
| hypothetical protein predicted by genefinder; supported by full-length cDNA: Ceres: 207066. | At2g01660 | 1.87 | 2.02 |
| putative protein glycogenin glucosyltransferase (EC 2.4.1.186)-human, PID: g1174167 | At4g33330 | 2.16 | 2.01 |
| unknown protein | At2g37090 | 2.06 | 2.00 |
| cytokinin oxidase, putative similar to GB: CAA77151 from [*Zea mays*] (Plant J. 17 (6), 615-626 (1999)) | At1g75450 | 2.43 | 1.99 |
| Hypothetical protein hypothetical protein from *Arabidopsis thaliana* chromosome 1, F7G19.14, PID: g2342684 | At4g33340 | 2.05 | 1.98 |
| glutaredoxin, putative similar to glutaredoxin GB: CAA89699 GI: 1732424 from [*Ricinus communis*]; supported by full-length cDNA: Ceres: 125679. | At1g06830 | 2.53 | 1.98 |
| serine/threonine protein kinase-like | At5g35960 | 2.24 | 1.96 |
| beta-xylosidase | At5g64570 | 2.32 | 1.94 |
| trehalose-phosphatase, putative contains TIGRfamprofile: trehalose-phosphatase; supported by full-length cDNA: Ceres: 255364. | At1g35910 | 2.05 | 1.93 |
| Putative pectinesterase; gi_13605695_gb_AF361829.1_AF361829 | At2g45220 | 2.26 | 1.89 |
| putative multispanning membrane protein similar to MURA transposase of maize Mutator transposon | At2g24170 | 2.37 | 1.89 |
| Putative protein several hypothetical proteins *Arabidopsis thaliana*; supported by full-length cDNA: Ceres: 153592. | At5g01360 | 2.22 | 1.87 |
| extensin-like protein extensin-like protein, *Zea mays*, Pir2: S49915 | At4g28380 | 2.01 | 1.84 |
| Putative pectate lyase pectatelyase, *Musa acuminata*, PATX: E209876; supported by full-length cDNA: Ceres: 36681. | At4g24780 | 2.13 | 1.83 |
| dimethylaniline monooxygenase-like protein | At5g07800 | 2.05 | 1.81 |
| hypothetical protein predicted by genemark.hmm; supported by full-length cDNA: Ceres: 114466. | At1g33800 | 2.01 | 1.79 |
| laccase (diphenol oxidase) | At5g05390 | 2.24 | 1.79 |
| putative PREG1-like negative regulator | At2g44740 | 2.43 | 1.78 |
| unknown protein; supported by full-length cDNA: Ceres: 2767. | At3g25930 | 2.01 | 1.75 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| Farnesylated protein ATFP6-like protein farnesylated protein ATFP6 - *Arabidopsis thaliana*, EMBL: U64909 | At5g17450 | 2.09 | 1.74 |
| putative MYB family transcription factor Pfam HMM hit: Myb DNA-binding proteins; supported by cDNA: gi_15375284_gb_AF214116.2_AF214116 | At1g63910 | 2.44 | 1.67 |
| Putative protein kinase contains a protein kinase domain profile (PDOC00100); supported by cDNA: gi_14334459_gb_AY034921.1_ | At2g40120 | 2.04 | 1.66 |
| hypothetical protein predicted by genefinder | At2g45900 | 2.26 | 1.61 |
| Unknown protein; supported by cDNA: gi_16612242_gb_AF439822.1_AF439822 | At2g35190 | 2.00 | 1.54 |
| putative protein similar to unknown protein (gb|AAF34839.1); supported by cDNA: gi_13926341_gb_AF372918.1_AF372918 | At5g53830 | 2.20 | 1.51 |
| carbonic anhydrase (CAH1); supported by cDNA: gi_15450772_gb_AY054466.1_ | At3g52720 | 2.14 | 1.45 |
| laccase-like protein laccase precursor, *Nicotiana tabacum*, PIR: JC5229 | At5g01190 | 2.07 | 1.43 |
| GASA4; supported by cDNA: gi_950098_gb_U15683.1_ATU15683 | At5g15230 | 2.51 | 1.40 |
| putative protein similar to unknown protein (emb CAB62461.1); supported by full-length cDNA: Ceres: 268701. | At5g24660 | 3.27 | 1.34 |
| ripening-related protein - like grip28 ripening-related protein, *Vitis vinifera*, EMBL: VVI237985; supported by full-length cDNA: Ceres: 1710. | At5g20740 | 2.23 | 1.19 |
| hypothetical protein predicted by genemark.hmm | At1g04770 | 2.19 | 1.09 |
| putative sulphate transporter protein strongly similar to GB: BAA75015, location of EST gb|W43788 and gb|N96564; supported by cDNA: gi_4579912_dbj_AB023423.1_AB023423 | At1g23090 | 0.45 | 0.72 |
| putative protein similarity to various predicted proteins~Contains ATP synthase delta (OSCP) subunit signature AA211-230; Prokaryotic membrane lipoprotein lipid attachment site AA140-150 | At5g12420 | 0.48 | 0.68 |
| hypothetical protein predicted by genscan and genefinder; supported by cDNA: gi_15450730_gb_AY053407.1_ | At2g40130 | 0.46 | 0.66 |
| unknown protein | At5g51680 | 0.43 | 0.66 |
| hypothetical protein predicted by genemark.hmm | At1g30250 | 0.48 | 0.64 |
| phosphoinositide-specific phospholipase C - like protein phosphoinositide-specific phospholipase C, *Arabidopsis thaliana*, PIR: S71170 | At3g55940 | 0.49 | 0.62 |
| hypothetical protein predicted by genefinder and genscan | At1g10990 | 0.48 | 0.61 |
| sugar transport, putative similar to D-XYLOSE-PROTON SYMPORTER GB: O52733 from [*Lactobacillus brevis*] | At3g18830 | 0.49 | 0.58 |
| auxin-induced protein, putative similar to auxin-induced atb2 GI: 6562980 from [*Arabidopsis thaliana*]; supported by cDNA: gi_13605500_gb_AF361576.1_AF361576 | At1g60730 | 0.49 | 0.57 |
| serine/threonine kinase-like protein KI domain interacting kinase 1 (KIK1), *Zea mays* | At4g23150 | 0.45 | 0.57 |
| endochitinase isolog | At2g43570 | 0.42 | 0.55 |
| putative protein similar to unknown protein (pir||T05562); supported by full-length cDNA: Ceres: 158397. | At5g50200 | 0.46 | 0.52 |
| Putative cytochrome P450 monooxygenase identical togb|X97864 cytochrome P450 from *Arabidopsis thaliana* and is a member of the PF|00067 Cytochrome P450 family. ESTs gb|T44875, gb|T04814, gb|R65111, gb|T44310 and gb|T04541 come from this gene | At1g13110 | 0.41 | 0.52 |
| putative protein similar to unknown protein (emb CAB62355.1) | At5g40960 | 0.45 | 0.52 |
| hevein-like protein precursor (PR-4) identical to hevein-like protein precursor GB: P43082 [*Arabidopsis thaliana*], similar to wound-induced protein (WIN2) precursor GB: P09762 [*Solanum tuberosum*]; Pfam HMM hit: chitin_binding proteins; supported by full-length cDNA: Ceres: 8793. | At3g04720 | 0.47 | 0.51 |
| protein kinase- like protein KI domain interacting kinase- *Zea mays*, PIR2: T02053 | At4g11890 | 0.38 | 0.51 |
| male sterility protein 2 (MS2) nearly identical to male sterility protein 2 (MS2) SP: Q08891 (*Arabidopsis thaliana* (Mouse-ear cress)) | At3g11980 | 0.49 | 0.51 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| putative ammonium transporter | At2g38290 | 0.49 | 0.50 |
| unknown protein similar to T11A07.9 | At2g41800 | 0.35 | 0.50 |
| amino acid permease-like protein; proline transporter-like protein; supported by full-length cDNA: Ceres: 20725. | At5g41800 | 0.65 | 0.50 |
| Putative receptor protein kinase receptor protein kinase, *Ipomoea trifida*, PID: g836954 | At4g27300 | 0.51 | 0.50 |
| polygalacturonase, putative similar to polygalacturonase GI: 7381227 from [*L. esculentum*]; supported by cDNA: gi_15028104_gb_AY046002.1_ | At1g80170 | 0.47 | 0.50 |
| nucleoid DNA-binding protein cnd41 - like protein nucleoid DNA-binding protein cnd41, chloroplast, common tobacco, PIR: T01996 | At5g10760 | 0.52 | 0.50 |
| putative protein diacylglycerol kinase iota - *Homo sapiens*, PID: g3676530; supported by cDNA: gi_13430523_gb_AF360174.1_AF360174 | At4g30340 | 0.61 | 0.50 |
| putative protein diacylglycerol kinase iota - *Homo sapiens*, PID: g3676530; supported by cDNA: gi_13430523_gb_AF360174.1_AF360174 | At4g30340 | 0.61 | 0.50 |
| Respiratory burst oxidase protein; supported by cDNA: gi_3242788_gb_AF055357.1_AF055357 | At5g47910 | 0.86 | 0.50 |
| ATP-sulfurylase; supported by cDNA: gi_459143_gb_U06275.1_ATU06275 | At4g14680 | 0.99 | 0.49 |
| putative cellulose synthase catalytic subunit similar to cellulose synthase catalytic subunit GB: AAD40885 from [*Arabidopsis thaliana*]; supported by cDNA: gi_12619787_gb_AF232907.1_AF232907 | At3g03050 | 0.81 | 0.49 |
| putative ABC transporter related to multi drug resistance proteins and P- glycoproteins | At2g36380 | 0.55 | 0.49 |
| glutathione S-transferase (GST6) identical to GB: X95295. Based on identical cDNA hits, the translation is now 40 AAs longer at the N-terminal, and start of exon2 is also corrected.; supported by cDNA: gi_14532561_gb_AY039905.1_ | At2g47730 | 0.70 | 0.49 |
| putative pollen surface protein endosperm specific protein - *Zea mays*, PID: g2104712; supported by full-length cDNA: Ceres: 4620. | At4g12730 | 0.98 | 0.49 |
| AIG2-like protein similar to AIG2 protein GB: P54121 from [*Arabidopsis thaliana*]; supported by full-length cDNA: Ceres: 28511. | At3g28930 | 0.55 | 0.49 |
| integral membrane protein, putative similar to GI: 1209755 from [*Beta vulgaris*] (Plant Physiol. 110 110 (2), 511-520 (1996)); supported by cDNA: gi_15724239_gb_AF412060.1_AF412060 | At1g75220 | 0.70 | 0.49 |
| putative protein similar to unknown protein (embl CAB71094.1) | At5g53250 | 0.83 | 0.49 |
| putative Na+/Ca2+ antiporter; supported by cDNA: gi_6492236_gb_AF109178.1_AF109178 | At2g47600 | 0.58 | 0.49 |
| putative endochitinase | At2g43580 | 0.40 | 0.49 |
| hypothetical protein predicted by genemark.hmm; supported by full-length cDNA: Ceres: 2030. | At1g52720 | 0.72 | 0.49 |
| calcium lipid binding protein - like GC donor splice site at exon 3; supported by cDNA: gi_16604592_gb_AY059741.1_ | At5g04220 | 0.53 | 0.49 |
| protein kinase, putative similar to many predicted protein kinases | At1g35710 | 0.46 | 0.49 |
| nodulin/glutamate-ammonia ligase - like protein MtN6 - nodulin 6, *Medicago truncatula*, EMBL: MET133118 | At3g53180 | 0.54 | 0.49 |
| receptor-like kinase, putative similar to receptor-like kinase GI: 1783311 from [*Brassica oleracea*] | At1g61610 | 0.73 | 0.49 |
| Argininosuccinate synthase -like protein argininosuccinate synthase, *Aquifex aeolicus*, PIR2: B70398 | At4g24830 | 0.77 | 0.49 |
| putative aquaporin (water channel protein); supported by cDNA: gi_15010777_gb_AY045690.1_ | At2g39010 | 0.61 | 0.49 |
| putative hydrolase; supported by cDNA: gi_15982855_gb_AY057535.1_ | At2g32150 | 0.76 | 0.48 |
| receptor-like serine/threonine kinase, putative similar to receptor-like serine/threonine kinase GI: 2465923 from [*Arabidopsis thaliana*]; supported by cDNA: gi_16649102_gb_AY059921.1_ | At1g16670 | 0.70 | 0.48 |
| syntaxin-like protein synt4; supported by full-length cDNA: Ceres: 37248. | At3g52400 | 0.89 | 0.48 |

TABLE 2-continued

Genes changed more than 2-fold in two independent Atwrky12-1 and
Atwrky12-2 plants compared to wild type Col-0 control ("CK")

| Target Description | Public ID | Wrky12-1/CK | Wrky12-2/CK |
|---|---|---|---|
| Fatty acid elongase 3-ketoacyl-CoA synthase, putative Similar to GB: AAC99312 from [*Arabidopsis thaliana*]; supported by cDNA: gi_16226846_gb_AF428349.1_AF428349 | At1g07720 | 0.53 | 0.48 |
| nodulin - like protein nodulin, *Glycine max*, EMBL: AF065435 | At5g25260 | 0.43 | 0.48 |
| neutral invertase, putative similar to neutral invertase GB: CAA76145 from [*Daucus carota*] (Physiol. Plantarum (1999) 107, 159-165) | At3g06500 | 0.86 | 0.48 |
| Protein kinase-like protein Pto kinase interactor 1 - *Lycopersicon esculentum*, EMBL: U28007; supported by cDNA: gi_15451117_gb_AY054639.1_ | At3g59350 | 0.64 | 0.48 |
| putative AP2 domain transcription factor contains Pfam profile: PF00847 AP2 domain; supported by cDNA: gi_16604674_gb_AY059782.1_ | At1g68550 | 0.65 | 0.48 |
| putative cyclic nucleotide-regulated ion channel protein | At2g46440 | 0.49 | 0.48 |
| putative GDSL-motif lipase/acylhydrolase contains Pfampr lipase/acylhydrolase with GDSL-like motif; supported by full-length cDNA: Ceres: 1323. | At3g04290 | 0.54 | 0.48 |
| hypothetical protein predicted by genscan | At2g22020 | 0.65 | 0.48 |
| GSH-dependent dehydroascorbate reductase 1, putative similar to GB: BAA90672 from [*Oryza sativa*]; supported by full-length cDNA: Ceres: 15122. | At1g19570 | 0.72 | 0.48 |
| putative protein predicted proteins, *Arabidopsis thaliana*; supported by full- length cDNA: Ceres: 32414. | At5g18490 | 0.56 | 0.48 |
| calcium-dependent protein kinase, putative similar to calcium-dependent protein kinase GI: 604880 from [*Arabidopsis thaliana*]; supported by cDNA: gi_1235716_dbj_D21805.1_ATHCDPKA | At1g18890 | 0.71 | 0.48 |
| flavanone 3-hydroxylase-like protein; supported by full-length cDNA: Ceres: 149654. | At5g24530 | 0.37 | 0.48 |
| Putative protein kinase contains a protein kinase domain Profile (PDOC00100); supported by cDNA: gi_14335115_gb_AY037237.1_ | At2g48010 | 0.74 | 0.48 |
| senescence-associated protein 5-like protein | At5g46700 | 0.91 | 0.48 |
| hypothetical protein predicted by genscan+; supported by full-length cDNA: Ceres: 113990. | At1g30840 | 0.58 | 0.47 |
| Hypothetical protein similar to hypothetical protein GB: AAC61817; GI: 3668085 from [*Arabidopsis thaliana*] | At1g32690 | 0.84 | 0.47 |
| pectinesterase, putative similar to pectinesterase GI: 732912 from [*Phaseolus vulgaris*]; supported by full-length cDNA: Ceres: 41374. | At1g53840 | 0.93 | 0.47 |
| putative protein; supported by full-length cDNA: Ceres: 12522. | At3g57450 | 0.88 | 0.47 |
| putative beta-amylase; supported by full-length cDNA: Ceres: 36882. | At4g17090 | 0.86 | 0.47 |
| putative protein component of aniline dioxygenase (GMP synthase like protein - *Acinetobacter* sp., PID: d1013698; supported by full-length cDNA: Ceres: 37987. | At4g30530 | 0.68 | 0.47 |
| putative pectinesterase | At2g26440 | 0.59 | 0.47 |
| Ca2+-transporting ATPase-like protein Ca2+-transporting ATPase, calmodulin-stimulated - *Brassica oleracea*, PIR: T14453 | At3g57330 | 0.67 | 0.47 |
| protein kinase identical to protein kinase GI: 2852447 from [*Arabidopsis thaliana*]; supported by cDNA: gi_2852446_dbj_D88206.1_D88206 | At1g14370 | 0.55 | 0.47 |
| 3(2),5-bisphosphate nucleotidase; supported by cDNA: gi_15281147_gb_AY034894.1_ | At5g63980 | 1.11 | 0.47 |
| beta-galactosidase; supported by cDNA: gi_15027868_gb_AY045791.1_ | At5g20710 | 0.41 | 0.47 |
| protein phosphatase type 2C, putative similar to GB: AAD17805 from (*Lotus japonicus*) (Proc. Natl. Acad. Sci. U.S.A. 96 (4), 1738-1743 (1999)) | At1g34750 | 0.59 | 0.47 |
| putative transcription factor; supported by cDNA: gi_15450989_gb_AY054575.1_ | At4g01680 | 0.65 | 0.47 |
| unknown protein; supported by full-length cDNA: Ceres: 114031. | At2g38860 | 0.52 | 0.47 |
| receptor protein kinase-like protein receptor protein kinase-like protein - *Arabidopsis thaliana*, PIR2: T05898 | At4g08850 | 0.57 | 0.47 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| putative glucosyltransferase | At2g30140 | 0.55 | 0.47 |
| carbonic anhydrase, putative similar to carbonic anhydrase GI: 882241 from [*Flaveria linearis*]; supported by full-length cDNA: Ceres: 38715. | At1g70410 | 0.74 | 0.46 |
| putative protein putative proteins from *Arabidopsis thaliana*; supported by cDNA: gi_17063190_gb_AY062118.1_ | At4g27860 | 0.64 | 0.46 |
| ethylene responsive element binding factor 4 GB: BAA32421 from [*Arabidopsis thaliana*]; supported by full-length cDNA: Ceres: 22775. | At3g15210 | 0.58 | 0.46 |
| unknown protein | At1g17340 | 0.67 | 0.46 |
| hypothetical protein predicted by genefinder | At1g70700 | 0.70 | 0.46 |
| putative WRKY-type DNA binding protein; supported gi_15027912_gb_AY045813.1_ | At2g30250 | 0.59 | 0.46 |
| putative protein PrMC3, *Pinus radiata*, EMBL: AF110333 | At3g63010 | 0.63 | 0.46 |
| putative protein myosin heavy chain-B, neuronal - *Gallus gallus*, PIR: B43402; supported by cDNA: gi_13430501_gb_AF360163.1_AF360163 | At4g32190 | 0.66 | 0.46 |
| similar to cold acclimation protein WCOR413 [*Triticum aestivum*] | At2g23680 | 0.58 | 0.46 |
| defensin AMP1, putative similar to PIR: S66219 from [*Clitoria ternatea*] | At1g19610 | 0.47 | 0.46 |
| MTN3-like protein MtN3 gene product - *Medicago truncatula*, PID: e1169583; supported by cDNA: gi_13605687_gb_AF361825.1_AF361825 | At3g48740 | 0.81 | 0.46 |
| hydroxynitrile lyase like protein | At4g37150 | 0.62 | 0.46 |
| putative leucine-rich receptor protein kinase 34% identical to leucine-rich receptor-like protein kinase [*Ipomoea nil*] (gi|1684913) and 35% identical to leucine-rich receptor-like protein kinase [*Malus domestica*] (gi|3641252) | At1g17230 | 0.61 | 0.46 |
| peroxidase; supported by full-length cDNA: Ceres: 39678. | At3g49120 | 0.61 | 0.46 |
| putative myrosinase-binding protein; supported by full-length cDNA: Ceres: 39069. | At2g39330 | 0.95 | 0.46 |
| contains weak similarity to *S. cerevisiae* BOB1 protein (PIR: S45444) | At4g00300 | 0.65 | 0.46 |
| putative protein strong similarity to unknown protein (gb|AAF01562.1) | At5g63970 | 1.00 | 0.46 |
| unknown protein; supported by full-length cDNA: Ceres: 3024. | At1g74950 | 0.93 | 0.46 |
| hypothetical protein predicted by genemark.hmm | At1g65510 | 0.51 | 0.46 |
| putative protein similar to unknown protein (gb AAF01580.1) | At5g23510 | 0.61 | 0.45 |
| Putative protein contains similarity to squamosa promoter binding protein; supported by full-length cDNA: Ceres: 113229. | At5g50570 | 0.81 | 0.45 |
| putative ligand-gated ion channel subunit; supported bycDNA gi_6644387_gb_AF210701.1_AF210701 | At2g32400 | 0.73 | 0.45 |
| serine acetyltransferase (Sat-1) identical to serine acetyltransferase (Sat-1) GB: U22964 [*Arabidopsis thaliana*] (Plant Mol. Biol. 30 (5), 1041-1049 (1996)); supported by cDNA: gi_1184047_gb_U22964.1_ATU22964 | At3g13110 | 0.76 | 0.45 |
| unknown protein; supported by full-length cDNA: Ceres: 9221. | At3g05490 | 0.82 | 0.45 |
| unknown protein; supported by full-length cDNA: Ceres: 125631. | At2g30930 | 0.54 | 0.45 |
| nodulin-like protein | At2g16660 | 0.42 | 0.45 |
| resistance protein, putative similar to resistance protein MG23 GI: 9858478 from [*Glycine max*] | At1g61100 | 0.66 | 0.45 |
| putativeprotein kinase contains a protein kinase | At2g17220 | 0.67 | 0.44 |
| putative protein contains EST gb: T4504800 | At4g25620 | 0.84 | 0.44 |
| sexual differentiation process protein ISP4-like | At5g55930 | 0.51 | 0.44 |
| putative protein similar to unknown protein (gb|AAD04946.2) | At5g06570 | 0.41 | 0.44 |
| putative trypsin inhibitor; supported by full-length cDNA: Ceres: 85. | At2g43550 | 0.81 | 0.44 |
| probable cytochrome P450 | At4g00360 | 0.52 | 0.44 |
| putative thromboxane-A synthase; supported by cDNA: gi_15810029_gb_AY054283.1_ | At2g26170 | 0.52 | 0.44 |
| putative protein EREBP-3 homolog, *Stylosanthes hamata*, EMBL: U91982; supported by cDNA: gi_15010555_gb_AY045579.1_ | At3g50260 | 0.67 | 0.44 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| Unknown protein Similar to *A. thaliana* receptor-like Protein kinase (gb\|RLK5_ARATH). ESTs gb\|ATTS0475, gb\|ATTS4362 come from this gene | At1g09970 | 0.54 | 0.43 |
| unknown protein similar to hypotheticalprotein GB: CAA10 *arietinum*]; supported by full-length cDNA: Ceres: 108086. | At3g01290 | 0.49 | 0.43 |
| putative protein phytochrome-associated protein 1, *Arabidopsis thaliana*, EMBL: AF088281; supported by full-length cDNA: Ceres: 2499. | At5g25890 | 0.52 | 0.43 |
| putative lectin contains Pfam profile: PF01419 jacalin-like lectin domain; similar to jasmonate inducible protein GB: Y11483 (*Brassica napus*), myrosinase binding protein GB: BAA84545 (*Arabidopsis thaliana*); supported by full-length cDNA: Ceres: 30003. | At3g16470 | 0.73 | 0.43 |
| oxidoreductase, putative contains Pfam profile: PF00671 Iron/Ascorbate oxidoreductase family; supported by cDNA: gi_13430545_gb_AF360185.1_AF360185 | At1g06640 | 0.75 | 0.43 |
| methionine/cystathionine gamma lyase, putative similar to methionine gamma-lyase GB: CAA04124.1 GI: 2330885 from [*Trichomonas vaginalis*]; supported by cDNA: gi_15450931_gb_AY054546.1_ | At1g64660 | 0.51 | 0.43 |
| polygalacturonase inhibiting protein 1; PGIP1 (gb\|AAF69827.1); supported by full-length cDNA: Ceres: 5344. | At5g06860 | 0.75 | 0.43 |
| putative protein similar to unknown protein (pir\|T04500) | At5g43180 | 0.40 | 0.43 |
| Serine carboxypeptidase isolog | At1g11080 | 0.32 | 0.43 |
| Putativeselenocysteine methyltransferase similar to selenocysteine methyltransferase GB: P56707 from [*Astragalus bisulcatus*]; supported by full-length cDNA: Ceres: 36591. | At3g22740 | 0.67 | 0.43 |
| putative calmodulin-binding protein calmodulin-binding protein, *Nicotiana tabacum* | At4g31000 | 0.74 | 0.43 |
| unknown protein; supported by cDNA: gi_15146182_gb_AY049232.1_ | At3g27210 | 0.64 | 0.43 |
| putative protein strong similarity to unknown protein (pir\|\|T04808) | At5g55120 | 0.84 | 0.43 |
| putative GDSL-motif lipase/hydrolase similar to APG proteins; pFAM domain PF00657; supported by full-length cDNA: Ceres: 121397. | At2g03980 | 0.60 | 0.42 |
| anthranilate synthase component I-1 precursor (sp\|P32068) | At5g05730 | 0.78 | 0.42 |
| anthranilate phosphoribosyltransferase, chloroplast precursor (sp\|Q02166); supported by cDNA: gi_15450851_gb_AY054506.1_ | At5g17990 | 0.56 | 0.42 |
| unknown protein; supported by full-length cDNA: Ceres: 99625. | At1g66180 | 0.68 | 0.42 |
| lipase, putative similar to lipase GI: 1145627 from [*Arabidopsis thaliana*] | At1g53990 | 0.42 | 0.42 |
| Putative protein several hypothetical proteins-*Arabidopsis thaliana*; supported by cDNA: gi_15320409_dbj_AB039927.1_AB039927 | At4g19120 | 0.65 | 0.42 |
| Carboxyphosphonoenolpyruvate mutase, putative similar to Carboxyphosphonoenolpyruvate mutase GI: 47149 from [*Streptomyces hygroscopicus*]; supported by full-length cDNA: Ceres: 12293. | At1g77060 | 0.74 | 0.42 |
| lysophospholipase isolog, putative similar to lysophospholipase isolog GI: 1931639 from (*Arabidopsis thaliana*); supported by full-length cDNA: Ceres: 105948. | At1g77420 | 0.64 | 0.42 |
| disease resistance protein, putative similar to disease resistance protein GI: 9758876 from [*Arabidopsis thaliana*] | At1g72940 | 0.89 | 0.42 |
| transporter-like protein | At5g13740 | 0.56 | 0.41 |
| hypothetical protein predicted by genemark.hmm | At1g02900 | 0.49 | 0.41 |
| putative LRR receptor-like protein kinase similar to *Z. mays* leucine-rich repeat transmembrane protein kinase LRRTPK 1, GenBank accession number AF023164 | At4g03390 | 0.52 | 0.41 |
| ACC synthase (AtACS-6); supported by cDNA: gi_16226285_gb_AF428292.1_AF428292 | At4g11280 | 0.85 | 0.41 |
| unknown protein | At2g03240 | 0.84 | 0.41 |
| unknown protein predicted by genscan | At2g24330 | 0.82 | 0.41 |
| dehydrin Xero2; supported by cDNA: gi_15809983_gb_AY054260.1_ | At3g50970 | 0.55 | 0.41 |
| putative protein | At4g39840 | 0.58 | 0.41 |
| Expressed protein; supported by full-length cDNA: Ceres: 59. | At5g19875 | 0.61 | 0.41 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| fatty acid elongase 3-ketoacyl-CoA synthase 1 identical to GB: AAC99312 GI: 4091810 from [*Arabidopsis thaliana*] | At1g01120 | 0.65 | 0.41 |
| glutathione S-transferase, putative similar to glutathione S-transferase GI: 860955 from [*Hyoscyamus muticus*]; supported by cDNA: gi_15215607_gb_AY050332.1_ | At1g02930 | 0.38 | 0.41 |
| calcium-binding protein-like calcium-binding protein, *Solanum tuberosum*, gb: L02830 | At4g20780 | 0.44 | 0.40 |
| cysteine proteinase inhibitor like protein; supported by full-length cDNA: Ceres: 31946. | At4g16500 | 0.59 | 0.40 |
| phytochrome-associated protein 1 (PAP1) nearly identical to phytochrome-associated protein 1 (PAP1) GB: AF088281 [*Arabidopsis thaliana*] (sequence discrepancy at (232-242 (this): 213-217 (GB: AF088281))); supported by full-length cDNA: Ceres: 38146. | At3g16500 | 0.50 | 0.40 |
| phi-1-like protein; supported by full-length cDNA: Ceres: 37357. | At5g64260 | 0.72 | 0.40 |
| Potassium channel protein AKT3; supported by cDNA: gi_1100897_gb_U40154.1_ATU40154 | At4g22200 | 0.62 | 0.40 |
| cytochrome P450 | At5g45340 | 0.63 | 0.40 |
| 2-hydroxyisoflavone reductase, putative similar to PIR: T08106 from [*Betula pendula*] | At1g19540 | 0.47 | 0.40 |
| putative peroxidase | At2g41480 | 0.55 | 0.40 |
| unknown protein; supported by cDNA: gi_16323164_gb_AY057686.1_ | At2g41180 | 0.32 | 0.40 |
| putative protein paladin - *Mus musculus*, EMBL: MMPAL | At3g62010 | 0.69 | 0.40 |
| Pectin methylesterase, putative similar to pectin methylesterase GI: 1617583 from [*Lycopersicon esculentum*]; supported by cDNA: gi_14334991_gb_AY037175.1_ | At1g11580 | 0.62 | 0.40 |
| unknown protein | At1g31550 | 0.93 | 0.40 |
| receptor protein kinase-like | At5g49760 | 0.51 | 0.40 |
| lipid transfer protein, putative contains Pfam profile: PF00279: Plant lipid transfer protein family; supported by full-length cDNA: Ceres: 15027. | At1g27950 | 0.50 | 0.39 |
| putative protein kinase similar to protein kinase (APK1A) GB: Q06548 [*Arabidopsis thaliana*]; contains Pfam profile: PF00069 Eukaryotic protein kinase domain | At3g09830 | 0.64 | 0.39 |
| subtilisin-like serine protease similar to subtilisin-type protease precursor GI: 14150446 from [*Glycine max*]; supported by full-length cDNA: Ceres: 3907. | At1g20160 | 0.61 | 0.39 |
| tryptophan synthase alpha chain; supported by full-length cDNA: Ceres: 40110. | At3g54640 | 0.53 | 0.39 |
| myb-related protein, 33.3K (pir|S71284); supported by full-length cDNA: Ceres: 33763. | At5g67300 | 0.77 | 0.39 |
| putative protein amino acid transport protein - *Arabidopsis thaliana*, EMBL: U39783 | At5g02170 | 0.54 | 0.39 |
| Putative phosphatidylinositol-4-phosphate 5-kinase similar to phosphatidylinositol-4-phosphate 5-kinase GB: CAB53377 [*Arabidopsis thaliana*] | At3g09920 | 0.45 | 0.39 |
| unknown protein | At1g30040 | 0.43 | 0.39 |
| unknown protein | At3g19680 | 0.59 | 0.38 |
| shaggy-like kinase beta | At3g61160 | 0.59 | 0.38 |
| putative phospholipase | At2g39420 | 0.54 | 0.38 |
| scarecrow-like 13 (SCL13); gi_16930432_gb_AF419570.1_AF419570 | At4g17230 | 0.69 | 0.38 |
| putative protein cim1 induced allergen, *Glycine max*, EMBL: U03860 | At3g45960 | 0.69 | 0.38 |
| Protein serine/threonine kinase-like protein putative protein serine/threonine kinase - *Sorghum bicolor*, EMBL: Y14600 | At5g10290 | 0.67 | 0.38 |
| receptor like protein kinase receptor like protein kinase, *Arabidopsis thaliana*, EMBL: AL138657; supported by cDNA: gi_15810556_gb_AY056317.1_ | At5g60300 | 0.53 | 0.38 |
| Putative protein DNA damage-inducible protein - *Synechocystis* sp., PIR2: S77364 | At4g39030 | 0.54 | 0.37 |
| cellulose synthase catalytic subunit -like protein Ath-B, cellulose synthase catalytic subunit, *Arabidopsis thaliana*, EMBL: AF027174 | At5g16910 | 0.62 | 0.37 |
| serine threonine kinase - like protein KI domain interacting kinase 1 (KIK1), *Zea mays*; supported by cDNA: gi_13506746_gb_AF224706.1_AF224706 | At4g23140 | 0.32 | 0.37 |
| Hypothetical protein predicted by genscan; supported by cDNA: gi_13937239_gb_AF372975.1_AF372975 | At1g10340 | 0.55 | 0.37 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| putative protein | At4g33050 | 0.58 | 0.37 |
| unknown protein; supported by full-length cDNA: Ceres: 94974. | At1g06520 | 0.24 | 0.37 |
| glycine-rich protein glycine-rich cell wall structural protein petunia, Pir2: A26099 | At4g30460 | 0.55 | 0.37 |
| thioredoxin, putative similar to thioredoxin GI: 992966 from [Arabidopsis thaliana]; supported by full-length cDNA: Ceres: 3236. | At1g45145 | 0.53 | 0.36 |
| unknown protein | At3g25890 | 0.58 | 0.36 |
| putative protein several hypothetical Na(+)/H(+) antiporter | At3g53720 | 0.38 | 0.36 |
| NAM-like protein similar to NAM (no apical meristem) GB: CAA63101 from [Petunia x hybrida] | At1g52890 | 0.90 | 0.36 |
| hypothetical protein predicted by genefinder | At2g30990 | 0.60 | 0.36 |
| adenylosuccinate lyase - like protein adenylosuccinate lyase - Haemophilus influenzae | At4g18440 | 0.58 | 0.36 |
| putative protein; supported by full-length cDNA: Ceres: 113484. | At4g27720 | 0.55 | 0.36 |
| Anthranilate synthase beta chain; supported by full-length cDNA: Ceres: 6495. | At5g57890 | 0.71 | 0.36 |
| unknown protein; supported by full-length cDNA: Ceres: 25136. | At1g65500 | 0.42 | 0.36 |
| putative galactinol synthase; supported by full-length cDNA: Ceres: 124236. | At2g47180 | 0.64 | 0.36 |
| Expressed protein; supported by full-length cDNA: Ceres: 32450. | At5g35735 | 0.79 | 0.36 |
| putative indole-3-glycerol phosphate synthase; supported by cDNA: Ceres: 3006. | At2g04400 | 0.59 | 0.36 |
| putative lectin contains Pfam profile: PF01419 jacalin-like lectin domain; similar to jasmonate inducible protein GB: Y11483 (Brassica napus), myrosinase binding protein GB: BAA84545 (Arabidopsis thaliana) | At3g16390 | 0.53 | 0.36 |
| putative protein auxin-induced basic helix-loop-helix transcription factor, Gossypium hirsutum, EM BL: AF165924; supported by cDNA: gi_15724267_gb_AF412074.1_AF412074 | At5g08330 | 0.99 | 0.36 |
| putative protein ENOD20 gene, Medicago truncatula, X99467; supported by full-length cDNA: Ceres: 33380. | At4g27520 | 0.72 | 0.35 |
| putative protein UDP-glucose: (glucosyl) LPS alpha1,3-glucosyltransferase WaaO, E. coli, EMBL: AF019746 | At3g50760 | 0.61 | 0.35 |
| Vegetative storage protein-like; supported by full-length cDNA: Ceres: 27372. | At5g44020 | 0.65 | 0.35 |
| Membrane related protein-like; supported by full-length cDNA: Ceres: 37644. | At5g54170 | 0.63 | 0.35 |
| putative protein SF16 protein, Helianthus annuus, PID: g560150 | At4g23060 | 0.48 | 0.35 |
| putative lectin similar to lectin SP: P02874 [Onobrychis viciifolia]; contains Pfam profile: PF00139 legume lectins beta domain; supported by cDNA: gi_15809853_gb_AY054194.1_ | At3g16530 | 0.38 | 0.35 |
| Putative protein peroxisomal integral membrane protein- Homo sapiens; supported by full-length cDNA: Ceres: 20865. | At5g27520 | 0.74 | 0.35 |
| beta-ketoacyl-ACP reductase - like protein beta-ketoacyl-ACP reductase, Cuphea lanceolata, EMBL: X64566 | At3g55310 | 0.41 | 0.35 |
| peptide methionine sulfoxide reductase-like protein peptide methionine sulfoxide reductase (msr) - Arabidopsis thaliana, EMBL: AJ133753 | At5g07460 | 0.47 | 0.35 |
| putative disease resistance protein similar to putative disease resistance protein GB: AAF01514 from clone F9F8 | At3g05650 | 0.60 | 0.35 |
| Putative protein male sterility protein 2 - Arabidopsis thaliana, EMBL: X73652 | At3g56700 | 0.68 | 0.35 |
| Gibberellin regulatory protein, putative similar to GB: CAA75492 from [Arabidopsis thaliana]; supported by cDNA: gi_15777856_gb_AY048749.1_ | At1g66350 | 0.58 | 0.35 |
| nitrate reductase 1 (NR1) identical to nitrate reductase 1 (NR1) GB: P11832 [Arabidopsis thaliana]; supported by cDNA: gi_15983498_gb_AF424624.1_AF424624 | At1g77760 | 0.79 | 0.34 |
| MYB27 protein - like MYB27 protein, Arabidopsis thaliana, PIR: T46166; supported by cDNA: gi_3941479_gb_AF062894.1_AF062894 | At5g59780 | 0.61 | 0.34 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| beta-fructofuranosidase 1 identical to GB: S37212 from [*Arabidopsis thaliana*]; supported by cDNA: gi_15027838_gb_AY045776.1_ | At3g13790 | 0.24 | 0.34 |
| protein kinase, putative identical to bHLH protein GB: CAA67885 GI: 1465368 from [*Arabidopsis thaliana*]; supported by cDNA: gi_14335047_gb_AY037203.1_ | At1g32640 | 0.83 | 0.33 |
| integral membrane protein-like | At5g52050 | 0.54 | 0.33 |
| peptide transporter | At5g62680 | 0.59 | 0.33 |
| glycine-rich protein glycine-rich cell wall structural protein - *Petunia x hybrida*, Pir2: A26099; supported by full-length cDNA: Ceres: 115209. | At4g30450 | 0.62 | 0.33 |
| Putative trypsin inhibitor; gi_15292710_gb_AY050789.1_ | At2g43510 | 0.31 | 0.33 |
| mutT domain protein-like; supported by full-length cDNA: Ceres: 38400. | At5g47240 | 0.71 | 0.33 |
| Monogalactosyldiacylglycerol synthase-like protein Monogalactosyldiacylglycerol synthase, *Cucumis sativus*, PID: g1805254; supported by cDNA: gi_7621496_gb_AF241797.1_AF241797 | At4g31780 | 0.65 | 0.33 |
| 1-a minocyclopropane-1-carboxylate oxidase, putative similar to 1-aminocyclopropane-1-carboxylate oxidase GI: 3386565 from [*Sorghum bicolor*]; supported by full-length cDNA: Ceres: 269582. | At1g77330 | 0.26 | 0.33 |
| cytochrome P450; supported by cDNA: gi_3164141_dbj_D78606.1_D78606 | At5g36220 | 0.63 | 0.33 |
| ER lumen protein retaining receptor identical to SP: P35402 from (*Arabidopsis thaliana*) | At1g29330 | 0.55 | 0.32 |
| abscisic acid-induced-like protein abscisic acid-induced protein HVA22, *Hordeum vulgare*, PIR2: A48892; supported by full-length cDNA: Ceres: 28535. | At4g24960 | 0.39 | 0.32 |
| putative AP2 domain transcription factor pFAM domain (PF00847) | At2g36450 | 0.47 | 0.32 |
| putative protein; supported by full-length cDNA: Ceres: 100165. | At4g19450 | 0.67 | 0.32 |
| P-glycoprotein-like protein P-glycoprotein-2-EMBL: Y10228 | At3g62150 | 0.41 | 0.32 |
| unknown protein; supported by full-length cDNA: Ceres: 12707. | At3g17860 | 0.58 | 0.32 |
| unknown protein | At3g23550 | 0.24 | 0.32 |
| lipase/hydrolase, putative contains Pfam profile: PF00657 Lipase/Acylhydrolase with GDSL-like motif; supported by full-length cDNA: Ceres: 23556. | At1g29670 | 0.59 | 0.32 |
| lipase, putative contains Pfam profile: PF00657 Lipase/Acylhydrolase with GDSL-like motif; supported by full-length cDNA: Ceres: 37307. | At1g28600 | 0.52 | 0.32 |
| putative protein neuronal glutamine transporter - *Rattus norvegicus*, EMBL: AF075704 | At3g56200 | 0.60 | 0.31 |
| putative chitinase similar to peanut type II chitinase, GenBank accession number X82329, E.C. 3.2.1.14 | At4g01700 | 0.34 | 0.31 |
| auxin regulated protein IAA18, putative similar to auxin regulated protein IAA18 GI: 2618725 from [*Arabidopsis thaliana*]; supported by full-length cDNA: Ceres: 6493. | At1g51950 | 0.59 | 0.31 |
| putative protein At2g42580 - *Arabidopsis thaliana*, EMBL: AC007087 | At3g58620 | 0.46 | 0.30 |
| nucleoid DNA-binding - like protein nucleoid DNA-binding protein cnd41, chloroplast, common tobacco, PIR: T01996; supported by full-length cDNA: Ceres: 8987. | At3g54400 | 0.37 | 0.30 |
| hypothetical protein predicted by genemark.hmm | At1g78860 | 0.66 | 0.30 |
| beta-1,3-glucanase 2 (BG2) (PR-2); supported by full-length cDNA: Ceres: 21719. | At3g57260 | 0.30 | 0.30 |
| myrosinase-associated protein, putative similar to myrosinase-associated protein GI: 1769967 from [*Brassica napus*]; supported by cDNA: gi_15809979_gb_AY054258.1_ | At1g54020 | 0.72 | 0.29 |
| lysophospholipase - like protein lysophospholipase homolog LPL1, *Oryza sativa*, EMBL: AF039531; supported by full-length cDNA: Ceres: 15284. | At5g11650 | 0.56 | 0.29 |
| Putative protein S-receptor kinase PK3 precursor, maize, | At5g18470 | 0.55 | 0.29 |
| Putative protein storage protein - *Populus deltoides*, PIR2: S31580; supported by full-length cDNA: Ceres: 8772. | At4g24340 | 0.65 | 0.24 |
| hypothetical protein | At1g14780 | 0.35 | 0.24 |

TABLE 2-continued

Genes changed more than 2-fold in two independent Atwrky12-1 and Atwrky12-2 plants compared to wild type Col-0 control ("CK")

| Target Description | Public ID | Wrky12-1/CK | Wrky12-2/CK |
|---|---|---|---|
| senescence-associated protein contains similarity to ketoconazole resistant protein GI: 928938 and senescence-associated protein GI: 1046268 from [*Arabidopsis thaliana*]; supported by full-length cDNA: Ceres: 24140. | At5g66170 | 0.30 | 0.24 |
| ripening-related protein-likeripening-related protein, *Vitis vinifera*, EMBL: VVI237985; supported by full-length cDNA: Ceres: 9669. | At5g62350 | 0.42 | 0.24 |
| Expressed protein; supported by full-length cDNA: Ceres: 14423. | At4g39675 | 0.25 | 0.24 |
| hypothetical protein predicted by genemark.hmm | At1g19380 | 0.59 | 0.23 |
| beta-1,3-glucanase class I precursor; supported by full-length cDNA: Ceres: 3176. | At4g16260 | 0.24 | 0.23 |
| unknown protein | At2g22860 | 0.53 | 0.23 |
| Leucoanthocyanidin dioxygenase-like protein Leucoanthocyanidin dioxygenase, apple tree, PIR: S33144 | At3g55970 | 0.23 | 0.23 |
| beta-glucosidase, putative identical to GI: 6651430 from [*Arabidopsis thaliana*]; supported by cDNA: gi_14532461_gb_AY039855.1_ | At1g52400 | 0.58 | 0.23 |
| unknown protein; supported by cDNA: gi_15451161_gb_AY054661.1_ | At2g39030 | 0.32 | 0.23 |
| putative GH3-like protein similar to soybean GH3 auxin-inducible protein, GenBank accession number X60033; supported by cDNA: gi_16649142_gb_AY059941.1_ | At4g03400 | 0.58 | 0.23 |
| putative protein SRG1 protein - *Arabidopsis thaliana*, PIR: S44261 | At3g49620 | 0.36 | 0.22 |
| ABA-responsive protein - like ABA-responsive protein, *Hordeum vulgare*, EMBL: AF026538 | At5g13200 | 0.52 | 0.22 |
| NAM-like | At5g46590 | 0.52 | 0.22 |
| UDP rhamnose--anthocyanidin-3-glucoside rhamnosyltransferase - like protein UDP rhamnose--anthocyanidin-3-glucoside rhamnosyltransferase, *Petunia x hybrida*, PIR2: S36655 | At4g27570 | 0.50 | 0.22 |
| unknown protein; supported by full-length cDNA: Ceres: 37069. | At1g23850 | 0.44 | 0.22 |
| cytochrome P450 | At5g52320 | 0.44 | 0.22 |
| Peroxidase (emb|CAA68212.1) supported by full-length cDNA: Ceres: 37564. | At5g06720 | 0.47 | 0.21 |
| unknown protein | At1g22890 | 0.20 | 0.21 |
| unknown protein; supported by full-length cDNA: Ceres: 15081. | At2g22170 | 0.32 | 0.21 |
| unknown protein; supported by full-length cDNA: Ceres: 39579. | At1g19530 | 0.23 | 0.21 |
| 12-oxophytodienoate-10,11-reductase; supported by cDNA: gi_15294261_gb_AF410322.1_AF410322 | At2g06050 | 0.50 | 0.19 |
| class IV chitinase (CHIV) | At3g54420 | 0.24 | 0.19 |
| auxin conjugate hydrolase (ILL5) identical to auxin conjugate hydrolase [*Arabidopsis thaliana*] (ILL5) GI: 5725649; contains nonconsensus AT acceptor splice site at exon3 | At1g51780 | 0.42 | 0.19 |
| putative trypsin inhibitor | At2g43530 | 0.50 | 0.18 |
| Putative auxin-responsive protein; supported by cDNA: gi_15292854_gb_AY050861.1_ | At2g46370 | 0.32 | 0.18 |
| Putative monodehydroascorbate reductase (NADH) similar to monodehydroascorbate reductase (NADH) GB: JU0182 [*Cucumis sativus*]; supported by full-length cDNA: Ceres: 11160. | At3g09940 | 0.20 | 0.17 |
| photoassimilate-responsive protein PAR-like protein; supported by full-length cDNA: Ceres: 17872. | At5g52390 | 0.15 | 0.17 |
| unknown protein | At3g30720 | 0.16 | 0.16 |
| Polygalacturonase inhibiting protein; supported by full-length cDNA: Ceres: 35527. | At5g06870 | 0.48 | 0.16 |
| unknown protein contains similarity to chlorophyllase GI: 7415999 from [*Chenopodium album*]; supported by full-length cDNA: Ceres: 31589. | At1g19670 | 0.40 | 0.15 |
| Putative tyrosine aminotransferase; supported by full-length cDNA: Ceres: 14570. | At2g24850 | 0.26 | 0.15 |
| glutathione S-transferase identical to GB: X89216; supported by full-length cDNA: Ceres: 6528. | At2g29450 | 0.50 | 0.15 |
| AtPP-like protein AtPP protein, *Brassica napus*, EMBL: BNA245479; supported by cDNA: gi_15293070_gb_AY050969.1_ | At3g44860 | 0.58 | 0.14 |
| Mucin -like protein hemomucin, *Drosophila melanogaster*, EMBL: DM42014; supported by full-length cDNA: Ceres: 38956. | At3g51450 | 0.45 | 0.14 |

TABLE 2-continued

Genes changed more than 2-fold in two independent Atwrky12-1 and
Atwrky12-2 plants compared to wild type Col-0 control ("CK")

| Target Description | Public ID | Wrky12-1/CK | Wrky12-2/CK |
|---|---|---|---|
| Cytochrome P450-like protein; supported by full-length cDNA: Ceres: 101598. | At5g63450 | 0.44 | 0.13 |
| putative disease resistance protein | At2g34930 | 0.32 | 0.13 |
| putative antifungal protein | At2g26020 | 0.16 | 0.13 |
| hypothetical protein similar to putative ripening-related protein GI: 7406710 from [Vitis vinifera] | At1g70830 | 0.26 | 0.12 |
| leucoanthocyanidin dioxygenase-like protein; supported by full-length cDNA: Ceres: 13012. | At5g05600 | 0.36 | 0.11 |
| antifungal protein-like (PDF1.2) | At5g44420 | 0.10 | 0.09 |
| pEARLI 1; supported by cDNA: gi_871779_gb_L43080.1_ATHPEAR | At4g12480 | 0.06 | 0.07 |
| hypothetical protein | At3g25760 | 0.40 | 0.06 |

The promoters of NST2 and both C3H zinc finger TFs contain a conserved W-box TTGACT or TTGACC motif which can be bound by WRKY TFs. Electrophoretic mobility shift assays (EMSA) using heterologously expressed AtWRKY12 protein revealed that AtWRKY12 could bind directly to the NST2 promoter fragment (FIG. 4D), but not to the promoters of the two C3H zinc finger TFs (FIG. 5).

Example 5

Plant Materials and Growth Conditions

Tobacco (Nicotiana tabacum) Tnt1 retrotransposon tagged mutants of M. truncatula (Tadege et al., 2005; Tadege et al., 2008) were screened for defects in secondary cell wall formation. Plants were grown at 24° C. day/20° C. night, 16 h day/8 h night photoperiod, 70-80% relative humidity, and 150 µmol/m²/s light intensity. Sixth internodes counting from the top of each plant were harvested when the plants had reached around eight internodes, and were stored at −80° C. Cross sections (100 µm) of the sixth internodes were cut with a Vibratome 1500 system (Vibratome-Leica Microsystems, Bannockburn, Ill.). Micrographs were taken under a Nikon Micophot-FX system with a Nikon DXM 1200 color camera with consistent settings (Nikon, Madison, N.J.).

Example 6

Pith Cell Isolation from M. truncatula and Arabidopsis Plants

To isolate the pith from M. truncatula, stems were cut into 2 cm segments, and surrounding fiber and vascular tissues were removed by a blade under a stereomicroscope. About 15 main stems from different individual plants were used for pith isolation and pooled together for lignin analysis. After freezing with liquid nitrogen, the isolated pith material was kept at −80° C. To isolate pith from Arabidopsis, stems were cut into 0.5 cm segments and fixed immediately on ice in 75% (v/v) ethanol and 25% (v/v) acetic acid overnight. The fixative was exchanged by 10% (w/v) sucrose solution in PBS buffer (137 mM NaCl, 8.01 mM $Na_2HPO_4$, 2.68 mM KCl, and 1.47 mM $KH_2PO_4$, pH 7.3) and kept at 4° C. for 2 h, and then exchanged overnight by 15% (w/v) sucrose in the same buffer. The segments were longitudinally sectioned at 60 µm using a Leica CM1 850 cryostat (Leica Microsystems, Bannockburn, Ill.), and mounted on membrane-coated glass slides. Pith and fiber tissues were then separated using microknives, picked using tweezers together with the membrane, and frozen at −80° C.

Example 7

Immunochemistry and Microscopy

Tissue processing and immunolocalization using monoclonal antibodies to recognize various carbohydrate epitopes were carried out as described (Pattathil et al., 2010). Monoclonal antibodies used in this study were obtained as hybridoma cell culture supernatants from either the Complex Carbohydrate Research Center (CCRC, JIM and MAC series; available from CarboSource Services (Athens, Ga.), or the LM series, PAM1, from PlantProbes (Leeds, UK). The antibodies used recognize apparently distinct xylan epitopes as described (Pattathil et al., 2010). CBM2a was obtained from Dr. Harry Gilbert (CCRC, Athens, Ga.), and its immunolabeling required an additional anti-HIS antibody (catalog number H-1029, Sigma, St. Louis, Mo.) binding step. For transmission electron microscopy (TEM), 80 nm sections were taken and stained with 2% uranyl acetate for 5 min and with Reynold's lead citrate (Reynolds, 1963) for 1 min. Sections were observed under a Zeiss 902A TEM (Carl Zeiss, DE) operated at 80 kV.

Example 8

Molecular Cloning of MtSTP Gene

To identify the gene linked to the STP phenotype, candidate genes were chosen based on extent of down-regulation and stem expression specificity. PCR was performed using Tnt1 (forward primer 5'-TCCTTGTTGGATTGGTAGC-CAACTTTGTTG-3'; SEQ ID NO:31), reverse primer 5'-AGTTGGCTACCAATCCAACAAGGA-3'; SEQ ID NO:32) and gene specific primers MtSTPFw 5'-ATGGATG-GAGAAAGAGATGTTCC-3' (SEQ ID NO:33) and MtST-PRe 5'-TCAAAAAGACGTAAAACATTCGTG-3' (SEQ ID NO:34) to detect Tnt1 insertions.

For real-time PCR, cDNA samples were used for Quantitative Real-time PCR (qRT-PCR) with technical duplicates. The 10 pl reaction included 2 pl of primers (0.5 pM of each primer), 5 pl Power Sybr® (Applied Biosystems, Foster City, Calif.), 2 pl 1:20 diluted cDNA from the reverse transcription step, and 1 pl water. qRT-PCR data were analyzed using SDS 2.2.1 software (Applied Biosystems). PCR efficiency was estimated using the LinRegPCR software (Ramakers et al., 2003) and transcript levels were determined by relative quantification (Pfaffl, 2001) using the *M. truncatula* actin gene as a reference.

Example 9

Protoplast Isolation and Trans-activation Assay

*Arabidopsis* protoplasts were isolated according to a previously published protocol with minor modifications (Asai et al., 2002; Sheen, 2001). In brief, leaves from healthy 30-day-old *Arabidopsis* were cut into 0.5-1 mm strips with fresh razor blades. The leaf strips were put into an enzyme solution composed of cellulase and macerozyme, then vacuum infiltrated for 5-30 min with continued digestion for 3 h without shaking in the dark. The enzyme solution containing protoplasts was then filtered with a 35-75 μm nylon mesh, and protoplasts were collected and transformed by PEG mediated transfection. The firefly luciferase construct was modified from the Gateway compatible vector pPGWL7 (Karimi et al. 2002). Promoter activities were represented by firefly LUC/Renilla LUC activities, and normalized to the value obtained from protoplasts transformed with empty vector.

Example 10

Gene Constructs and Plant Transformation

To make the complementation construct, the AtWRKY genomic sequence was PCR amplified using the following primers: WRKY12GenomFw, 5'-TGTAATCATTGTTG-CATGGAATTCATC-3' (SEQ ID NO:35), and WRKYGen-omRe, 5'-AGCGGATCCTGTAACGACTAGACG-TAAACTTAAC-3' (SEQ ID NO:36). The PCR product was cleaved by digestion with EcoRI/BamHI, and ligated to pCAMBIA3300 vector. To make the 35S: AtWRKY12-YFP fusion overexpression construct, the coding sequence of AtWRKY12 was cloned by PCR using the following primers:

```
AtWRKY12Fw
5'-caccATGGAAGGAGGAGGGAGAAG-3',     (SEQ ID NO: 37)
and

AtWRKY12Re
5'-AAAGGAAGAGAGACAATCATGG-3'.        (SEQ ID NO: 38)
```

To make the MtSTP overexpression construct, the coding sequence was amplified using MtSTPFw 5'-caccATGGATG-GAGAAAGAGATGTTCC-3' (SEQ ID NO:39), and MtST-PRe 5'-TTATTGGAACGACATTGTTGGATC-3' (SEQ ID NO:40). The resulting PCR products were cloned into the pENTR vector (Invitrogen, Carlsbad, Calif.), and, after sequencing, the insertion fragments were subcloned to the destination vectors pB7YWG2 or pB2GW7 (Karimi et al., 2002) by LR reaction. All constructs were confirmed by sequencing and transformed to *Agrobacterium* AGL1. Transformation of *Arabidopsis* was by the floral dip procedure (Clough & Bent, 1998).

Example 11

Protein Expression and Electrophoretic Mobility Shift Assays (EMSA)

To express the recombinant AtWRKY12 protein, the coding sequence was fused in frame with maltose binding protein (MBP), expressed in *E. coli*, and the recombinant protein was purified using amylose resin. The pure protein was used for EMSA with the NST2 or C3H promoter fragments. Double-strand probe and competitor fragments were made from annealing of separately synthesized strands, with/without one 5' biotin labeled strand. The sequence used for NST2 was:

```
                                     (SEQ ID NO: 41)
5'-AAAGAGACCATTAGTATATTTGACCCAAAAAAAAATAAAAAAAAA
GAG-3'.
```

For C3H the sequence was: 5'-TGGAAGATGCATGT-TATTGACTAAATATGATCTACCA-3' (SEQ ID NO:42); and for C3HL the sequence was 5'-TGGCTTAAATCATAT-TGACAAGACCCATTAAAAAGAGG-3' (SEQ ID NO:43). The conserved WRKY binding motifs are underlined. The biotin-labeled and competitor DNA fragments were incubated for 20 min with 100 ng of AtWRKY12-MBP in binding buffer according to the EMSA kit protocol (Pierce, Rockford, Ill.), and reaction mixtures were loaded for polyacrylamide gel electrophoresis. The DNA was electroblotted onto nitrocellulose membrane and detected by the chemiluminescent method.

Example 12

Determination of Lignin Content and Composition

Lignin content of stem material (internodes 5-8) was determined by the acetyl bromide method using ~15 mg extractive-free material (Hatfield et al., 1999). The same molar extinction coefficient of 17.2 (as determined for lignin from wild-type alfalfa) was used for samples for all the transgenic lines. Phloroglucinol and Mäule staining were conducted as described (Guo et al., 2001).

Example 13

Lignin Modification in Monocot Plants

Figure 16:
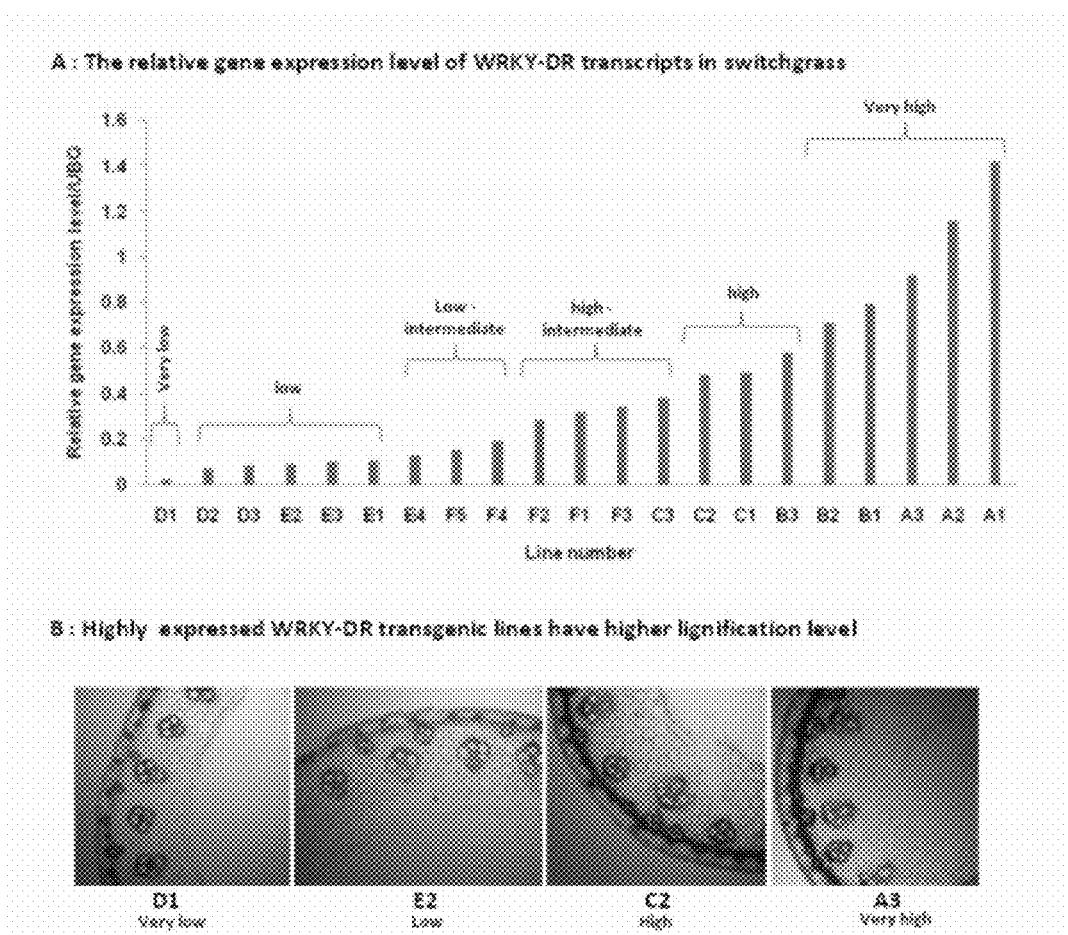
FIG. 16. (A) Relative gene expression level of WRKY dominant repressor construct ("WRKY-DR") transcripts in selected transgenic switchgrass (*Panicum virgatum*) lines. (B) tissue from exemplary selected lines D1, E2, C2, and A3 classified as "very low," "low," "high," and "very high" in (A) above, stained to show lignification; and (C) histograms of biomass density from selected switchgrass lines. WRKY-DR transcript expression was normalized relative to ubiquitin (ubq) expression.
Figure 16:
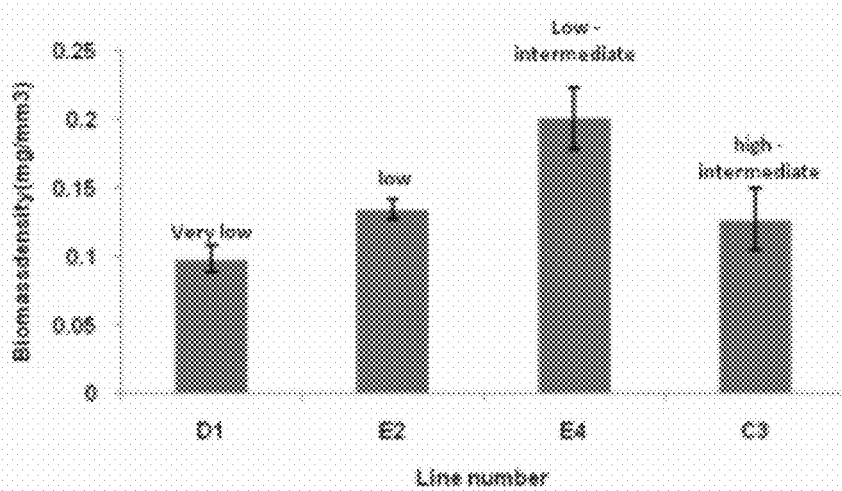
Figure 17:
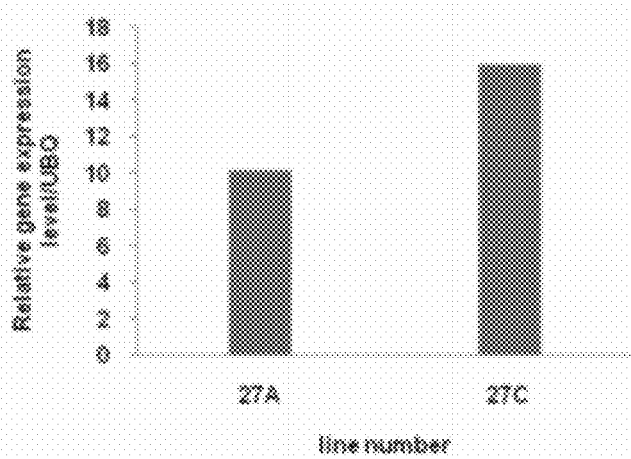
FIG. 17. (A) Relative gene expression level of WRKY dominant repressor construct ("WRKY-DR") transcripts in selected trangenic corn (*Zea mays*) lines. (B) Phloroglucinol staining of transgenic tissue from the two lines. WRKY-DR transcript expression was normalized relative to ubiquitin (ubq) expression.
Figure 17:
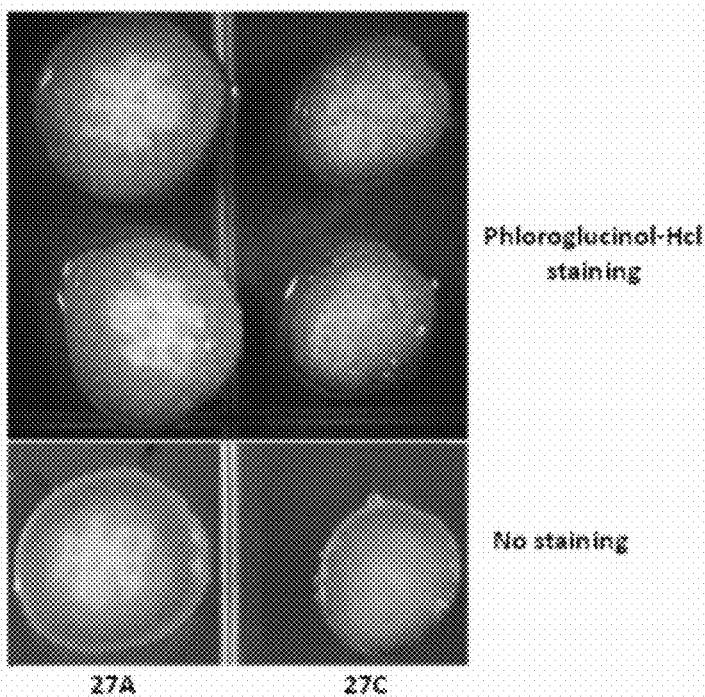

A dominant repressor construct was utilized to down-regulate WRKY gene expression in representative monocotyledenous plants. Down-regulation of WRKY gene expression increased lignification in switchgrass (FIG. 16) and maize (corn) (FIG. 17), as it had in *Medicago* and *Arabidopsis*. FIG. 16 shows results from switchgrass, wherein lines with higher expression of a dominant-repressor ("WRKY-DR") construct demonstrated higher lignification. As shown in FIG. 16(C), biomass density may also be modulated. Similarly, FIG. 17 demonstrates that a line with higher level expression of WRKY-DR transcripts displays increased lignification as measured by phlorogucinol-HCl staining. Thus, this approach for modifying lignin content is applicable to monocots as well as to dicots.

All of the methods disclosed and claimed herein can be made and executed without undue experimentation in light of the present disclosure. While the compositions and methods of this invention have been described in terms of illustrative embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 4,461,648; 4,535,060; 5,000,000; 5,037,663; 5,302,523; 5,322,783; 5,384,253; 5,464,765; 5,508,184; 5,538,877; 5,538,880; 5,545,818; 5,550,318; 5,563,055; 5,591,616; 5,610,042.
U.S. Pat. Publ 20040049802
Abdullah et al.; *Biotechnology*, 4:1087, 1986.
Alexander, *Stain Technol.*, 44: 117-122, 1969.
Asai et al., *Nature* 415:977, 2002.
Bates, *Mol. Biotechnol.*, 2:135-145, 1994.
Battraw et al.; *Theor. App. Genet.*, 82:161-168, 1991.
Benedito et al.; *Plant J.* 55:504, 2008.
Bevan et al.; *Nucleic Acids Research*, 11:369-385, 1983.
Bhattacharjee et al.; *J. Plant Bioch. and Biotech.* 6:69-73, 1997.
Blake et al., *J. Biol. Chem.* 281:29321, 2006.
Bouchez et al.; *EMBO Journal*, 8:4197-4204, 1989.
Bower et al.; *Plant Journal*, 2:409-416. 1992.
Buising et al.; *Mol Gen Genet*, 243:71-81. 1994.
Callis et al.; *Genes Dev.*, 1:1183-1200, 1987.
Cano-Delgado et al., *Devel.* 127:3395, 2000.
Casa et al.; *Proc. Natl. Acad. Sci. USA*, 90:11212-11216, 1993.
Chandler et al.; *The Plant Cell*, 1:1175-1183, 1989.
Christou, et al.; *Proc. Natl. Acad. Sci. USA*, 84:3962-3966, 1987.
Chu et al.; *Scientia Sinica*, 18:659-668, 1975.
Clough & Bent, *Plant J.* 16:735, 1998.
Conkling et al.; *Plant Physiol.*, 93:1203-1211, 1990.
De Block et al.; *EMBO Journal*, 6:2513-2518, 1987.
De Block et al.; *Plant Physiol.*, 91:694-701, 1989.
Dellaporta et al.; *Chromosome Structure and Function: Impact of New Concepts*, 18th Stadler Genetics Symposium, 11:263-282, 1988.
Devane et al., *Science*, 258:1946-1949, 1992
D'Halluin et al.; *Plant Cell*, 4:1495-1505, 1992.
Dixon, et al.; *Rec Adv Phytochem.*, 28:153-178, 1994.
Downward, *BMJ*, 328(7450):1245-1248, 2004.
Dozmorov & Centola, *Bioinformatics* 19:204, 2003.
Duff and Murray, *Bioresource Tech.*, 55:1-33, 1995.
Ebert et al.; 84:5745-5749, *Proc. Natl. Acad. Sci. USA*, 1987.
Ellis et al.; *EMBO Journal*, 6:3203-3208, 1987.
Ellis et al., *Plant Cell* 14:1557, 2002.
Fire et al.; *Nature*, 391: 806-11, 1998.
Fraley et al.; *Bio/Technology*, 3:629-635, 1985.
Fromm et al.; *Nature*, 319:791-793, 1986.
Fukushima and Hatfield, *J. Agric. Food Chem.* 52:3713-3720, 2004.
Gallie et al.; *The Plant Cell*, 1:301-311, 1989.
Ghosh-Biswas et al.; *J. Biotechnol.*, 32:1-10, 1994.
Gong et al.; *Adv. Biochem. Engng. Biotech.* 65: 207-241, 1999.
Guo et al., *Plant Cell* 13:73, 2001.
Hagio et al.; *Plant Cell Rep.*, 10:260-264, 1991.
Hamilton et al; *Proc. Natl. Acad. Sci. USA*, 93:9975-9979, 1996.
Haseloff et al; *Proc. Natl. Acad. Sci. USA*, 94:2122-2127, 1997.
Hatfield et al.; *Crop Science*, 39: 27-37, 1999.
He et al.; *Plant Cell Reports*, 14 (2-3):192-196, 1994.
Hensgens et al.; *Plant Mol. Biol.*, 22(6):1101-1127, 1993.
Hiei et al.; *Plant. Mol. Biol.*, 35(1-2):205-218, 1997.
Hinchee et al.; *Bio/technol.*, 6:915-922, 1988.
Hou et al, *Plant Physiology*, 111:166, 1996.
Hu et al.; *Nat. Biotechnol.* 17:808-812, 1999.
Hudspeth et al, *Plant Mol. Biol.*, 12:579-589, 1989.
Ikuta et al.; *Bio/technol.*, 8:241-242, 1990.
Irizarry et al., *Nucl. Acids Res.* 31:e15, 2003.
Ishida et al.; *Nat. Biotechnol.*, 14:745-750, 1996.
Jones et al.; *Planta*, 221:255-264, 2005.
Kaeppler et al.; *Plant Cell Reports*, 9:415-418, 1990.
Kaeppler et al; *Theor. Appl. Genet.*, 84:560-566, 1992.
Karimi et al., *Trends Pl. Sci.* 7:193, 2002.
Katz et al.; *J. Gen. Microbiol.*, 129:2703-2714, 1983.
Klee et al.; *Bio-Technology*, 3:637-642, 1985.
Knittel et al.; *Plant Cell Reports*, 14:81-86, 1994.
Ko et al., *Plant J.* 60:649, 2009.
Lapierre et al., *J. Wood. Chem. Technol.* 5:277, 1985.
Lapierre et al.; *Res. Chem. Intermed.* 21:397-412, 1995.
Lawton et al.; *Plant Mol. Biol.*, 9:315-324, 1987.
Lazzeri, *Methods Mol. Biol.*, 49:95-106, 1995.
Lee et al.; *Adv. Biochem. Engng. Biotech.*, 65: 93-115, 1999
Lee et al.; *Korean J. Genet.*, 11:65-72, 1989.
Leek et al., *Bioinformatics* 22:507, 2006.
Lehner et al.; *Brief Funct Genomic Proteomic*, 3:68-83, 2004.
Li et al., *PNAS* 98:31, 2001.
Lorz et al.; *Mol Gen Genet*, 199:178-182, 1985.
Marcotte et al.; *Nature*, 335:454, 1988.
Mes-Hartree, et al.; *Appl. Microbiol. Biotechnol.*, 29:462-468, 1988.
Morjanoff and Gray, *Biotechnol. Bioeng.* 29:733-741, 1987.
Murakami et al.; *Mol. Gen. Genet.*, 205:42-50, 1986.
Murashige et al, *Physiol. Plant*, 15:473-497, 1962.
Nagatani et al.; *Biotech. Tech.*, 11:471-473, 1997.
Odell et al.; *Nature*, 313:810-812, 1985.
Ogawa et al.; *Sci. Rep.*, 13:42-48, 1973.
Olsson et al.; *Enzyme and Microb. Technol.* 18:312-331, 1996.
Omirulleh et al.; *Plant Mol. Biol.*, 21:415-428, 1993.
Ow et al.; *Science*, 234:856-859, 1986.
Pattathil et al., *Pl. Physiol.* 153:514, 2010.
PCT App. WO 94/09699
PCT App. WO 95/06128
PCT App. WO 97/41228
PCT App. WO 97/4103
PCT App. WO 92/17598
Pfaffl, *Nucleic Acids Res.*, 29: e45, 2001.
Potrykus et al.; *Mol. Gen. Genet.*, 199:183-188, 1985.
Prasher et al.; *Biochem. Biophys. Res. Commun.*, 126(3): 1259-1268, 1985.
Ramakers et al.; *Neurosci Lett.*, 339: 62-66, 2003.
Reddy et al; *Proc. Nat. Acad. Sci.*, 102:16573-16578, 2005.
Reichel et al; *Proc. Natl. Acad. Sci*, 93: 5888-5893. 1996.
Reynolds, *J. Cell Biol.* 17:208, 1963.
Reynolds, *Nat. Biotechnol.* 22:326-330, 2004.
Rhodes et al; *Methods Mol. Biol.*, 55:121-131, 1995.
Richards et al.; *Plant Cell Rep.* 20:48-54, 2001.
Ritala et al.; *Plant Mol. Biol.*, 24(2):317-325, 1994.
Rogers et al; *Methods Enzymol.*, 153:253-277, 1987.
Sambrook et al; *In: Molecular Cloning—A Laboratory Manual* (second edition), Cold Spring Harbour Laboratory Press, 1989.
Sheen et al.; *Plant Journal*, 8:777-784, 1995.
Sheen et al., *Pl. Physiol.* 127:1466, 2001.
Singsit et al.; *Transgenic Res.*, 6(2):169-176, 1997.

Somleva et al.; *Crop Science,* 42:2080-2087, 2002.
Stalker et al.; *Science,* 242:419-422, 1988.
Storey et al., *PNAS* 100:9440, 2003.
Sullivan et al.; *Mol. Gen. Genet.,* 215(3):431-440, 1989.
Sun and Cheng, *Bioresource Technol.* 83:1-11, 2002.
Sutcliffe, *Proc. Natl. Acad. Sci.,* 75:3737-3741, 1978.
Tadege et al.; *Trends Plant Sci.,* 10: 229-235, 2005.
Tadege et al.; *Plant J.,* 54: 335-347, 2008.
Thillet et al.; *J. Biol. Chem.,* 263:12500-12508, 1988.
Thomas et al.; *Plant Sci.* 69:189-198, 1990.
Thompson et al.; *Euphytica,* 85:75-80, 1995.
Thompson et al; *The EMBO Journal,* 6(9):2519-2523, 1987.
Tian, Sequin, Charest, *Plant Cell Rep.,* 16:267-271, 1997.
Tingay et al; *The Plant Journal,* (6) p. 1369-1376. 1997.
Tomes et al.; *Plant. Mol. Biol.* 14(2):261-268, 1990.
Torbet et al.; *Crop Science,* 38(1):226-231, 1998.
Torbet et al.; *Plant Cell Reports,* 14(10):635-640, 1995.
Toriyama et al; *Theor Appl. Genet.,* 73:16, 1986.
Tsukada et al.; *Plant Cell Physiol.,* 30(4)599-604, 1989.
Twell et al.; *Plant Physiol.,* 91:1270-1274, 1989.
Uchimiya et al.; *Mol. Gen. Genet.,* 204:204, 1986.
Vasil et al.; *Plant Physiol.,* 91:1575-1579, 1989.
Walker et al; *Proc. Natl. Acad. Sci. USA,* 84:6624-6628, 1987.
Wang et al.; *Molecular and Cellular Biology,* 12(8):3399-3406, 1992.
Wyman, *Annu. Rev. Energy Environ.* 24:189-226, 1999.
Yamada et al.; *Plant Cell Rep.,* 4:85, 1986.
Yamaguchi et al., *Plant J.* 55:652, 2008.
Yang et al; *Proc. Natl. Acad. Sci.,* 87:4144-4148, 1990.
Zhang et al.; *Science* 267:240-243, 1995.
Zhao et al., *Plant J. Plant Journal* 63:100-114, 2010.
Zhong et al., *Plant Cell,* 20: 2763-2782, 2008.
Zhou et al.; *Plant Cell Reports,* 12.612-616, 1993.
Zhou et al., *Plant Cell* 21:248, 2009.
Zukowsky et al; *Proc. Natl. Acad. Sci. USA,* 80:1101-1105, 1983.

What is claimed is:

1. A nucleic acid molecule comprising a nucleic acid sequence selected from the group consisting of:
   (a) a nucleic acid sequence comprising the sequence of SEQ ID NO: 14;
   (b) a nucleic acid sequence exhibiting at least 90% sequence identity to SEQ ID NO: 14 and that encodes a WRKY transcription factor;
   (c) the full-length complement of (a) or (b);
   (d) a nucleic acid fragment comprising at least 18 contiguous nucleotides of (a), wherein expression of the fragment in a plant down-regulates the WRKY transcription factor encoded by the nucleic acid sequence of (b) in the plant and increases the lignin, cellulose, hemicellulose, and/or xylan content of said plant;
   wherein the nucleic acid sequence is operably linked to a heterologous promoter sequence.

2. The nucleic acid molecule of claim 1, comprising a nucleic acid sequence exhibiting at least 95%, 96%, 97%, 98% or 99% sequence identity to the nucleic acid sequence SEQ ID NO: 14 or a complement thereof.

3. The nucleic acid molecule of claim 1, wherein the heterologous promoter sequence is a developmentally-regulated, inducible, tissue-specific, constitutive, cell-specific, seed specific, or germination-specific promoter.

4. The nucleic acid molecule of claim 1, wherein the nucleic acid molecule comprises the nucleic acid sequence of (a)-(c), and wherein expression of the nucleic acid molecule in a plant cell reduces the lignin content of pith cells of said plant.

5. The nucleic acid molecule of claim 1, wherein the nucleic acid fragment of (d).

6. The nucleic acid molecule of claim 5, wherein the lignin, cellulose, hemicellulose and/or xylan content of pith cells of said plant is increased.

7. A transgenic plant cell comprising the nucleic acid molecule of claim 1.

8. A transgenic plant or plant part comprising the nucleic acid molecule of claim 1.

9. A transgenic plant cell comprising the nucleic acid molecule of claim 5.

10. A transgenic plant or plant part comprising the nucleic acid molecule of claim 5.

11. The transgenic plant of claim 10, wherein pith cells of the plant comprise a secondary cell wall.

12. A biofuel feedstock comprising the nucleic acid molecule of claim 5.

13. A method of increasing the level of lignin, cellulose, hemicellulose, or a xylan in a crop plant comprising down-regulating a WRKY transcription factor in the plant, wherein the crop plant comprises a nucleic acid sequence exhibiting at least 90% sequence identity of SEQ ID NO: 14; and selecting the plant comprising an increased level of lignin, cellulose, hemicellulose, or a xylan relative to the wild type lignin level.

14. The method of claim 13, wherein the crop plant comprises an increased level of lignin relative to the wild type lignin level, prior to down-regulating the WRKY transcription factor in the plant.

15. A plant produced by the method of claim 14, wherein the plant comprises an increased level of lignin, cellulose, hemicellulose, or a xylan relative to an otherwise isogenic plant that displays a wild type level of lignin in the absence of a down regulated WRKY transcription factor, wherein the plant comprises a nucleic acid fragment comprising at least 18 contiguous nucleotides of SEQ ID NO:14 or at least 18 contiguous nucleotides of a complement of SEQ ID NO:14.

16. The method of claim 13, wherein the plant is a dicotyledonous plant.

17. The method of claim 13, wherein the plant is a monocotyledonous plant.

18. The method of claim 13, wherein the plant is selected from the group consisting of: switchgrass (*Panicum virgatum*), giant reed (*Arundo donax*), reed canarygrass (*Phalaris arundinacea*), *Miscanthus x giganteus, Miscanthus* sp., sericea lespedeza (*Lespedeza cuneata*), corn, sugarcane, sorghum, millet, ryegrass (*Lolium multiflorum, Lolium* sp.), timothy, *Kochia* (*Kochia scoparia*), forage soybeans, alfalfa, clover and other legumes, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, poplar, willow, and agave.

19. A method of decreasing the lignin content in a plant comprising expressing a WRKY transcription factor in the plant, and selecting the plant comprising a decreased level of lignin relative to the wild type lignin level, wherein the WRKY transcription factor is encoded by a nucleic acid sequence exhibiting at least 90% sequence identity of SEQ ID NO: 14 and wherein the nucleic acid is operably linked to a heterologous promoter.

20. The method of claim 19, wherein the digestibility of feed harvested or prepared from the crop is increased.

21. A method of increasing the lignin content of pith cells of a plant comprising expressing the nucleic acid molecule according to claim 5 in the plant.

22. A method for producing a commercial product comprising obtaining a plant of claim 8 or a part thereof and producing a commercial product therefrom.

23. The method of claim 22, wherein the commercial product is paper, paper pulp, ethanol, biodiesel, silage, animal feed or fermentable or gasifiable biofuel feedstock.

* * * * *

UNITED STATES PATENT AND TRADEMARK OFFICE
CERTIFICATE OF CORRECTION

Page 1 of 1

PATENT NO. : 9,045,549 B2
APPLICATION NO. : 13/288677
DATED : June 2, 2015
INVENTOR(S) : Huanzhong Wang et al.

It is certified that error appears in the above-identified patent and that said Letters Patent is hereby corrected as shown below:

In the Claims

Column 97, Line 31, please delete "wherein the nucleic acid fragment of (d)" and please insert -- comprising the nucleic acid fragment of (d) --

Signed and Sealed this
Fifteenth Day of December, 2015

Michelle K. Lee
*Director of the United States Patent and Trademark Office*